(12) United States Patent
Hasegawa et al.

(10) Patent No.: US 7,868,199 B2
(45) Date of Patent: Jan. 11, 2011

(54) FLUOROALCOHOL PREPARATION METHOD, FLUORINATED MONOMER, POLYMER, RESIST COMPOSITION AND PATTERNING PROCESS

(75) Inventors: Koji Hasegawa, Joetsu (JP); Takeshi Kinsho, Joetsu (JP); Tsunehiro Nishi, Joetsu (JP); Masaki Ohashi, Joetsu (JP); Takeru Watanabe, Joetsu (JP)

(73) Assignee: Eudyna Devices Inc., Yamanashi (JP)

( * ) Notice: Subject to any disclaimer, the term of this patent is extended or adjusted under 35 U.S.C. 154(b) by 1001 days.

(21) Appl. No.: 11/699,390

(22) Filed: Jan. 30, 2007

(65) Prior Publication Data

US 2007/0179309 A1 Aug. 2, 2007

(30) Foreign Application Priority Data

Jan. 31, 2006 (JP) ............................. 2006-022319

(51) Int. Cl.
*C07C 69/74* (2006.01)
(52) U.S. Cl. ................... 560/116; 560/117; 560/120; 560/129; 560/227
(58) Field of Classification Search .......... 560/227, 560/116, 117, 120, 129
See application file for complete search history.

(56) References Cited

U.S. PATENT DOCUMENTS

| | | | |
|---|---|---|---|
| 3,438,946 | A | 4/1969 | Lichstein et al. |
| 5,714,625 | A | 2/1998 | Hada et al. |
| 6,004,724 | A | 12/1999 | Yamato et al. |
| 6,261,738 | B1 | 7/2001 | Asakura et al. |
| 6,312,867 | B1 | 11/2001 | Kinsho et al. |
| 6,774,258 | B2 | 8/2004 | Hasegawa et al. |
| 6,800,418 | B2 | 10/2004 | Yoon et al. |
| 6,830,866 | B2 | 12/2004 | Kobayashi et al. |
| 6,964,840 | B2 | 11/2005 | Nishimura et al. |
| 2003/0078352 | A1 | 4/2003 | Miyazawa et al. |
| 2003/0224283 | A1 | 12/2003 | Allen et al. |
| 2006/0246377 | A1 | 11/2006 | Yamato et al. |
| 2006/0252897 | A1 | 11/2006 | Miyazawa et al. |

FOREIGN PATENT DOCUMENTS

| | | |
|---|---|---|
| EP | 1 164 434 A2 | 12/2001 |
| EP | 1 616 854 A1 | 1/2006 |
| JP | 9-95479 A | 4/1997 |
| JP | 9-208554 A | 8/1997 |
| JP | 9-230588 A | 9/1997 |
| JP | 9-301948 A | 11/1997 |
| JP | 2906999 B2 | 6/1999 |
| JP | 00/17139 A1 | 3/2000 |
| JP | 2000-314956 A | 11/2000 |
| JP | 2000-336121 A | 12/2000 |
| JP | 2001-240571 A | 9/2001 |
| JP | 2002-72484 A | 3/2002 |
| JP | 2002-179624 A | 6/2002 |
| JP | 2003-40840 A | 2/2003 |
| JP | 2003-66612 A | 3/2003 |
| JP | 2003-192729 A | 7/2003 |
| JP | 2004-46098 A | 2/2004 |
| JP | 2005-239710 A | 9/2005 |
| WO | WO 2004/074242 A2 | 9/2004 |

OTHER PUBLICATIONS

Japanese Office Action dated Feb. 17, 2010, issued in corresponding Japanese Patent Application No. 2006-022319.
European search report dated Aug. 9, 2007, issued in corresponding European Patent application No. 07250422.8.
Soai et al., Sodium Borohydride-T-Butyl Alcohol-Methanol as an Efficient System for the Selective Reduction of Esters, 1982, pp. 463-467, vol. 12, Synthetic Communications, Philadelphia, PA, US.
Database Beilstein, Beilstein Institute for Organic Chemistry, J. Chem. Soc., 1951, pp. 3067-3069.
Koji Arimitsu et al.; "Sensitivity Enhancement of Chemical-Amplification-Type Photoimaging Materials by Acetoacetic Acid Derivatives"; Journal of Photopolymer Science and Technology, vol. 8, No. 1, pp. 43-44, 1995.
Kazuaki Kudo et al.; "Enhancement of the Senesitivity of Chemical-Amplification-Type Photoimaging Materials by β-Tosyloxyketone Acetals"; Journal of Photopolymer Science and Technology, vol. 8, No. 1, pp. 45-46, 1995.

(Continued)

*Primary Examiner*—Shailendra Kumar
(74) *Attorney, Agent, or Firm*—Westerman, Hattori, Daniels & Adrian, LLP

(57) ABSTRACT

Fluoroalcohol compounds of formula (4) are prepared by reacting a fluorine compound of formula (1) with reducing agents or organometallic reagents of formulas (2) and (3) wherein $R^1$ is H or a monovalent $C_1$-$C_{20}$ hydrocarbon group in which any —$CH_2$— moiety may be replaced by —O— or —C(=O)—, $R^2$ is H or a monovalent $C_1$-$C_6$ hydrocarbon group, $R^3$ and $R^4$ are H or a monovalent $C_1$-$C_8$ hydrocarbon group, and $M^1$ is Li, Na, K, Mg, Zn, Al, B, or Si. From the fluoroalcohol compounds, fluorinated monomers can be produced in a simple and economic way, which are useful in producing polymers for the formulation of radiation-sensitive resist compositions.

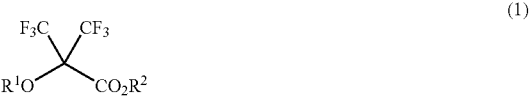

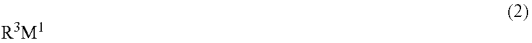

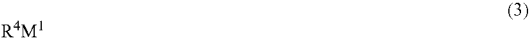

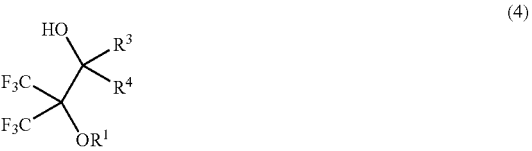

9 Claims, No Drawings

OTHER PUBLICATIONS

Koji Arimitsu et al.; "Effect of Phenolic Hydroxyl Residues on the Improvement of Acid-Proliferation-Type Photoimaging Materials"; Journal of Photopolymer Science and Technology, vol. 9, No. 1, pp. 29-30, 1996.

Soichi Owa et al.; "Immersion lithography; its potential performance and issues"; Optical Microlithograpy XVI, Proceedings of SPIE, vol. 5040, p. 724, 2003.

Taku Hirayama "Resist and Cover Material Investigation for Immersion Lithograph", $2^{nd}$. Immersion Workshop, Jul. 11, 2003.

Shinichi Kanna et al.; "Study and Control of the Interfacial Mass Transfer of Resist Components in 193 nm Immersion Lithography", Journal of Photopolymer Science and Technology, vol. 18, No. 5, p. 603, 2005.

US 7,868,199 B2

FLUOROALCOHOL PREPARATION METHOD, FLUORINATED MONOMER, POLYMER, RESIST COMPOSITION AND PATTERNING PROCESS

CROSS-REFERENCE TO RELATED APPLICATION

This non-provisional application claims priority under 35 U.S.C. §119(a) on Patent Application No. 2006-022319 filed in Japan on Jan. 31, 2006, the entire contents of which are hereby incorporated by reference.

TECHNICAL FIELD

This invention relates to a method for preparing fluoroalcohol compounds, and fluorinated monomers (or polymerizable compounds) derived therefrom. The fluoroalcohol compounds are useful as raw materials for the synthesis of functional materials, pharmaceutical and agricultural chemicals, and the fluorinated monomers are useful in producing polymers for the manufacture of radiation-sensitive resist compositions which are fully transparent to radiation having a wavelength of up to 500 nm, especially up to 300 nm, typically KrF, ArF and $F_2$ laser beams, and have good development characteristics.

The invention also relates to polymers comprising recurring units derived from the fluorinated monomers, photoresist compositions comprising the polymers, and a patterning process using the photoresist compositions.

BACKGROUND ART

While a number of recent efforts are being made to achieve a finer pattern rule in the drive for higher integration and operating speeds in LSI devices, deep-ultraviolet lithography is thought to hold particular promise as the next generation in microfabrication technology. In particular, photolithography using a KrF, ArF or $F_2$ laser as the light source is strongly desired to reach the practical level as the micropatterning technique capable of achieving a feature size of 0.3 μm or less. Various alkali-soluble resins are used as the base resin in such resists.

For KrF laser resists, a polyhydroxystyrene resin having phenolic hydroxyl groups as the alkali-soluble functional group is, in fact, a standard base resin. For ArF laser resists, poly(meth)acrylate resins using carboxyl groups as the alkali-soluble group and resins comprising polymerized units of cycloaliphatic olefin such as norbornene are under investigation. Of these, the poly(meth)acrylate resins are regarded, due to ease of polymerization, as a promising candidate that will find practical use. For these resist resins using as the alkali-soluble functional group carboxyl groups having a higher acidity than phenolic hydroxyl groups, however, an outstanding issue is difficulty of dissolution control, often leading to pattern collapse caused by swelling or the like.

Functional groups having an acidity comparable to phenolic hydroxyl groups are desired. It was proposed to use an alcohol having a plurality of fluorine atoms substituted at α- and α'-positions (e.g., having a partial structure: —$C(CF_3)_2$OH) as the alkali-soluble functional group, as described in G. Wallraff et al., Active Fluororesists for 157 nm lithography in 2nd International Symposium on 157 nm Lithography. Styrene and norbornene derivatives having fluoroalcohol —$C(CF_3)_2$OH incorporated therein are proposed as monomers used in the manufacture of base resins. Similar examples of fluoroalcohol-substituted norbornene are found in JP-A 2003-192729 and JP-A 2002-72484. For the polymerization of norbornene monomers, however, radical polymerization of monomers of the same type is difficult, and instead, special polymerization techniques such as coordinate polymerization using unique transition metal catalysts and ring-opening metathesis polymerization are necessary. Although alternating copolymerization between a norbornene monomer and a comonomer such as maleic anhydride or maleimide can be implemented by radical polymerization, the presence of comonomer imposes a substantial limit on the freedom of resin design.

JP-A 2003-040840 describes fluoroalcohol-substituted acrylate monomers. Although the method of preparing these monomers is not definite, the starting reactant used is hexafluoroacetone (boiling point −27° C.) which is awkward to handle because it is gaseous at room temperature. The synthesis of polymerizable compound must follow long steps, leaving the problems of an increased cost and difficult commercial implementation.

There is a strong demand to develop a polymerizable compound (or monomer) having both a polymerizable unsaturated group such as a (meth)acrylate structure and a functional group having an acidity comparable to phenolic hydroxyl, which compound can be prepared and polymerized both in an industrially acceptable and economic manner.

Over a decade, photolithography using ArF excimer laser light (193 nm) has been under active investigation. It was expected at the initial that the ArF lithography would be applied to the fabrication of 180-nm node devices. However, the KrF excimer lithography survived to the mass-scale fabrication of 130-nm node devices. So, the full application of ArF lithography started from the 90-nm node. The ArF lithography combined with a lens having an increased numerical aperture (NA) of 0.9 is considered to comply with 65-nm node devices. For the next 45-nm node devices which required an advancement to reduce the wavelength of exposure light, the $F_2$ lithography of 157 nm wavelength became a candidate. However, for the reasons that the projection lens uses a large amount of expensive $CaF_2$ single crystal, the scanner thus becomes expensive, hard pellicles are introduced due to the extremely low durability of soft pellicles, the optical system must be accordingly altered, and the etch resistance of resist is low; the postponement of $F_2$ lithography and the early introduction of ArF immersion lithography were advocated (see Proc. SPIE Vol. 4690 xxix).

In the ArF immersion lithography, the space between the projection lens and the wafer is filled with water. Since water has a refractive index of 1.44 at 193 nm, pattern formation is possible even using a lens with NA of 1.0 or greater. Theoretically, it is possible to increase the NA to 1.44. The resolution is improved by an increment of NA. A combination of a lens having NA of at least 1.2 with ultra-high resolution technology suggests a way to the 45-nm node (see Proc. SPIE Vol. 5040, p 724).

Several problems associated with the presence of water on resist were pointed out. For example, projection lens contamination and pattern profile changes occur because the acid once generated from a photoacid generator and the amine compound added to the resist as a quencher can be dissolved in water. Inversely, swelling and circular defects known as water marks occur because water can penetrate into the resist film. For overcoming these problems, it was proposed to provide a protective coating between the resist and water (see the 2nd Immersion Workshop, Jul. 11, 2003, Resist and Cover Material Investigation for Immersion Lithography); and to prevent resist materials from dissolution in water or water penetration by controlling the water repellency of resist materials, typically photoacid generators (PAG) or base resins (see J. Photopolymer Sci. and Technol., Vol. 18, No. 5, p 603 (2005)).

DISCLOSURE OF THE INVENTION

An object of the present invention is to provide fluorinated compounds which are useful monomers for the preparation of polymers to be formulated in resist compositions, the resist compositions exhibiting a high resolution and preventing dissolution in immersion media and penetration of immersion media when processed by photolithography using high-energy radiation such as ArF excimer laser radiation as a light source, especially immersion lithography; a method for preparing fluoroalcohol compounds for forming the fluorinated monomers; polymers obtained from the fluorinated monomers; resist compositions comprising the polymers as a base resin; and a patterning process using the resist compositions.

The inventors have found that a fluorine compound of the general formula (1) shown below can be readily converted into a fluoroalcohol compound and further into a fluorinated monomer which is useful as a raw material toward resist material, and that a resist composition comprising a polymer derived from the fluorinated monomer as a base resin exhibits a high resolution and an anti-swelling effect, and prevents dissolution in water as an immersion medium and penetration of water when processed by photolithography, especially immersion lithography so that the polymer is advantageously used in resist form for precise micropatterning.

Accordingly, the present invention provides a method for preparing fluoroalcohol compound, fluorinated monomer, polymer, resist composition, and patterning process, as defined below.

[1] A method for preparing a fluoroalcohol compound having the general formula (4), comprising the step of reacting a fluorine compound having the general formula (1) with reducing agents or organometallic reagents having the general formulas (2) and (3):

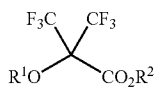
(1)

R$^3$M$^1$ (2)

R$^4$M$^1$ (3)

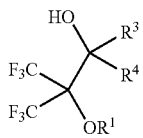
(4)

wherein R$^1$ is hydrogen or a straight, branched or cyclic monovalent hydrocarbon group of 1 to 20 carbon atoms in which any constituent —CH$_2$— moiety may be replaced by —O— or —C(=O)—, R$^2$ is hydrogen or a straight, branched or cyclic monovalent hydrocarbon group of 1 to 6 carbon atoms, R$^3$ and R$^4$ are each independently hydrogen or a straight, branched or cyclic monovalent hydrocarbon group of 1 to 8 carbon atoms, and M$^1$ is at least one element selected from the group consisting of Li, Na, K, Mg, Zn, Al, B, and Si which may be substituted.

[2] A fluorinated monomer having the general formula (5), which is obtained by esterifying the fluoroalcohol compound having the above formula (4),

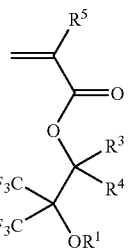
(5)

wherein R$^1$, R$^3$, and R$^4$ are as defined above, and R$^5$ is hydrogen, fluorine, methyl or trifluoromethyl.

[3] A fluorinated monomer having the general formula (6), which is obtained by esterifying the fluoroalcohol compound having the above formula (4),

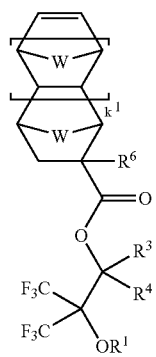
(6)

wherein R$^1$, R$^3$, and R$^4$ are as defined above, R$^6$ is hydrogen, fluorine, methyl or trifluoromethyl, W is —CH$_2$— or —O—, and k$^1$ is 0 or 1.

[4] A method for preparing a fluoroalcohol compound having the general formula (8), comprising the steps of addition reaction of an organometallic reagent having the general formula (7) to a fluorine compound having the above formula (1), and subsequent reducing reaction,

R$^7$M$^2$ (7)

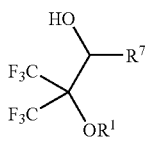
(8)

wherein R$^1$ is as defined above, R$^7$ is a straight, branched or cyclic monovalent hydrocarbon group of 2 to 8 carbon atoms, and M$^2$ is Li, Na, K, MgP or ZnP, wherein P is a halogen atom.

[5] A fluorinated monomer having the general formula (9), which is obtained by esterifying the fluoroalcohol compound having the above formula (8),

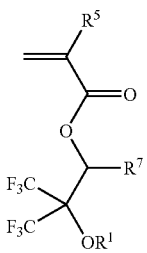

(9)

wherein $R^1$, $R^5$, and $R^7$ are as defined above.

[6] A fluorinated monomer having the general formula (10), which is obtained by esterifying the fluoroalcohol compound having the above formula (8), (10)

wherein $R^1$, $R^6$, $R^7$, W, and $k^1$ are as defined above.

[7] A method for preparing a fluoroalcohol compound having the general formula (12), comprising the step of addition reaction of an organometallic reagent having the general formula (11) to a fluorine compound having the above formula (1), (11)

M²⟨⟩$_{k2}$M²

(12)

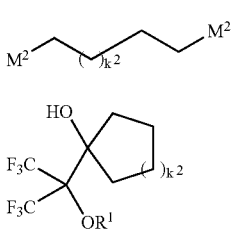

wherein $R^1$ and $M^2$ are as defined above, and $k^2$ is 1 or 2.

[8] A fluorinated monomer having the general formula (13), which is obtained by esterifying the fluoroalcohol compound having the above formula (12), (13)

wherein $R^1$, $R^5$, and $k^2$ are as defined above.

[9] A fluorinated monomer having the general formula (14), which is obtained by esterifying the fluoroalcohol compound having the above formula (12), (14)

wherein $R^1$, $R^6$, W, $k^1$, and $k^2$ are as defined above.

[10] A method for preparing a fluoroalcohol compound having the general formula (16), comprising the step of addition reaction of an organometallic reagent having the general formula (15) to a fluorine compound having the above formula (1), (15)

MeM²

(16)

wherein $R^1$ and $M^2$ are as defined above, and Me is methyl.

[11] A fluorinated monomer having the general formula (17), which is obtained by esterifying the fluoroalcohol compound having the above formula (16),

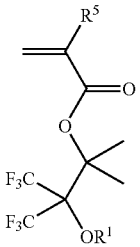
(17)

wherein $R^1$ and $R^5$ are as defined above.

[12] A fluorinated monomer having the general formula (18), which is obtained by esterifying the fluoroalcohol compound having the above formula (16),

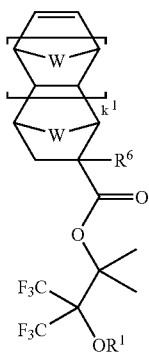
(18)

wherein $R^1$, $R^6$, W, and $k^1$ are as defined above.

[13] A polymer comprising recurring units derived from the fluorinated monomer of any one of [2], [3], [5], [6], [8], [9], [11] and [12].

[14] A polymer comprising recurring units having any one of the general formulas (1a) to (1c):

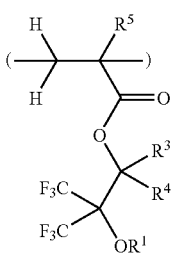
(1a)

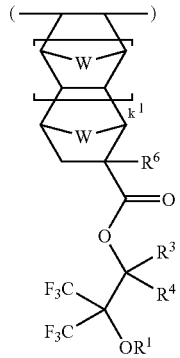
(1b)

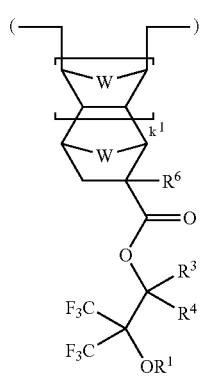
(1c)

wherein $R^1$, $R^3$ to $R^6$, W, and $k^1$ are as defined above.

[15] A polymer comprising recurring units having any one of the general formulas (2a) to (2c):

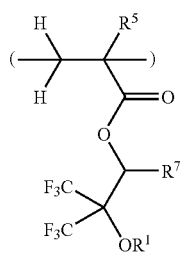
(2a)

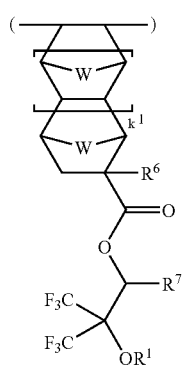
(2b)

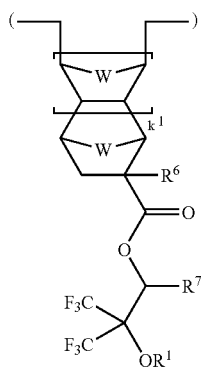
(2c)

wherein $R^1$, $R^5$ to $R^7$, W, and $k^1$ are as defined above.

[16] A polymer comprising recurring units having any one of the general formulas (3a) to (3c):

(3a)

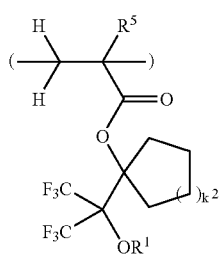

(3b)

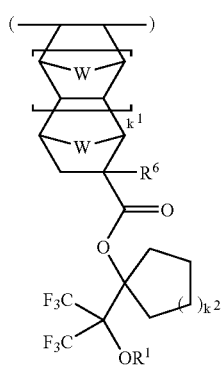

(3c)

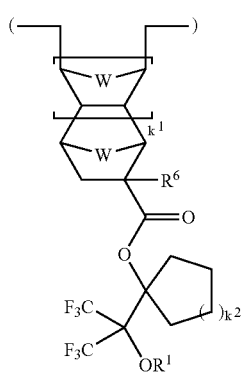

wherein $R^1$, $R^5$, $R^6$, W, $k^1$, and $k^2$ are as defined above.

[17] A polymer comprising recurring units having any one of the general formulas (4a) to (4c):

(4a)

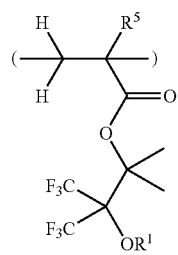

(4b)

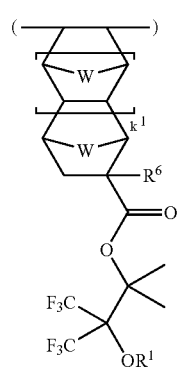

(4c)

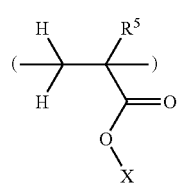

wherein $R^1$, $R^5$, $R^6$, W, and $k^1$ are as defined above.

[18] The polymer of any one of [13] to [17], comprising recurring units of at least one type selected from the general formulas (19) to (22):

(19)

-continued

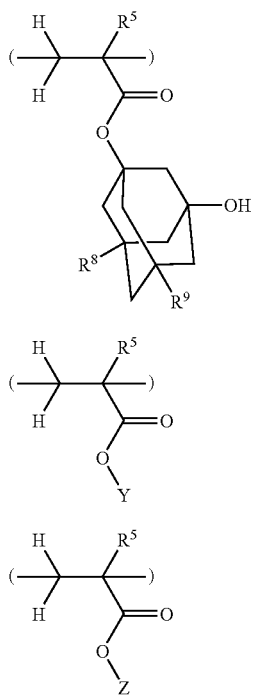

wherein $R^5$ is as defined above, $R^8$ and $R^9$ are each independently hydrogen or hydroxyl, X is an acid labile group, Y is a substituent group having a lactone structure, and Z is hydrogen, a fluoroalkyl group of 1 to 15 carbon atoms, or a fluoroalcohol-containing substituent group of 1 to 15 carbon atoms.

[19] A resist composition comprising the polymer of any one of [13] to [18] as a base resin.

[20] A pattern forming process comprising the steps of applying the resist composition of [19] onto a substrate to form a coating; heat treating the coating and exposing it to high-energy radiation or electron beam through a photomask; optionally heat treating the exposed coating, and developing it with a developer.

BENEFITS OF THE INVENTION

The fluorinated monomers of the invention are useful as raw materials for the synthesis of polymers, functional materials, pharmaceutical and agricultural chemicals. They are most useful as monomers to produce polymers for the manufacture of radiation-sensitive resist compositions which have high transparency to radiation having a wavelength of up to 500 nm, especially up to 300 nm, and exhibit good development characteristics. With the method of the invention, the fluorinated monomers can be readily produced at low cost. Radiation-sensitive resist compositions comprising the polymers as base resin exhibit high resolution and an anti-swelling effect, and prevent dissolution in water as an immersion medium and penetration of water when processed by photolithography, especially immersion lithography. The polymers are advantageously used in resist form for precise micropatterning.

DESCRIPTION OF THE PREFERRED EMBODIMENTS

Compound and Method

The first aspect of the invention relates to a method for preparing a fluoroalcohol compound. The method comprises the step of reacting a fluorine compound having the general formula (1) with reducing agents or organometallic reagents having the general formulas (2) and (3) to form a fluoroalcohol compound having the general formula (4).

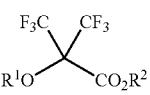

(1)

$R^3M^1$ (2)

$R^4M^1$ (3)

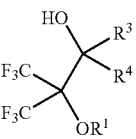

(4)

Herein $R^1$ is hydrogen or a straight, branched or cyclic monovalent hydrocarbon group of 1 to 20 carbon atoms, in the case of a monovalent hydrocarbon group, any —$CH_2$— moiety contained therein may be replaced by —O— or —C(=O)—; $R^2$ is hydrogen or a straight, branched or cyclic monovalent hydrocarbon group of 1 to 6 carbon atoms; $R^3$ and $R^4$ are each independently hydrogen or a straight, branched or cyclic monovalent hydrocarbon group of 1 to 8 carbon atoms; and $M^1$ is at least one element selected from the group consisting of Li, Na, K, Mg, Zn, Al, B, and Si which may be substituted.

The fluorine compound of formula (1), specifically 3,3,3-trifluoro-2-trifluoromethyl-2-hydroxypropionic acid derivative is obtained from a source material, for example, octafluoroisobutylene formed as by-product during synthesis of hexafluoropropene or the like. A large amount of the fluorine compound is available at a relatively low cost because the feed source originates as a by-product of commercial product synthesis.

The monovalent hydrocarbon groups represented by $R^1$ include a variety of protective groups for alcoholic hydroxyl groups. Suitable hydrocarbon groups include groups of the following general formulae (R1-1) and (R1-2), tertiary alkyl groups of 4 to 15 carbon atoms, trialkylsilyl groups in which each alkyl moiety has 1 to 5 carbon atoms, oxoalkyl groups of 4 to 15 carbon atoms, and acyl groups of 1 to 10 carbon atoms.

(R1-1)

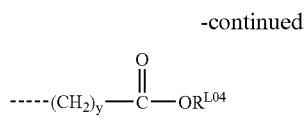
(R1-2)

In these formulae and throughout the specification, the broken line denotes a valence bond. $R^{L01}$ and $R^{L02}$ are hydrogen or straight, branched or cyclic alkyl groups of 1 to 18 carbon atoms, preferably 1 to 10 carbon atoms. Exemplary alkyl groups include methyl, ethyl, propyl, isopropyl, n-butyl, sec-butyl, tert-butyl, cyclopentyl, cyclohexyl, 2-ethylhexyl, n-octyl, norbornyl, tricyclodecanyl, tetracyclododecanyl, and adamantyl. $R^{L03}$ is a monovalent hydrocarbon group of 1 to 18 carbon atoms, preferably 1 to 10 carbon atoms, which may contain a hetero atom such as oxygen, examples of which include unsubstituted straight, branched or cyclic alkyl groups and substituted forms of such alkyl groups in which some hydrogen atoms are replaced by hydroxyl, alkoxy, oxo, amino, alkylamino or the like. Illustrative examples are the substituted alkyl groups shown below.

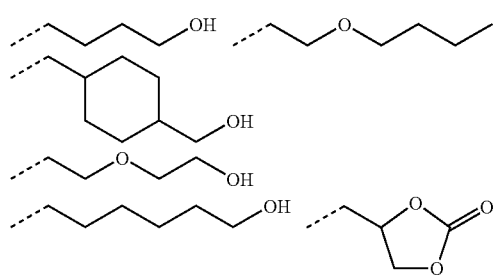

A pair of $R^{L01}$ and $R^{L02}$, $R^{L01}$ and $R^{L03}$, or $R^{L02}$ and $R^{L03}$ may bond together to form a ring with carbon and oxygen atoms to which they are attached. Each of $R^{L01}$, $R^{L02}$ and $R^{L03}$ is a straight or branched alkylene group of 1 to 18 carbon atoms, preferably 1 to 10 carbon atoms when they form a ring.

$R^{L04}$ is a tertiary alkyl group of 4 to 20 carbon atoms, preferably 4 to 15 carbon atoms, a trialkylsilyl group in which each alkyl moiety has 1 to 6 carbon atoms, an oxoalkyl group of 4 to 20 carbon atoms, or a group of formula (R1-1).

Exemplary tertiary alkyl groups are tert-butyl, tert-amyl, 1,1-diethylpropyl, 2-cyclopentylpropan-2-yl, 2-cyclohexylpropan-2-yl, 2-(bicyclo[2.2.1]heptan-2-yl)propan-2-yl, 2-(adamantan-1-yl)propan-2-yl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, and 2-ethyl-2-adamantyl. Exemplary trialkylsilyl groups are trimethylsilyl, triethylsilyl, and dimethyl-tert-butylsilyl. Exemplary oxoalkyl groups are 3-oxocyclohexyl, 4-methyl-2-oxooxan-4-yl, and 5-methyl-2-oxooxolan-5-yl. Exemplary acyl groups include formyl, acetyl, ethylcarbonyl, pivaloyl, methoxycarbonyl, ethoxycarbonyl, tert-butoxycarbonyl, trifluoroacetyl, and trichloroacetyl. Letter y is an integer of 0 to 6.

Of the protective groups of formula (R1-1), the straight and branched ones are exemplified by the following groups.

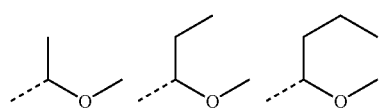
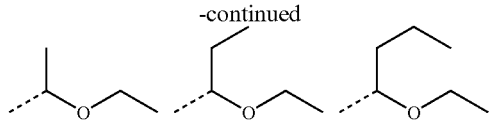
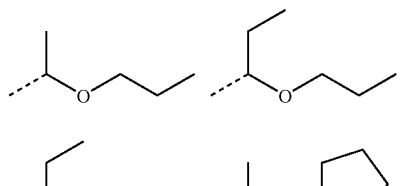
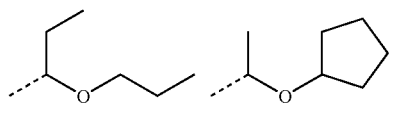
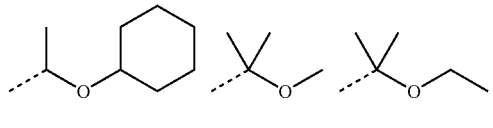
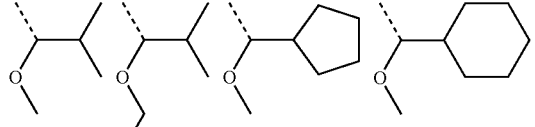
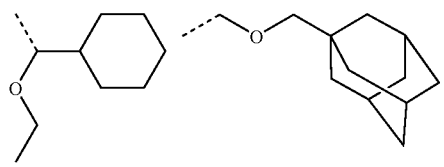
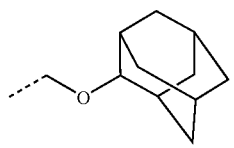

Of the protective groups of formula (R1-1), the cyclic ones are, for example, tetrahydrofuran-2-yl, 2-methyltetrahydrofuran-2-yl, tetrahydropyran-2-yl, and 2-methyltetrahydropyran-2-yl.

Examples of the protective groups of formula (R1-2) include tert-butoxycarbonyl, tert-butoxycarbonylmethyl, tert-amyloxycarbonyl, tert-amyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl groups.

Examples of $R^2$ include hydrogen, methyl, ethyl, n-propyl, isopropyl, n-butyl, sec-butyl, tert-butyl, cyclopentyl, and cyclohexyl.

Examples of straight, branched or cyclic monovalent hydrocarbon groups of 1 to 8 carbon atoms represented by $R^3$ and $R^4$ include methyl, ethyl, n-propyl, isopropyl, n-butyl, sec-butyl, isobutyl, tert-butyl, cyclopentyl, cyclohexyl, 2-ethylhexyl, and n-octyl. $R^3$ and $R^4$ may be the same or different.

Illustrative examples of the reducing agents or organometallic reagents (2) and (3) which can be used herein include complex hydrides such as sodium boron hydride, lithium boron hydride, potassium boron hydride, calcium boron hydride, sodium aluminum hydride, lithium aluminum hydride, lithium triethylboron hydride, lithium tri-s-butylboron hydride, and potassium tri-s-butylboron hydride, and alkoxy or alkyl derivatives thereof; organolithium reagents such as methyllithium and n-butyllithium; Grignard reagents such as methyl magnesium chloride, ethyl magnesium chloride, and isopropyl magnesium chloride; organozinc reagents such as dimethylzinc; and triethylsilane and the like.

The amounts of the reducing agents or organometallic reagents (2) and (3) used vary over a wide range with conditions. In the case of a fluorine compound of formula (1) wherein $R^1$ is hydrogen, for example, the reducing agent is desirably used in an amount of 2.0 to 5.0 moles, more desirably 2.0 to 3.0 moles per mole of fluorine compound (1). Suitable solvents include ethers such as tetrahydrofuran, diethyl ether, di-n-butyl ether and 1,4-dioxane, hydrocarbons such as n-hexane, n-heptane, benzene, toluene, xylene and cumene, alcohols such as methanol, ethanol, isopropyl alcohol and tert-butyl alcohol, and aprotic polar solvents such as dimethylsulfoxide (DMSO), N,N-dimethylformamide (DMF) and acetonitrile. These solvents may be used alone or in admixture. The reaction temperature and time vary with other conditions. Where a Grignard reagent (corresponding to formula (2) or (3) wherein $M^1$ is MgP wherein P is halogen) is used as the organometallic reagent, for example, the reaction may be conducted at a temperature of 0 to 100° C., preferably 20 to 70° C. It is desired for higher yields that the reaction be driven to completion by monitoring the progress of reaction by gas chromatography (GC) or silica gel thin-layer chromatography (TLC). The reaction time is usually about 0.5 hour to about 10 hours. The fluoroalcohol compound (4) may be recovered from the reaction mixture by ordinary aqueous work-up. If necessary, the fluoroalcohol compound (4) can be purified by any standard technique such as distillation or recrystallization.

The first fluorinated monomer of the invention is a compound having the general formula (5), which is obtained through esterification of the fluoroalcohol compound having formula (4).

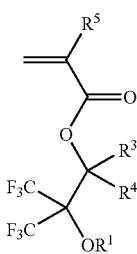

(5)

Herein $R^1$, $R^3$, and $R^4$ are as defined above, and $R^5$ is a hydrogen atom, fluorine atom, methyl group or trifluoromethyl group.

The fluorinated monomer of formula (5) is obtained by esterifying the fluoroalcohol compound of formula (4) with an esterifying agent of formula (23) according to the following reaction scheme.

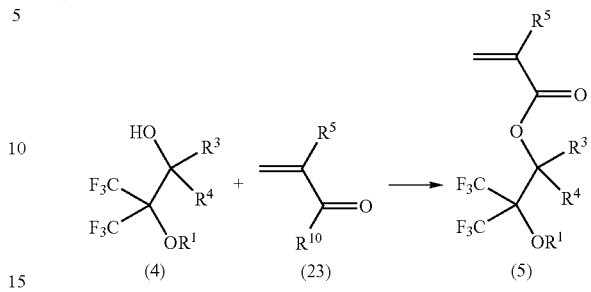

Herein $R^1$, $R^3$ to $R^5$ are as defined above, and $R^{10}$ is a halogen atom or —$OR^{11}$ wherein $R^{11}$ is hydrogen, —C(=O)$R^5C$=$CH_2$, methyl or ethyl.

The esterification reaction takes place readily by a well-known technique. The esterifying agent (23) used herein is preferably an acid chloride (corresponding to formula (23) wherein $R^{10}$ is chlorine), a carboxylic acid (corresponding to formula (23) wherein $R^{10}$ is —$OR^{11}$ wherein $R^{11}$ is hydrogen), or an acid anhydride (corresponding to formula (23) wherein $R^{10}$ is —$OR^{11}$ wherein $R^{11}$ is —C(=O)$R^5C$=$CH_2$ or the like). Where an acid chloride is used, the reaction may be conducted in a solventless system or in a solvent such as methylene chloride, toluene or hexane, by sequentially or simultaneously adding the alcohol (4), the acid chloride (e.g., methacrylic acid chloride or α-trifluoromethylacrylic acid chloride), and a base (e.g., triethylamine, pyridine or 4-dimethylaminopyridine), and allowing the reaction to take place while cooling or heating if necessary. Where a carboxylic acid is used, the reaction may be conducted in a solvent such as toluene or hexane, by adding the alcohol (4), the carboxylic acid (e.g., methacrylic acid or α-trifluoromethylacrylic acid), a mineral acid (e.g., hydrochloric acid, sulfuric acid, nitric acid or perchloric acid), and an organic acid (e.g., p-toluenesulfonic acid, benzenesulfonic acid or trifluoroacetic acid), heating the system, and removing the water resulting from reaction out of the system, if necessary; or in a solventless system or in a solvent such as toluene or hexane, by sequentially or simultaneously adding the alcohol (4), an aliphatic sulfonyl chloride (e.g., methane sulfonyl chloride), an aromatic sulfonyl chloride (e.g., p-toluenesulfonic acid chloride), and an acid anhydride (e.g., acetic anhydride or trifluoroacetic anhydride), and optionally, a base (e.g., triethylamine, pyridine or 4-dimethylaminopyridine), and allowing the reaction to take place while cooling or heating if necessary. Where an acid anhydride is used, the reaction may be conducted in a solventless system or in a solvent such as methylene chloride, toluene or hexane, by sequentially or simultaneously adding the alcohol (4), the acid anhydride (e.g., methacrylic acid anhydride or α-trifluoromethylacrylic acid anhydride), a mineral acid (e.g., hydrochloric acid, sulfuric acid, nitric acid or perchloric acid), and an organic acid (e.g., p-toluenesulfonic acid, benzenesulfonic acid or trifluoroacetic acid), or a base (e.g., triethylamine, pyridine or 4-dimethylaminopyridine), and allowing the reaction to take place while cooling or heating if necessary.

It is understood that the acid anhydride used herein may be a mixture of acid anhydride with another acid examples of which include carboxylic acids such as formic acid, acetic acid and trifluoroacetic acid, sulfonic acids such as methanesulfonic acid and p-toluenesulfonic acid, and phenols such as phenol and p-nitrophenol.

A fluorinated monomer of formula (5) wherein $R^1$ is hydrogen can be produced by using a corresponding fluoroalcohol compound of formula (4) wherein $R^1$ is hydrogen, and subjecting the hydroxyl group on the desired side to selective mono-esterification. Alternatively, the desired compound (5) can be produced by esterifying both the hydroxyl groups on the fluoroalcohol compound of formula (4) to form a diester compound having the general formula (24), shown below, and effecting deprotection such as hydrolytic reaction.

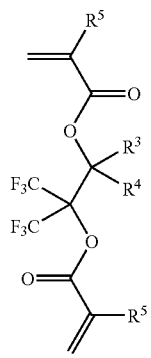

(24)

Herein, $R^3$ to $R^5$ are as defined above.

Illustrative, non-limiting examples of the compound of formula (5) are given below.

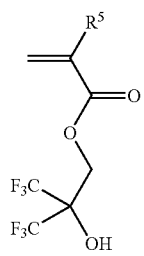 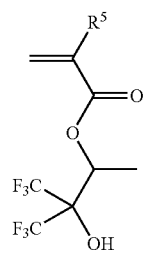 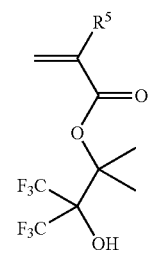

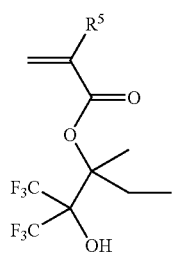 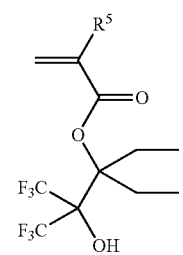

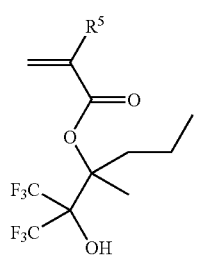 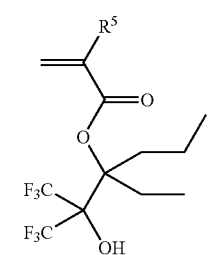

-continued

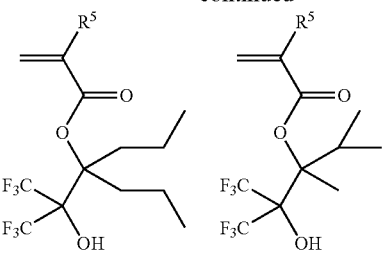 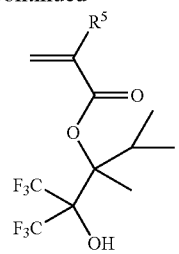

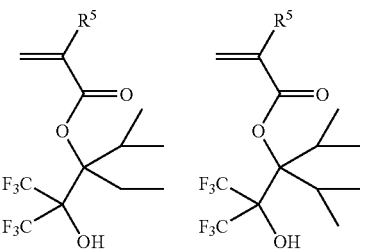 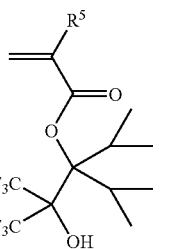

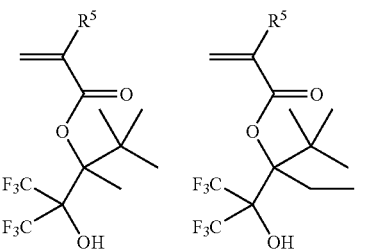 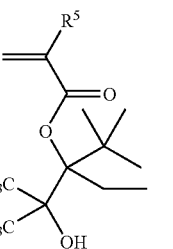

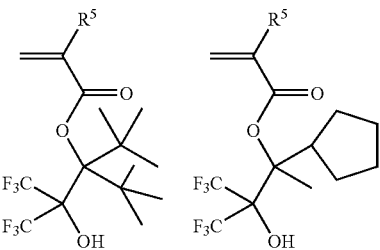 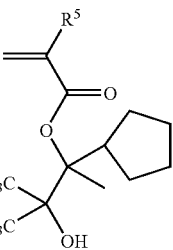

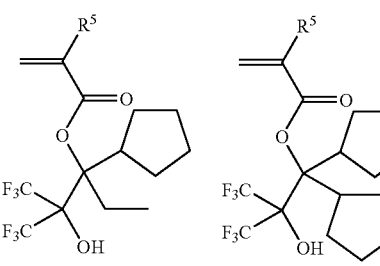 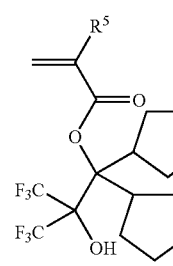

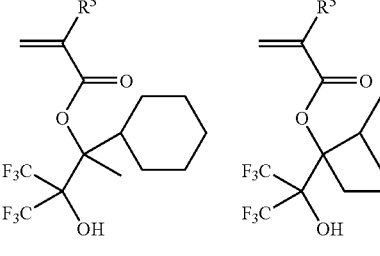 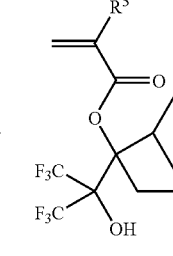

Herein, $R^5$ is as defined above.

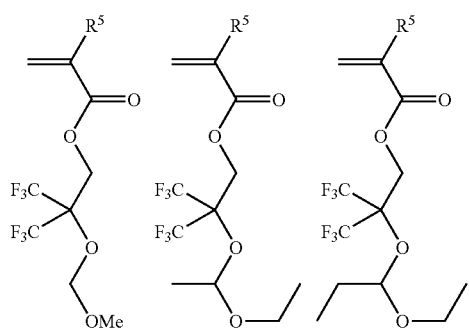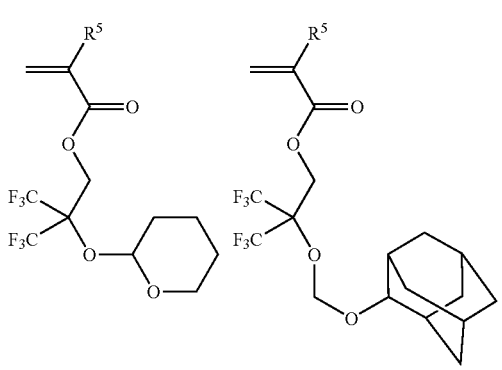
-continued
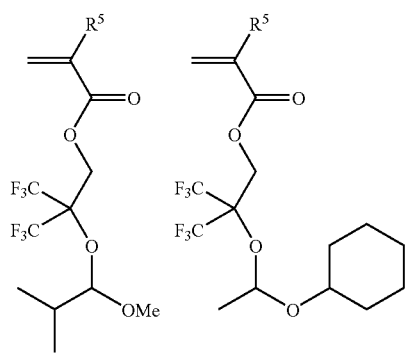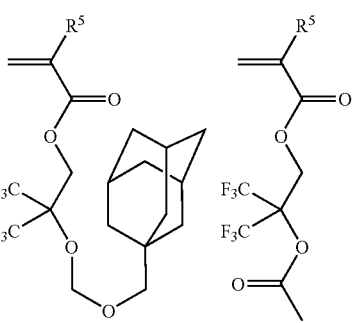
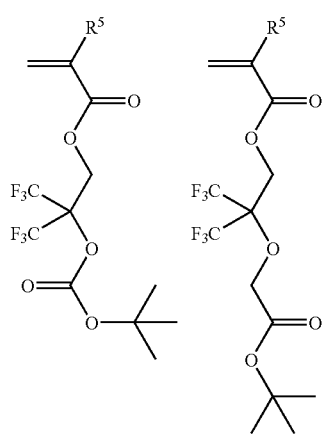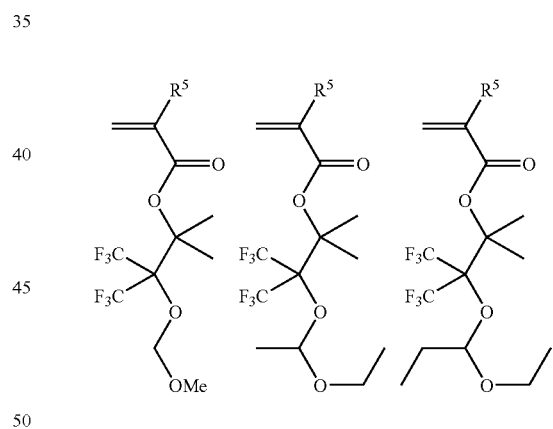
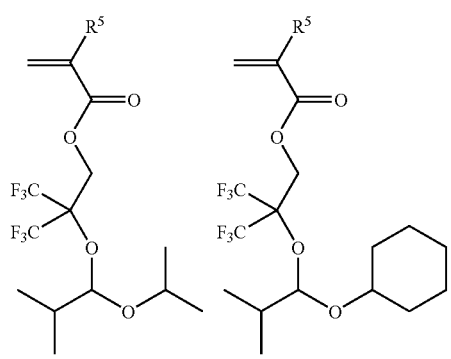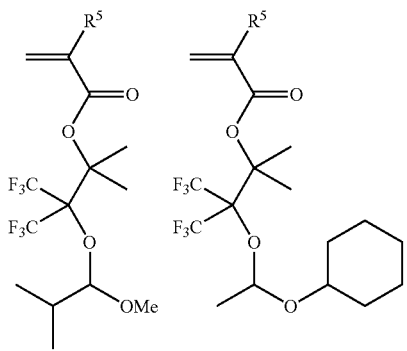

-continued

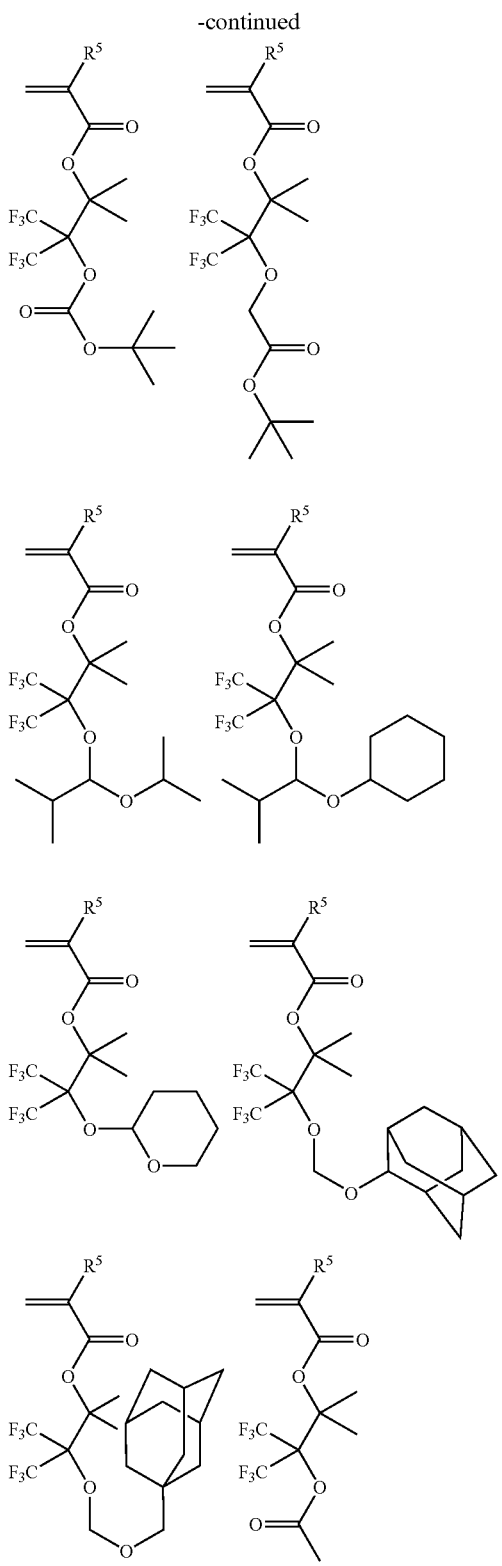

Herein, R⁵ is as defined above and Me is methyl.

The second fluorinated monomer of the invention is a compound having the general formula (6), which is obtained through esterification of the fluoroalcohol compound having formula (4).

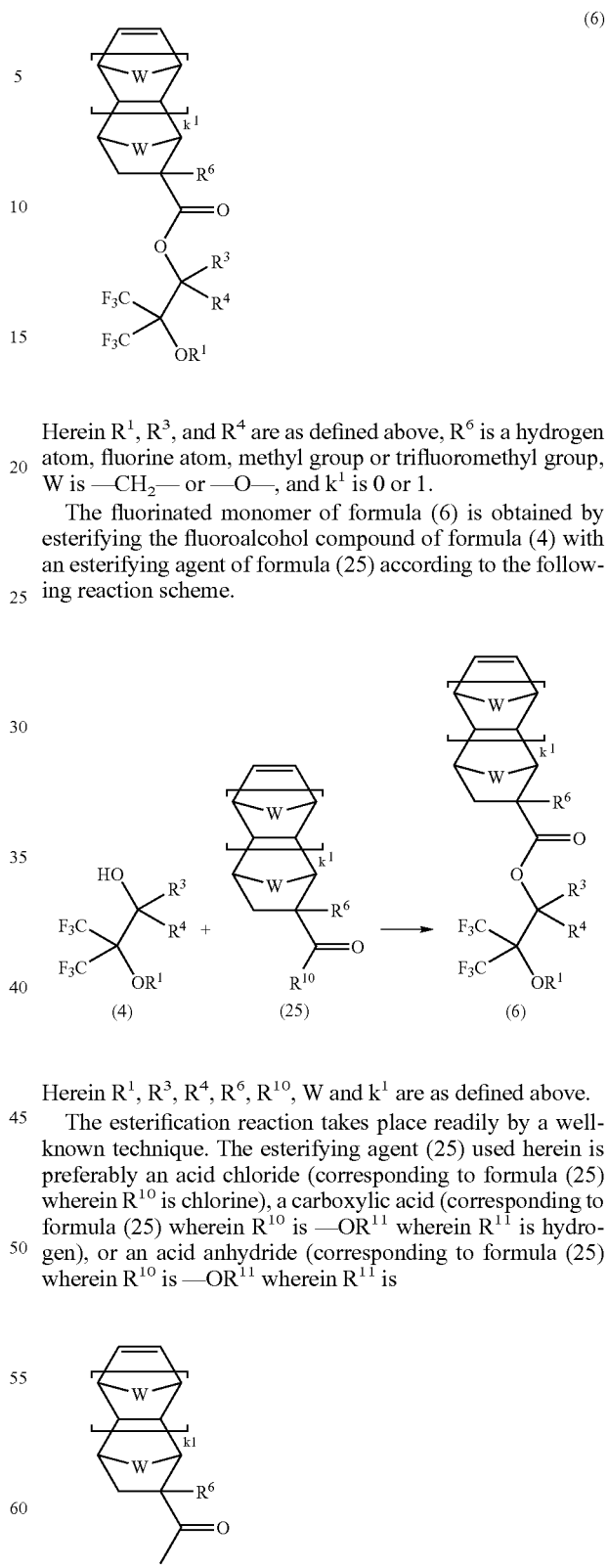

Herein $R^1$, $R^3$, and $R^4$ are as defined above, $R^6$ is a hydrogen atom, fluorine atom, methyl group or trifluoromethyl group, W is —CH$_2$— or —O—, and $k^1$ is 0 or 1.

The fluorinated monomer of formula (6) is obtained by esterifying the fluoroalcohol compound of formula (4) with an esterifying agent of formula (25) according to the following reaction scheme.

Herein $R^1$, $R^3$, $R^4$, $R^6$, $R^{10}$, W and $k^1$ are as defined above.

The esterification reaction takes place readily by a well-known technique. The esterifying agent (25) used herein is preferably an acid chloride (corresponding to formula (25) wherein $R^{10}$ is chlorine), a carboxylic acid (corresponding to formula (25) wherein $R^{10}$ is —OR$^{11}$ wherein $R^{11}$ is hydrogen), or an acid anhydride (corresponding to formula (25) wherein $R^{10}$ is —OR$^{11}$ wherein $R^{11}$ is

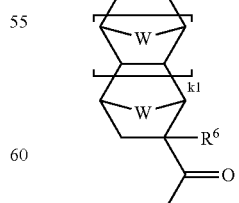

or the like). Where an acid chloride is used, the reaction may be conducted in a solventless system or in a solvent such as methylene chloride, toluene or hexane, by sequentially or simultaneously adding the alcohol (4), the acid chloride (e.g., 5-norbornene-2-carboxylic acid chloride or 7-oxa-5-norbornene-2-carboxylic acid chloride), and a base (e.g., triethylamine, pyridine or 4-dimethylaminopyridine), and allowing the reaction to take place while cooling or heating if necessary. Where a carboxylic acid is used, the reaction may be conducted in a solvent such as toluene or hexane, by adding the alcohol (4), the carboxylic acid (e.g., 5-norbornene-2-carboxylic acid or 7-oxa-5-norbornene-2-carboxylic acid), a mineral acid (e.g., hydrochloric acid, sulfuric acid, nitric acid or perchloric acid), and an organic acid (e.g., p-toluenesulfonic acid, benzenesulfonic acid or trifluoroacetic acid), heating the system, and removing the water resulting from reaction out of the system, if necessary; or in a solventless system or in a solvent such as toluene or hexane, by sequentially or simultaneously adding the alcohol (4), an aliphatic sulfonyl chloride (e.g., methane sulfonyl chloride), an aromatic sulfonyl chloride (e.g., p-toluenesulfonic acid chloride), and an acid anhydride (e.g., acetic anhydride or trifluoroacetic anhydride), and optionally, a base (e.g., triethylamine, pyridine or 4-dimethylaminopyridine), and allowing the reaction to take place while cooling or heating if necessary. Where an acid anhydride is used, the reaction may be conducted in a solventless system or in a solvent such as methylene chloride, toluene or hexane, by sequentially or simultaneously adding the alcohol (4), the acid anhydride (e.g., norbornenecarboxylic acid anhydride or tetracyclododecenecarboxylic acid anhydride), a mineral acid (e.g., hydrochloric acid, sulfuric acid, nitric acid or perchloric acid), and an organic acid (e.g., p-toluenesulfonic acid, benzenesulfonic acid or trifluoroacetic acid), or a base (e.g., triethylamine, pyridine or 4-dimethylaminopyridine), and allowing the reaction to take place while cooling or heating if necessary.

It is understood that the acid anhydride used herein may be a mixture of acid anhydride with another acid, examples of which include carboxylic acids such as formic acid, acetic acid and trifluoroacetic acid, sulfonic acids such as methanesulfonic acid and p-toluenesulfonic acid, and phenols such as phenol and p-nitrophenol.

The desired compound (6) may also be derived through Diels-Alder reaction of the fluorinated monomer (5) with furan or a corresponding diene compound such as cyclopentadiene.

Illustrative, non-limiting examples of the compound of formula (6) are given below.

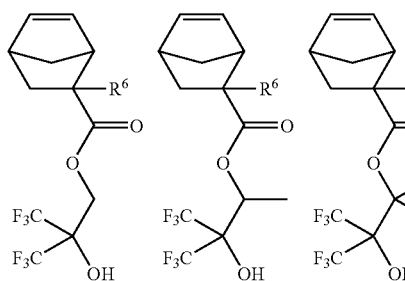

-continued

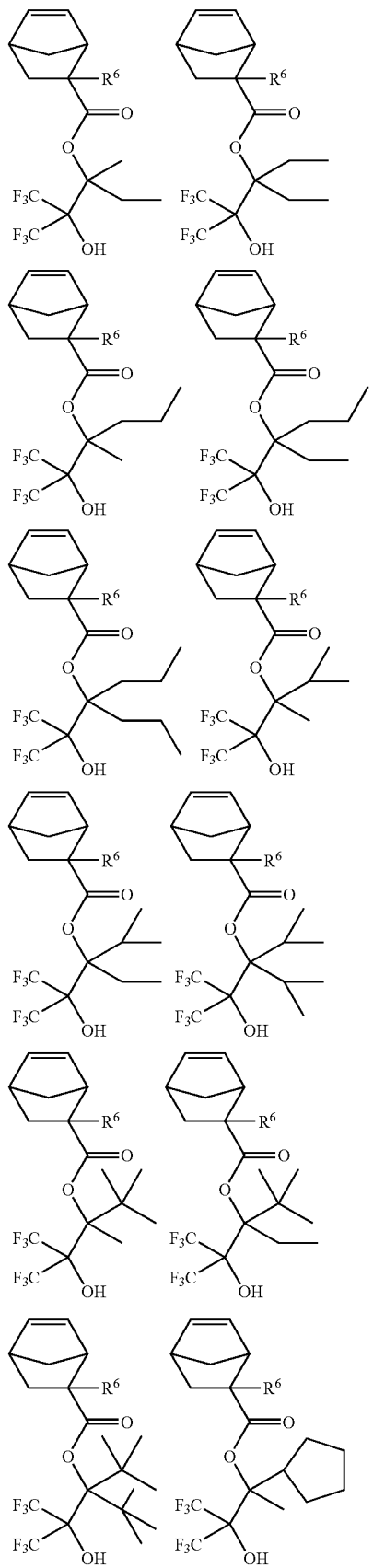

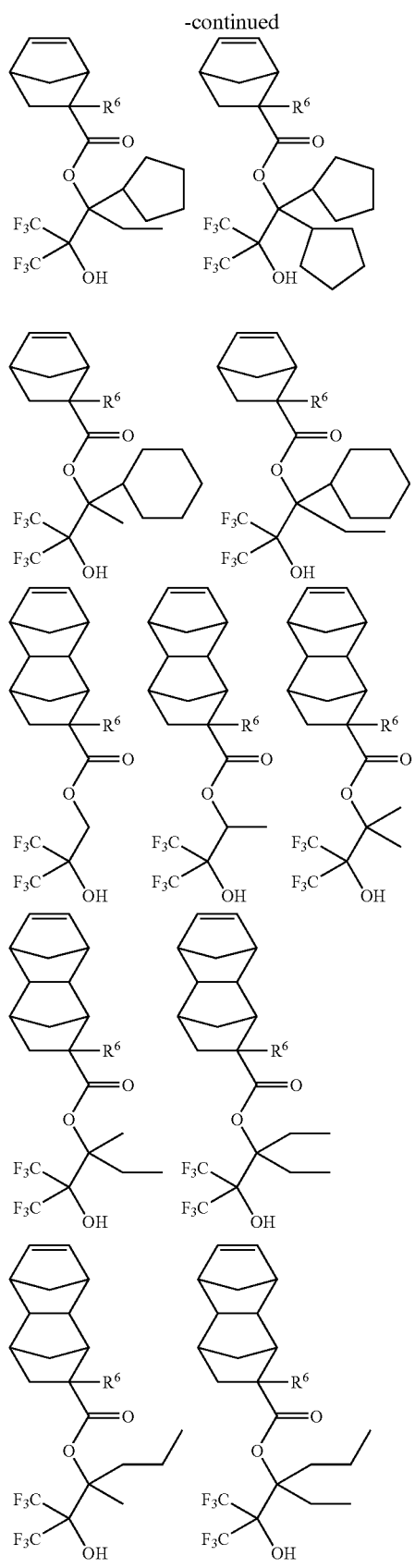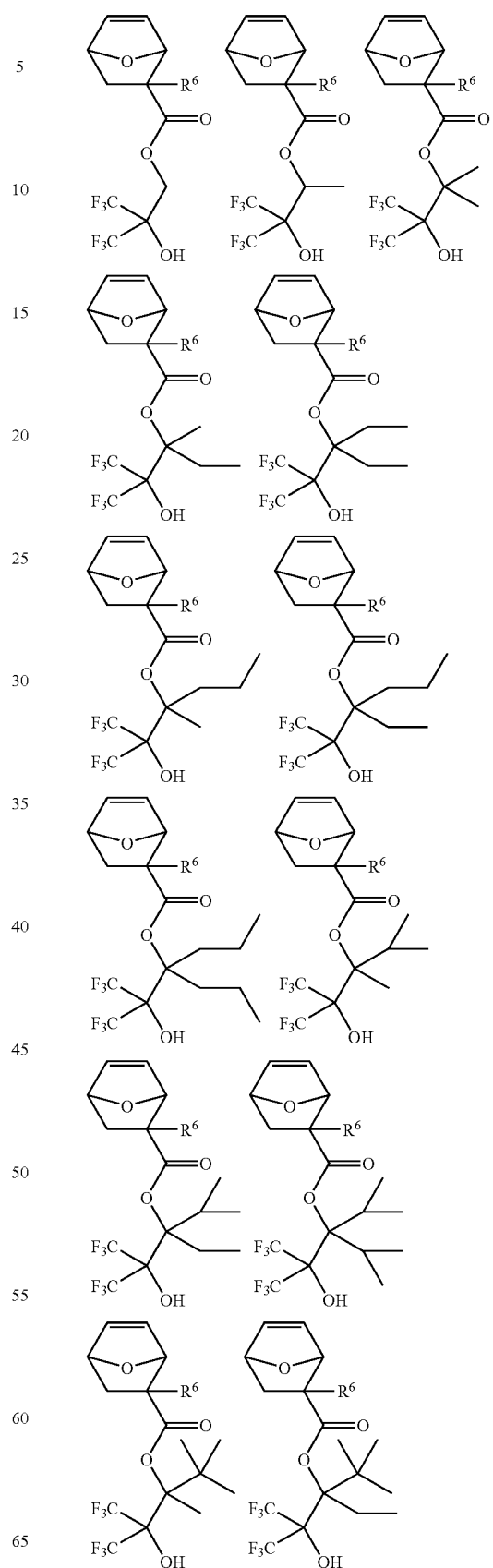
Herein, R⁶ is as defined above.

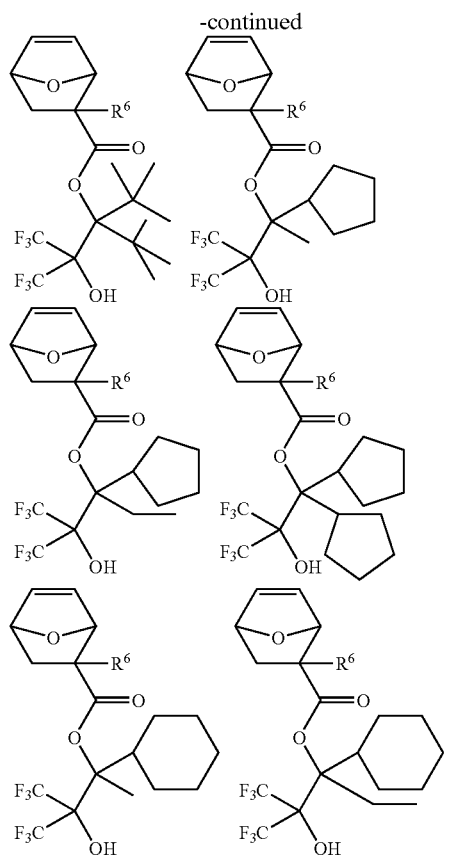
Herein, R⁶ is as defined above.
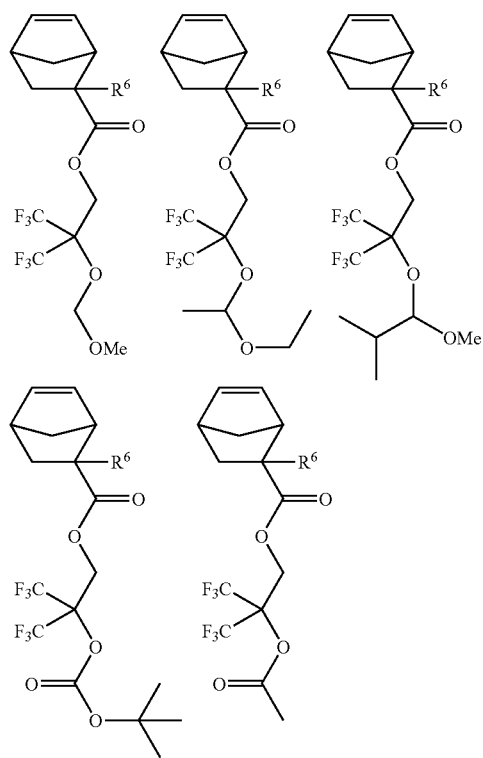
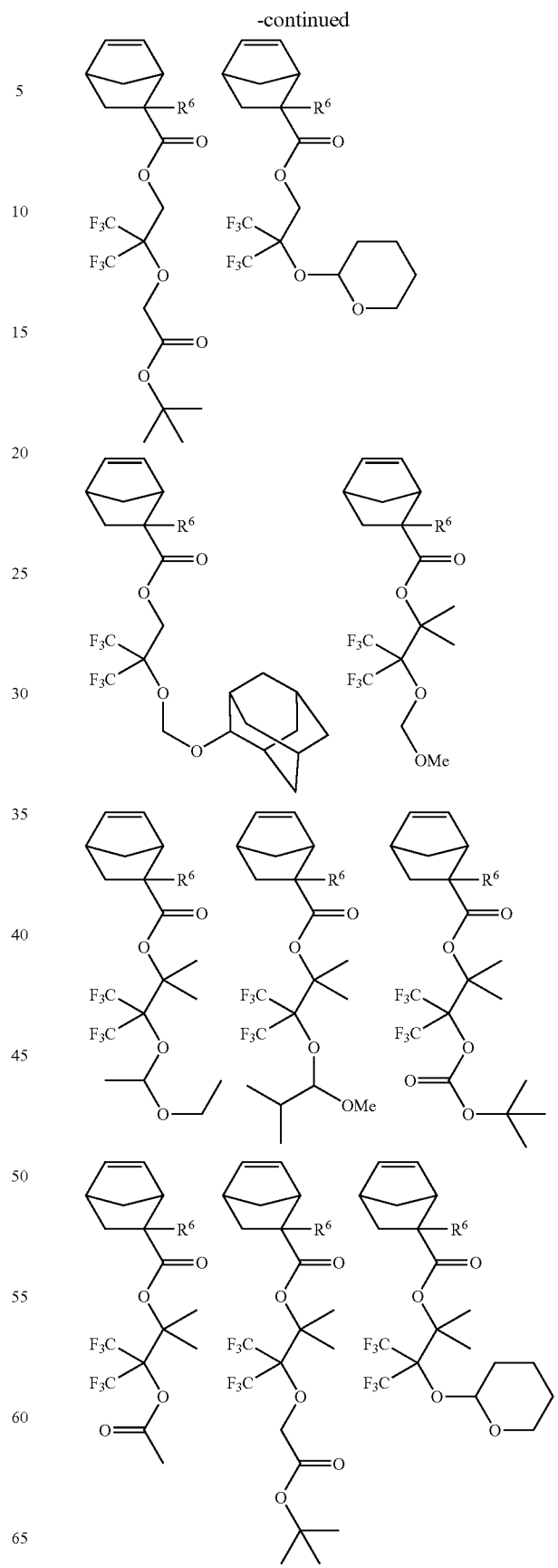

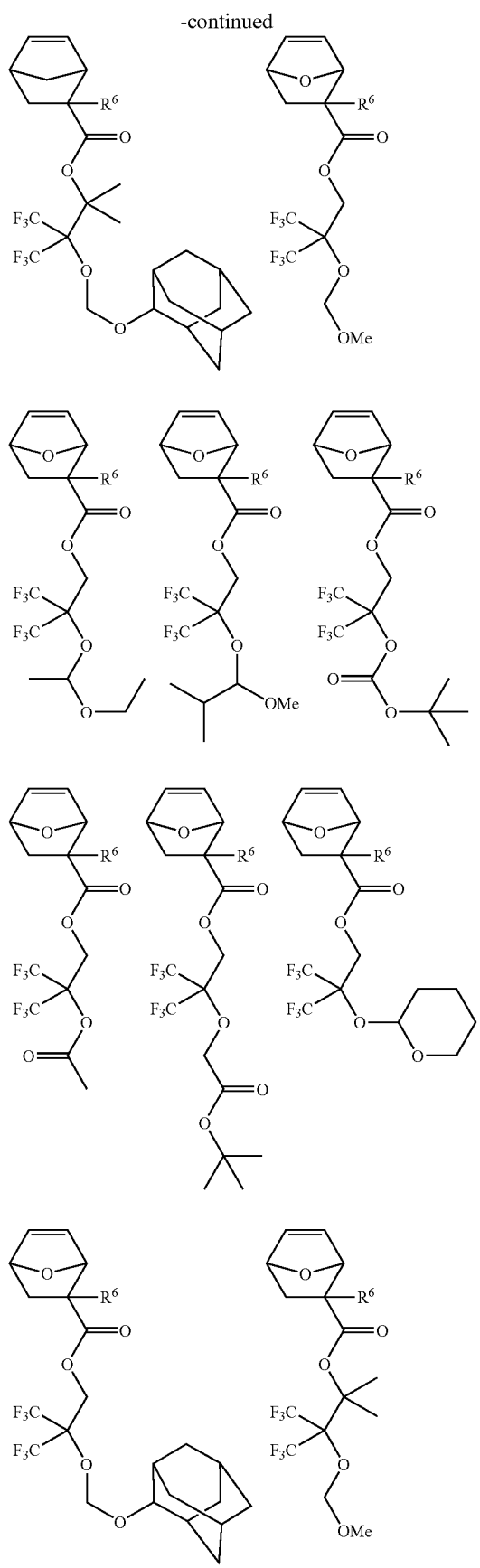
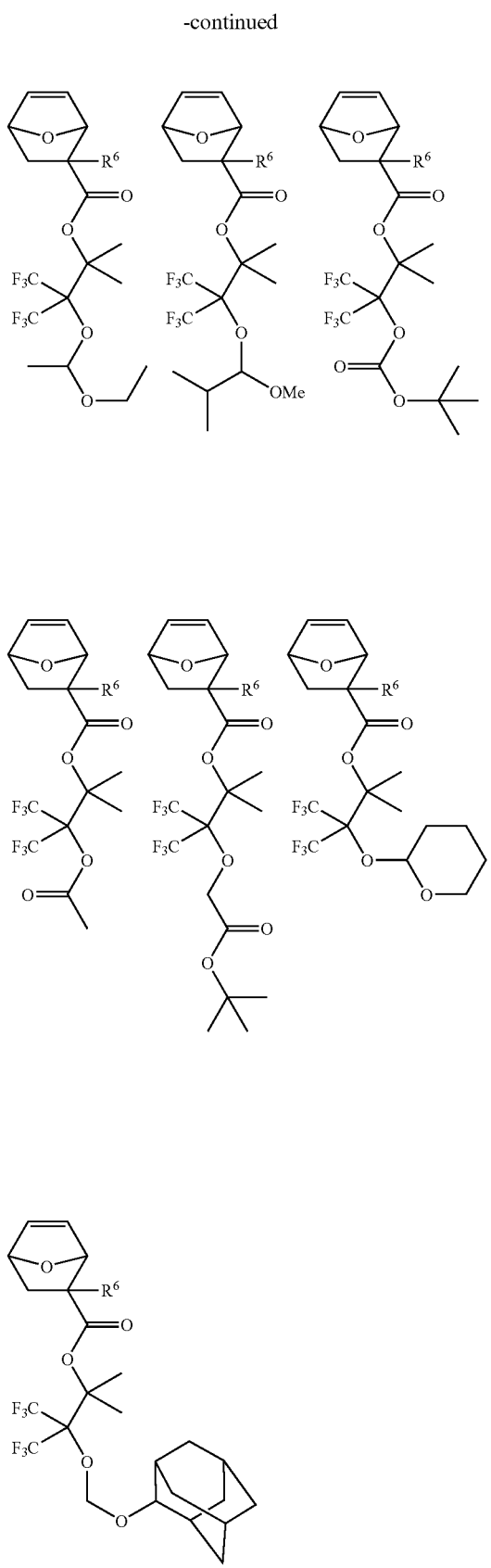
Herein, $R^6$ is as defined above, and Me is methyl.

31
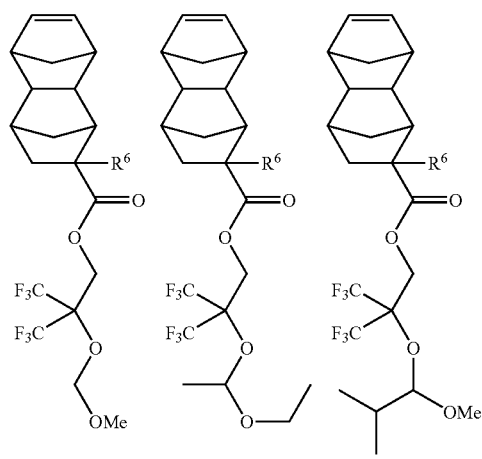
32
-continued
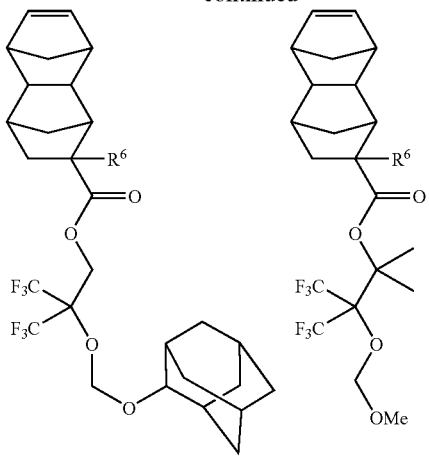
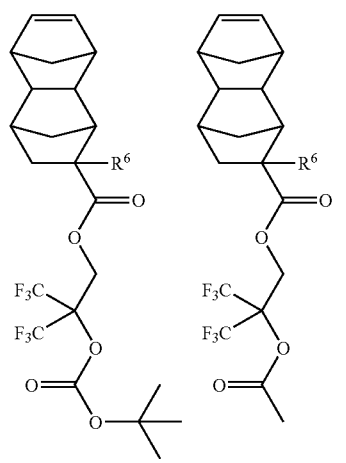
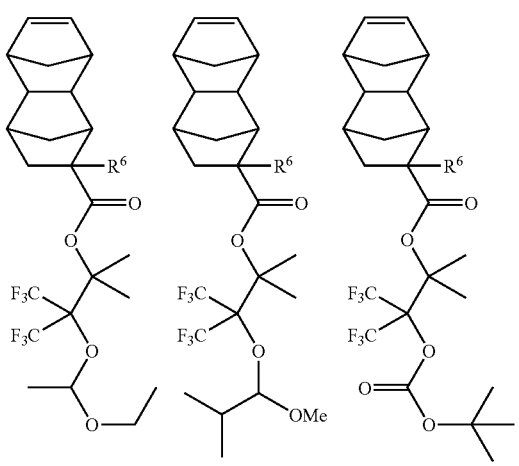
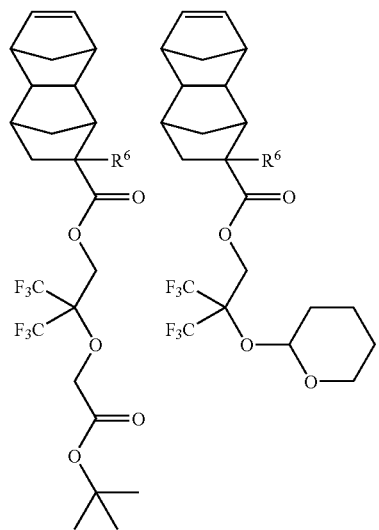
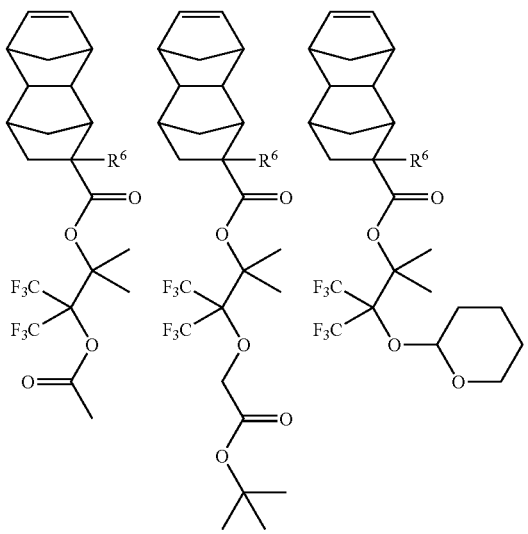

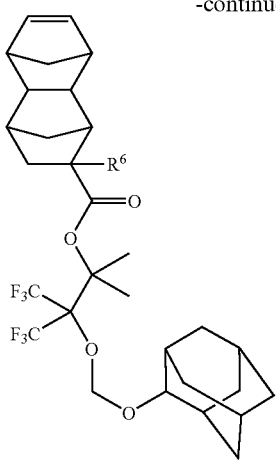

Herein, $R^6$ is as defined above, and Me is methyl.

The second aspect of the invention also relates to a method for preparing a fluoroalcohol compound. The method comprises the steps of addition reaction of an organometallic reagent having the general formula (7) to a fluorine compound having the general formula (1), and subsequent reducing reaction, for thereby forming a fluoroalcohol compound having the general formula (8).

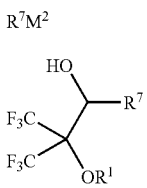

(7)

(8)

Herein $R^1$ is as defined above, $R^7$ is a straight, branched or cyclic monovalent hydrocarbon group of 2 to 8 carbon atoms, and $M^2$ is Li, Na, K, MgP or ZnP, wherein P is a halogen atom.

The first stage is nucleophilic addition reaction of $R^7M^2$ to the ester carbonyl group on compound (1) to introduce $R^7$, and the second stage is reducing reaction of $R^7M^2$ with β-hydride to introduce hydride. The first stage is followed by the second stage, yielding the compound (8).

Examples of hydrocarbon groups represented by $R^7$ include ethyl, n-propyl, isopropyl, n-butyl, sec-butyl, isobutyl, tert-butyl, cyclopentyl, cyclohexyl, 2-ethylhexyl, and n-octyl. Inter alia, secondary alkyl groups such as isopropyl, sec-butyl, isobutyl, cyclopentyl and cyclohexyl and tertiary alkyl groups such as tert-butyl are preferred because of an easier progress of reducing reaction with β-hydride at the second stage. Most preferably $M^2$ is MgP.

The amount of the organometallic reagent (7) used varies over a wide range with conditions. In the case of a fluorine compound of formula (1) wherein $R^1$ is hydrogen, for example, the reagent is desirably used in an amount of 2.0 to 5.0 moles, more desirably 2.0 to 3.0 moles per mole of fluorine compound (1). Suitable solvents include ethers such as tetrahydrofuran, diethyl ether, di-n-butyl ether and 1,4-dioxane, and hydrocarbons such as n-hexane, n-heptane, benzene, toluene, xylene and cumene. These solvents may be used alone or in admixture. The reaction temperature and time vary with other conditions. Where a Grignard reagent (corresponding to formula (7) wherein $M^2$ is MgP wherein P is halogen) is used as the organometallic reagent, for example, the reaction may be conducted at a temperature of 0 to 100° C., preferably 20 to 70° C. It is desired for higher yields that the reaction be driven to completion by monitoring the progress of reaction by gas chromatography (GC) or silica gel thin-layer chromatography (TLC). The reaction time is usually about 0.5 hour to about 10 hours. The fluoroalcohol compound (8) may be recovered from the reaction mixture by ordinary aqueous work-up. If necessary, the fluoroalcohol compound (8) can be purified by any standard technique such as distillation or recrystallization.

The third fluorinated monomer of the invention is a compound having the general formula (9), which is obtained through esterification of the fluoroalcohol compound having formula (8).

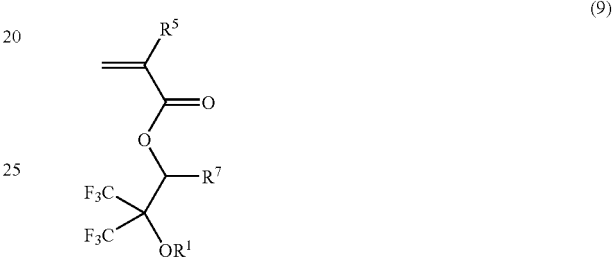

Herein $R^1$, $R^5$, and $R^7$ are as defined above.

The fluorinated monomer of formula (9) is obtained by esterifying the fluoroalcohol compound of formula (8) with an esterifying agent of formula (23) according to the following reaction scheme.

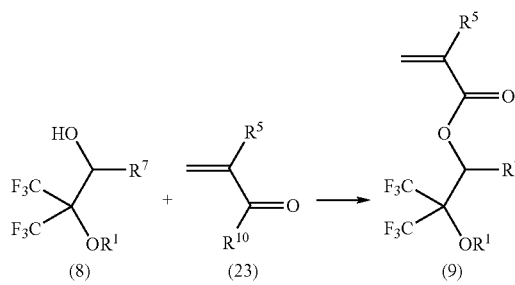

Herein $R^1$, $R^5$, $R^7$, and $R^{10}$ are as defined above.

The esterification reaction takes place readily by a well-known technique. The esterifying agent (23) used herein is preferably an acid chloride (corresponding to formula (23) wherein $R^{10}$ is chlorine), a carboxylic acid (corresponding to formula (23) wherein $R^{10}$ is —$OR^{11}$ wherein $R^{11}$ is hydrogen), or an acid anhydride (corresponding to formula (23) wherein $R^{10}$ is —$OR^{11}$ wherein $R^{11}$ is —C(=O)$R^5$C=CH$_2$ or the like). Where an acid chloride is used, the reaction may be conducted in a solventless system or in a solvent such as methylene chloride, toluene or hexane, by sequentially or simultaneously adding the alcohol (8), the acid chloride (e.g., methacrylic acid chloride or α-trifluoromethylacrylic acid chloride), and a base (e.g., triethylamine, pyridine or 4-dimethylaminopyridine), and allowing the reaction to take place while cooling or heating if necessary. Where a carboxylic acid is used, the reaction may be conducted in a solvent such as toluene or hexane, by adding the alcohol (8), the carboxylic acid (e.g., methacrylic acid or α-trifluoromethylacrylic acid), a mineral acid (e.g., hydrochloric acid, sulfuric acid, nitric acid or perchloric acid), and an organic acid (e.g., p-toluenesulfonic acid, benzenesulfonic acid or trifluoroacetic acid), heating the system, and removing the water resulting from reaction out of the system, if necessary; or in a solventless system or in a solvent such as toluene or hexane, by sequentially or simultaneously adding the alcohol (8), an aliphatic sulfonyl chloride (e.g., methane sulfonyl chloride), an aromatic sulfonyl chloride (e.g., p-toluenesulfonic acid chloride), and an acid anhydride (e.g., acetic anhydride or trifluoroacetic anhydride), and optionally, a base (e.g., triethylamine, pyridine or 4-dimethylaminopyridine), and allowing the reaction to take place while cooling or heating if necessary. Where an acid anhydride is used, the reaction may be conducted in a solventless system or in a solvent such as methylene chloride, toluene or hexane, by sequentially or simultaneously adding the alcohol (8), the acid anhydride (e.g., methacrylic acid anhydride or α-trifluoromethylacrylic acid anhydride), a mineral acid (e.g., hydrochloric acid, sulfuric acid, nitric acid or perchloric acid), and an organic acid (e.g., p-toluenesulfonic acid, benzenesulfonic acid or trifluoroacetic acid), or a base (e.g., triethylamine, pyridine or 4-dimethylaminopyridine), and allowing the reaction to take place while cooling or heating if necessary.

It is understood that the acid anhydride used herein may be a mixture of acid anhydride with another acid examples of which include carboxylic acids such as formic acid, acetic acid and trifluoroacetic acid, sulfonic acids such as methanesulfonic acid and p-toluenesulfonic acid, and phenols such as phenol and p-nitrophenol.

A fluorinated monomer of formula (9) wherein $R^1$ is hydrogen can be produced by using a corresponding fluoroalcohol compound of formula (8) wherein $R^1$ is hydrogen, and subjecting the hydroxyl group on the desired side to selective mono-esterification. Alternatively, the desired compound (9) can be produced by esterifying both the hydroxyl groups on the fluoroalcohol compound of formula (8) to form a diester compound having the general formula (26), shown below, and effecting deprotection such as hydrolytic reaction.

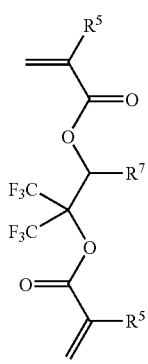

(26)

Herein, $R^5$ and $R^7$ are as defined above.

Illustrative, non-limiting examples of the compound of formula (9) are given below.

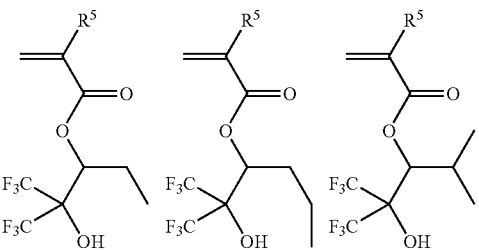

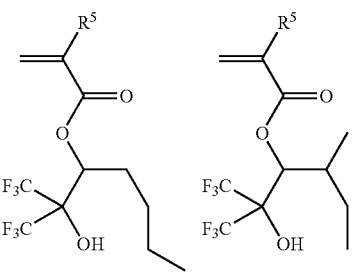

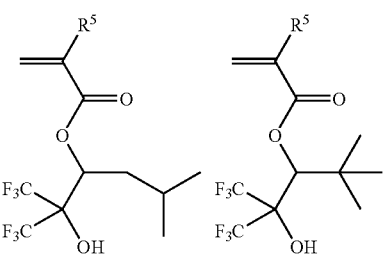

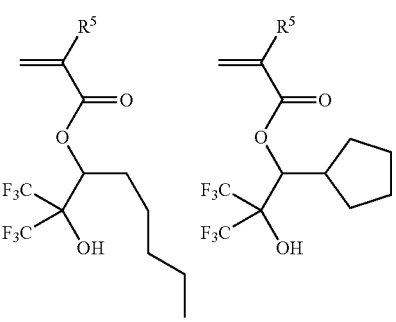

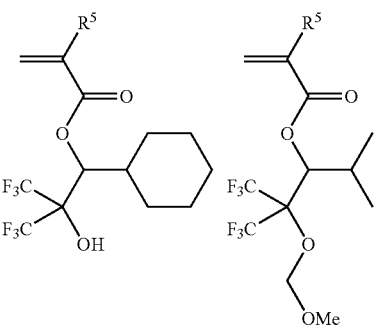

-continued
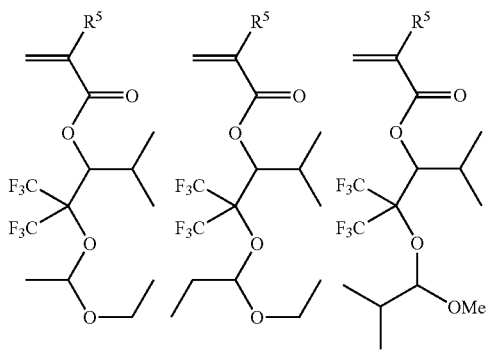
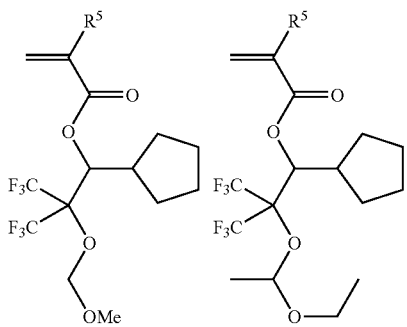
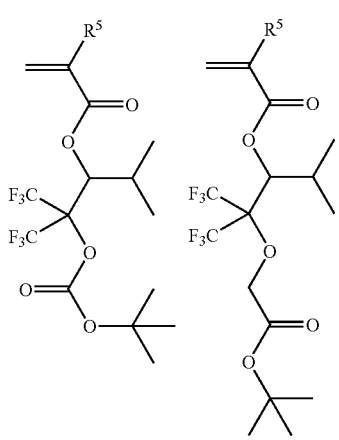
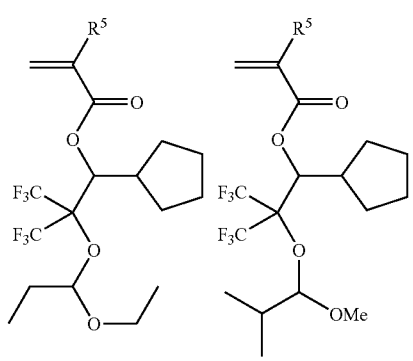
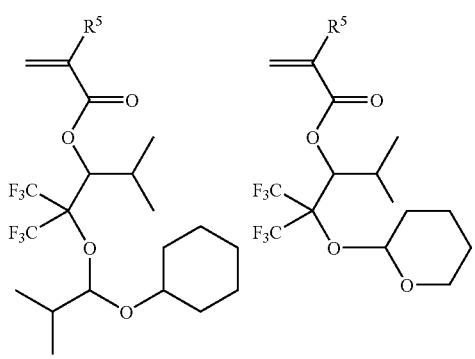
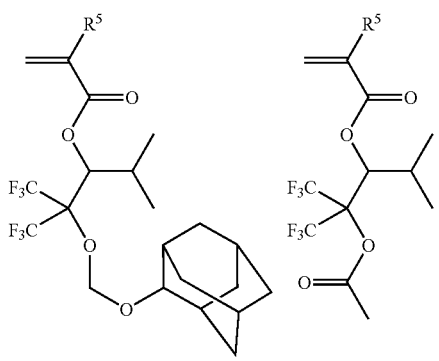
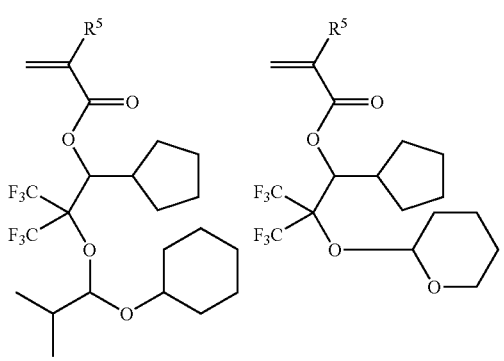

-continued

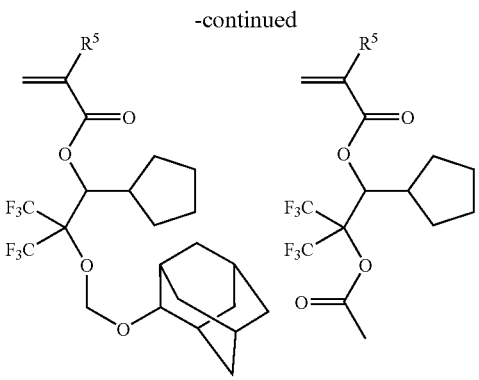

Herein, $R^5$ is as defined above and Me is methyl.

The fourth fluorinated monomer of the invention is a compound having the general formula (10), which is obtained through esterification of the fluoroalcohol compound having formula (8).

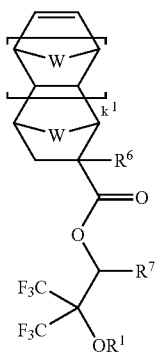

(10)

Herein $R^1$, $R^6$, $R^7$, W, and $k^1$ are as defined above.

The fluorinated monomer of formula (10) is obtained by esterifying the fluoroalcohol compound of formula (8) with an esterifying agent of formula (25) according to the following reaction scheme.

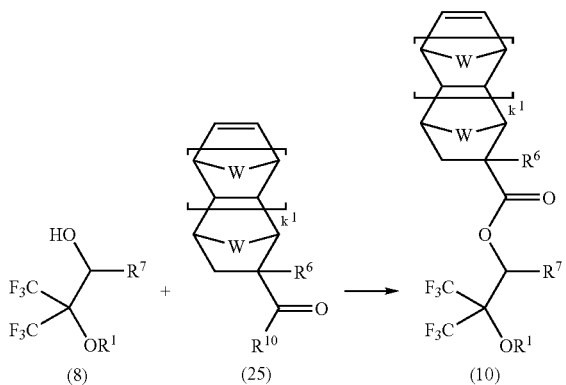

Herein $R^1$, $R^6$, $R^7$, $R^{10}$, W and $k^1$ are as defined above.

The esterification reaction takes place readily by a well-known technique. The esterifying agent (25) used herein is preferably an acid chloride (corresponding to formula (25) wherein $R^{10}$ is chlorine), a carboxylic acid (corresponding to formula (25) wherein $R^{10}$ is —$OR^{11}$ wherein $R^{11}$ is hydrogen), or an acid anhydride (corresponding to formula (25) wherein $R^{10}$ is —$OR^{11}$, wherein $R^{11}$ is

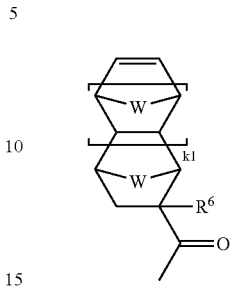

or the like). Where an acid chloride is used, the reaction may be conducted in a solventless system or in a solvent such as methylene chloride, toluene or hexane, by sequentially or simultaneously adding the alcohol (8), the acid chloride (e.g., 5-norbornene-2-carboxylic acid chloride or 7-oxa-5-norbornene-2-carboxylic acid chloride), and a base (e.g., triethylamine, pyridine or 4-dimethylaminopyridine), and allowing the reaction to take place while cooling or heating if necessary. Where a carboxylic acid is used, the reaction may be conducted in a solvent such as toluene or hexane, by adding the alcohol (8), the carboxylic acid (e.g., 5-norbornene-2-carboxylic acid or 7-oxa-5-norbornene-2-carboxylic acid), a mineral acid (e.g., hydrochloric acid, sulfuric acid, nitric acid or perchloric acid), and an organic acid (e.g., p-toluenesulfonic acid, benzenesulfonic acid or trifluoroacetic acid), heating the system, and removing the water resulting from reaction out of the system, if necessary; or in a solventless system or in a solvent such as toluene or hexane, by sequentially or simultaneously adding the alcohol (8), an aliphatic sulfonyl chloride (e.g., methane sulfonyl chloride), an aromatic sulfonyl chloride (e.g., p-toluenesulfonic acid chloride), and an acid anhydride (e.g., acetic anhydride or trifluoroacetic anhydride), and optionally, a base (e.g., triethylamine, pyridine or 4-dimethylaminopyridine), and allowing the reaction to take place while cooling or heating if necessary. Where an acid anhydride is used, the reaction may be conducted in a solventless system or in a solvent such as methylene chloride, toluene or hexane, by sequentially or simultaneously adding the alcohol (8), the acid anhydride (e.g., norbornenecarboxylic acid anhydride or tetracyclododecenecarboxylic acid anhydride), a mineral acid (e.g., hydrochloric acid, sulfuric acid, nitric acid or perchloric acid), and an organic acid (e.g., p-toluenesulfonic acid, benzenesulfonic acid or trifluoroacetic acid), or a base (e.g., triethylamine, pyridine or 4-dimethylaminopyridine), and allowing the reaction to take place while cooling or heating if necessary.

It is understood that the acid anhydride used herein may be a mixture of acid anhydride with another acid, examples of which include carboxylic acids such as formic acid, acetic acid and trifluoroacetic acid, sulfonic acids such as methanesulfonic acid and p-toluenesulfonic acid, and phenols such as phenol and p-nitrophenol.

The desired compound (10) may also be derived through Diels-Alder reaction of the fluorinated monomer (9) with furan or a corresponding diene compound such as cyclopentadiene.

Illustrative, non-limiting examples of the compound of formula (10) are given below.

-continued
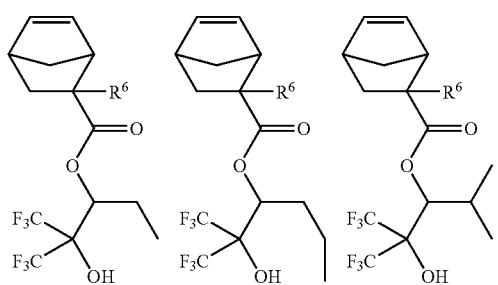
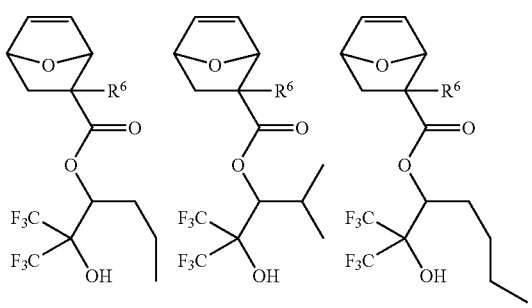
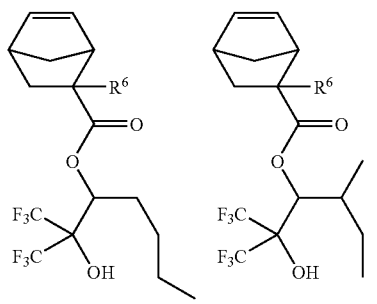
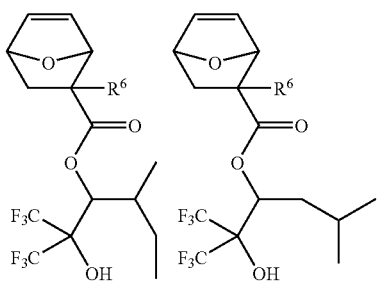
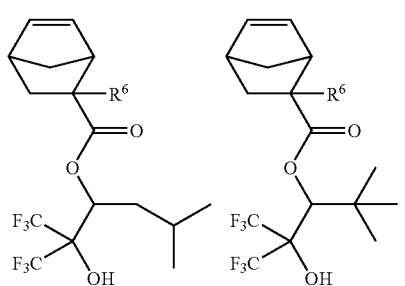
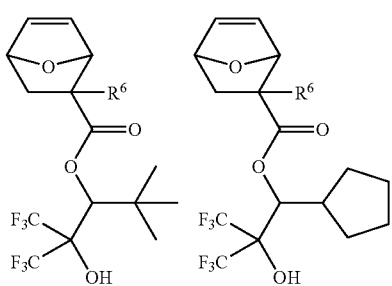
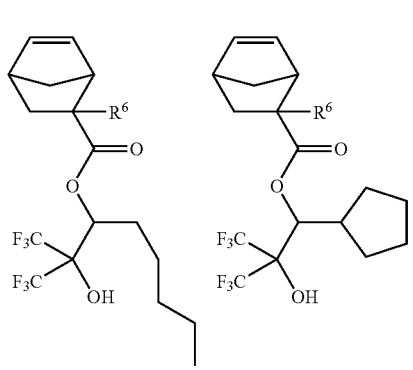
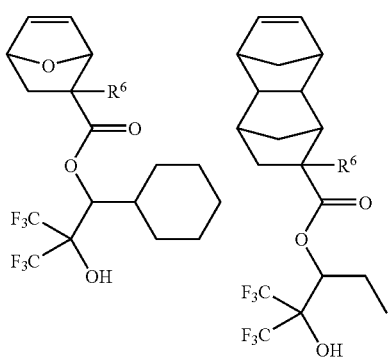
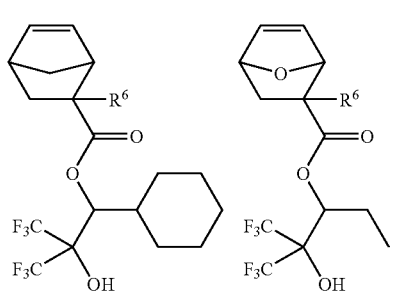
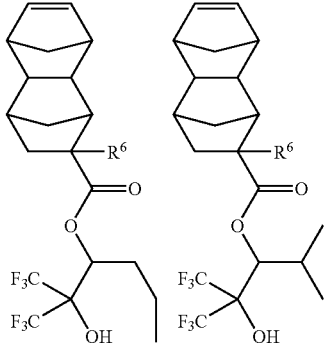

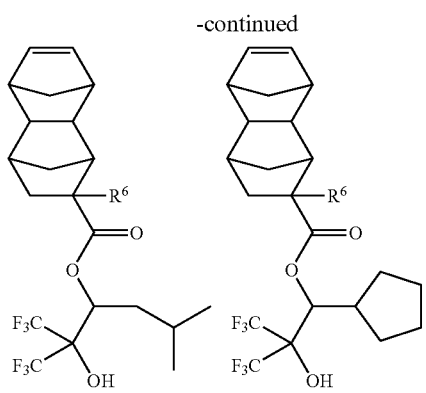
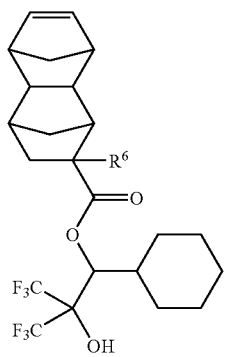
Herein, R⁶ is as defined above.
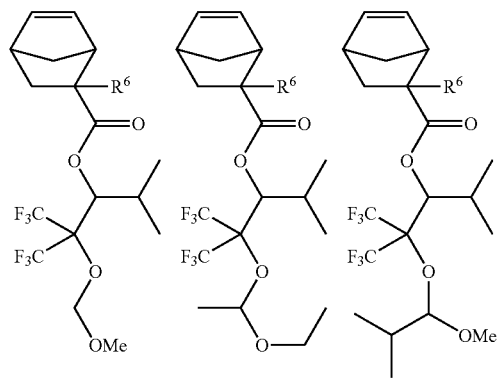
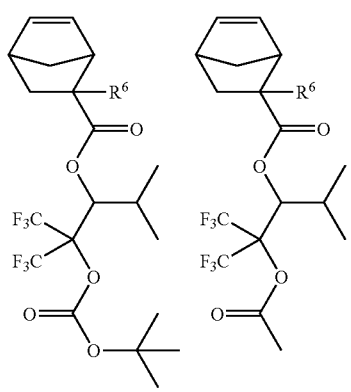
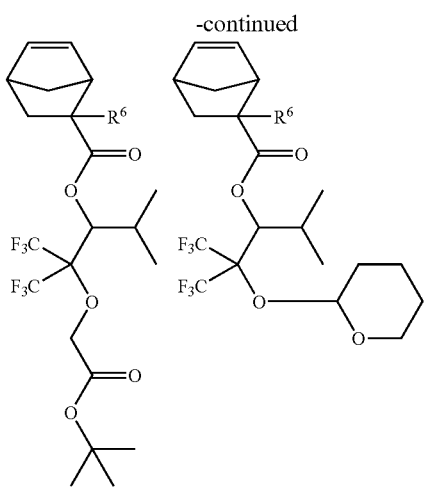
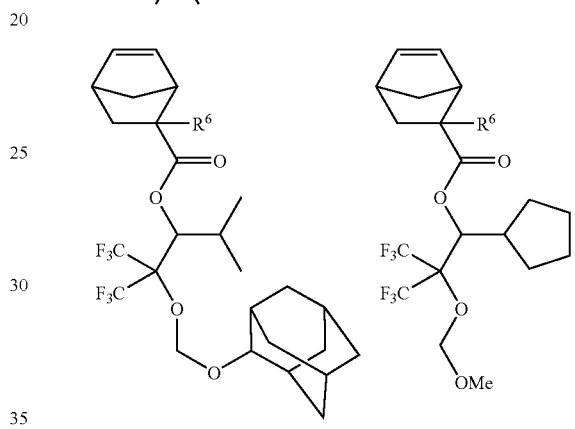
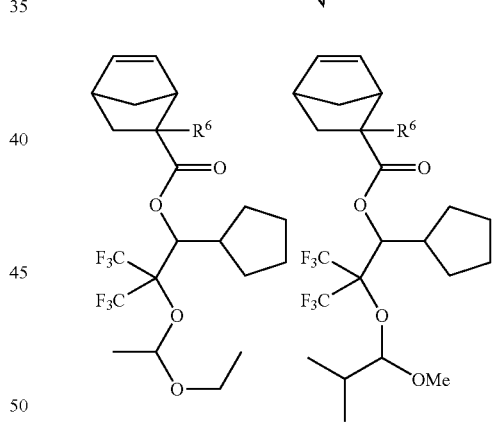
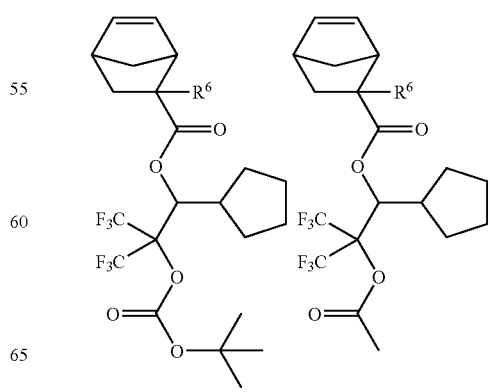

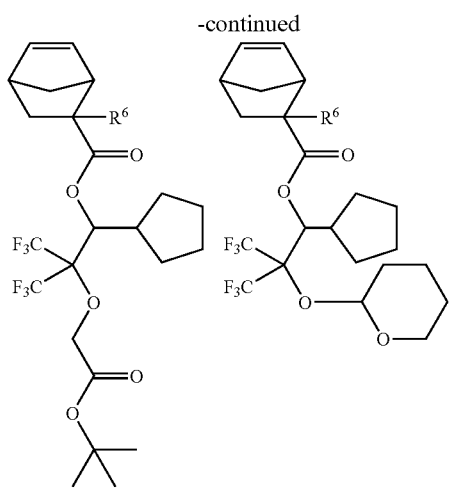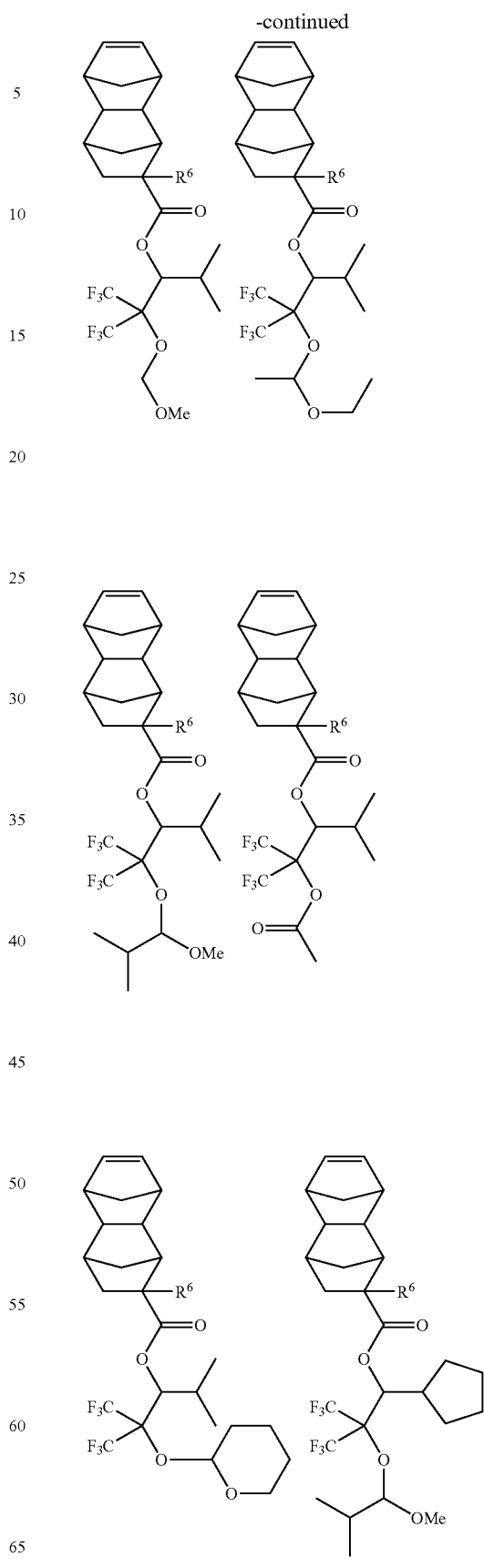

-continued

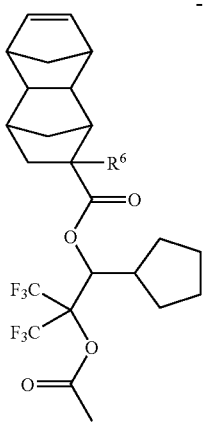

Herein, $R^6$ is as defined above and Me is methyl.

The third aspect of the invention also relates to a method for preparing a fluoroalcohol compound. The method comprises the step of nucleophilic addition reaction of an organometallic reagent having the general formula (11) to a fluorine compound having the general formula (1) for thereby forming a fluoroalcohol compound having the general formula (12).

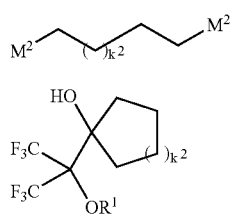

Herein $R^1$ and $M^2$ are as defined above, and $k^2$ is 1 or 2.

The amount of the organometallic reagent (11) used varies over a wide range with conditions. In the case of a fluorine compound of formula (1) wherein $R^1$ is hydrogen, for example, the reagent is desirably used in an amount of 1.0 to 5.0 moles, more desirably 1.0 to 3.0 moles per mole of fluorine compound (1). Suitable solvents include ethers such as tetrahydrofuran, diethyl ether, di-n-butyl ether and 1,4-dioxane, and hydrocarbons such as n-hexane, n-heptane, benzene, toluene, xylene and cumene. These solvents may be used alone or in admixture. The reaction temperature and time vary with other conditions. Where a Grignard reagent (corresponding to formula (11) wherein $M^2$ is MgP wherein P is halogen) is used as the organometallic reagent, for example, the reaction may be conducted at a temperature of 0 to 100° C., preferably 20 to 70° C. It is desired for higher yields that the reaction be driven to completion by monitoring the progress of reaction by gas chromatography (GC) or silica gel thin-layer chromatography (TLC). The reaction time is usually about 0.5 hour to about 10 hours. The fluoroalcohol compound (12) may be recovered from the reaction mixture by ordinary aqueous work-up. If necessary, the fluoroalcohol compound (12) can be purified by any standard technique such as distillation or recrystallization.

The fifth fluorinated monomer of the invention is a compound having the general formula (13), which is obtained through esterification of the fluoroalcohol compound having formula (12).

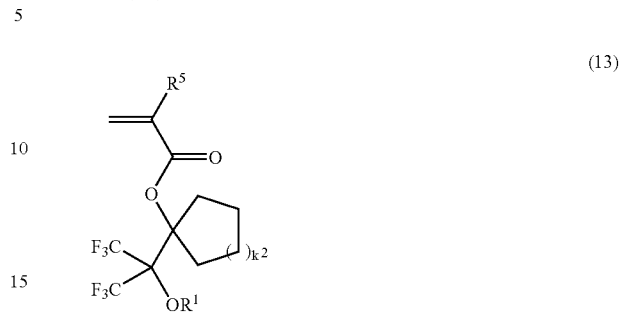

Herein $R^1$, $R^5$, and $k^2$ are as defined above.

The fluorinated monomer of formula (13) is obtained by esterifying the fluoroalcohol compound of formula (12) with an esterifying agent of formula (23) according to the following reaction scheme.

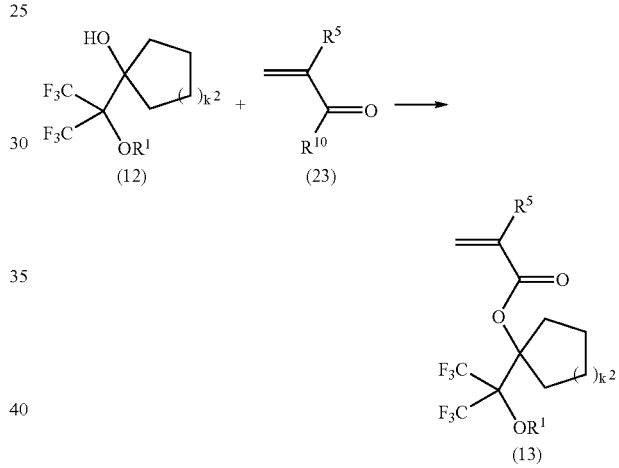

Herein $R^1$, $R^5$, $R^{10}$, and $k^2$ are as defined above.

The esterification reaction takes place readily by a well-known technique. The esterifying agent (23) used herein is preferably an acid chloride (corresponding to formula (23) wherein $R^{10}$ is chlorine), a carboxylic acid (corresponding to formula (23) wherein $R^{10}$ is —$OR^{11}$ wherein $R^{11}$ is hydrogen), or an acid anhydride (corresponding to formula (23) wherein $R^{10}$ is —$OR^{11}$ wherein $R^{11}$ is —C(=O)$R^5$C=CH$_2$ or the like). Where an acid chloride is used, the reaction may be conducted in a solventless system or in a solvent such as methylene chloride, toluene or hexane, by sequentially or simultaneously adding the alcohol (12), the acid chloride (e.g., methacrylic acid chloride or α-trifluoromethylacrylic acid chloride), and a base (e.g., triethylamine, pyridine or 4-dimethylaminopyridine), and allowing the reaction to take place while cooling or heating if necessary. Where a carboxylic acid is used, the reaction may be conducted in a solvent such as toluene or hexane, by adding the alcohol (12), the carboxylic acid (e.g., methacrylic acid or α-trifluoromethylacrylic acid), a mineral acid (e.g., hydrochloric acid, sulfuric acid, nitric acid or perchloric acid), and an organic acid (e.g., p-toluenesulfonic acid, benzenesulfonic acid or trifluoroacetic acid), heating the system, and removing the water resulting from reaction out of the system, if necessary; or in a solventless system or in a solvent such as toluene or hexane, by sequentially or simultaneously adding the alcohol (12), an aliphatic sulfonyl chloride (e.g., methane sulfonyl chloride), an aromatic sulfonyl chloride (e.g., p-toluenesulfonic acid chloride), and an acid anhydride (e.g., acetic anhydride or trifluoroacetic anhydride), and optionally, a base (e.g., triethylamine, pyridine or 4-dimethylaminopyridine), and allowing the reaction to take place while cooling or heating if necessary. Where an acid anhydride is used, the reaction may be conducted in a solventless system or in a solvent such as methylene chloride, toluene or hexane, by sequentially or simultaneously adding the alcohol (12), the acid anhydride (e.g., methacrylic acid anhydride or α-trifluoromethylacrylic acid anhydride), a mineral acid (e.g., hydrochloric acid, sulfuric acid, nitric acid or perchloric acid), and an organic acid (e.g., p-toluenesulfonic acid, benzenesulfonic acid or trifluoroacetic acid), or a base (e.g., triethylamine, pyridine or 4-dimethylaminopyridine), and allowing the reaction to take place while cooling or heating if necessary.

It is understood that the acid anhydride used herein may be a mixture of acid anhydride with another acid examples of which include carboxylic acids such as formic acid, acetic acid and trifluoroacetic acid, sulfonic acids such as methanesulfonic acid and p-toluenesulfonic acid, and phenols such as phenol and p-nitrophenol.

A fluorinated monomer of formula (13) wherein $R^1$ is hydrogen can be produced by using a corresponding fluoroalcohol compound of formula (12) wherein $R^1$ is hydrogen, and subjecting the hydroxyl group on the desired side to selective mono-esterification. Alternatively, the desired compound (13) can be produced by esterifying both the hydroxyl groups on the fluoroalcohol compound of formula (12) to form a diester compound having the general formula (27), shown below, and effecting deprotection such as hydrolytic reaction.

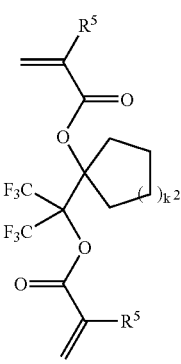

(27)

Herein, $R^5$ and $k^2$ are as defined above.

Illustrative, non-limiting examples of the compound of formula (13) are given below.

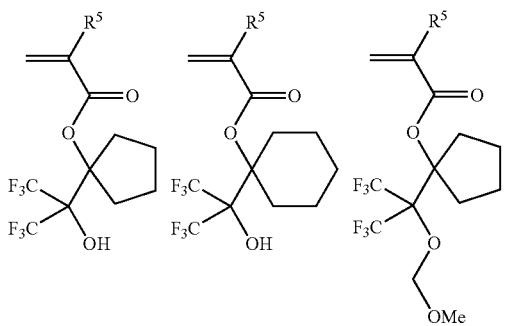

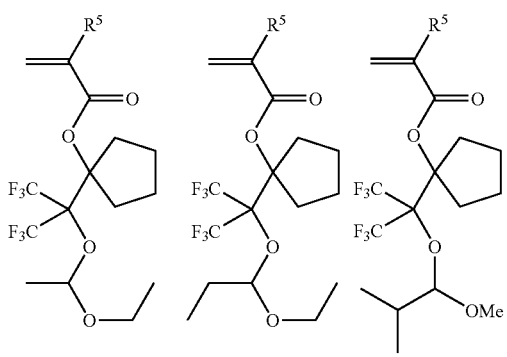

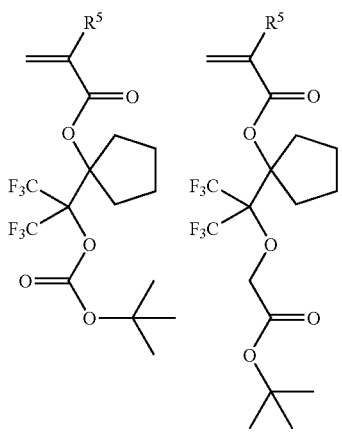

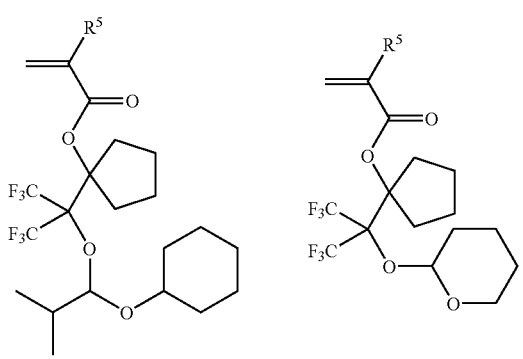

-continued

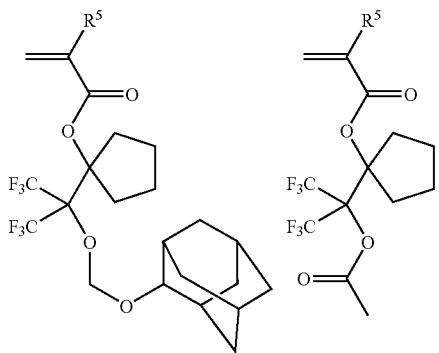
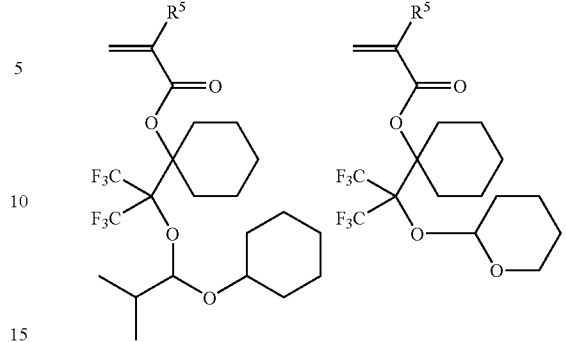

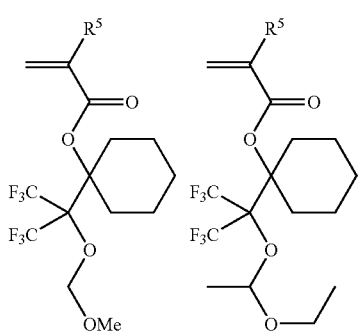
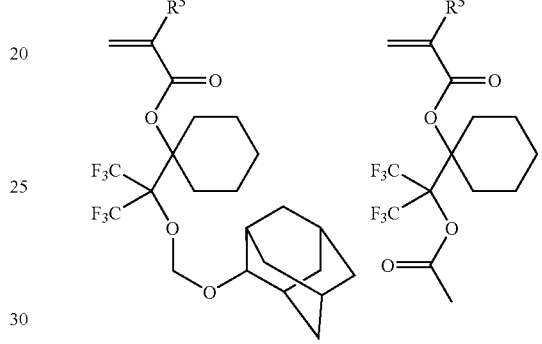

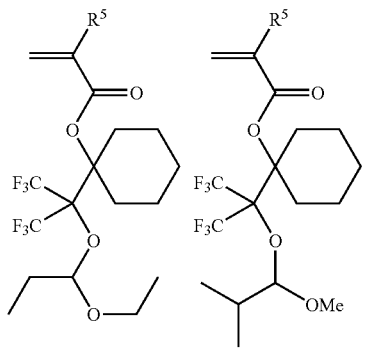

Herein, $R^5$ is as defined above and Me is methyl.

The sixth fluorinated monomer of the invention is a compound having the general formula (14), which is obtained through esterification of the fluoroalcohol compound having formula (12).

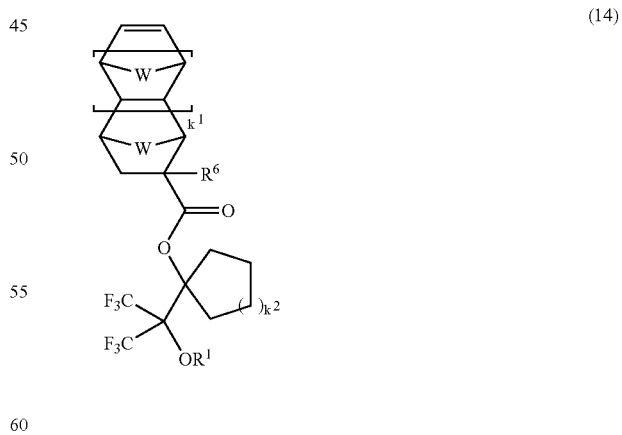

(14)

Herein $R^1$, $R^6$, W, $k^1$ and $k^2$ are as defined above.

The fluorinated monomer of formula (14) is obtained by esterifying the fluoroalcohol compound of formula (12) with an esterifying agent of formula (25) according to the following reaction scheme.

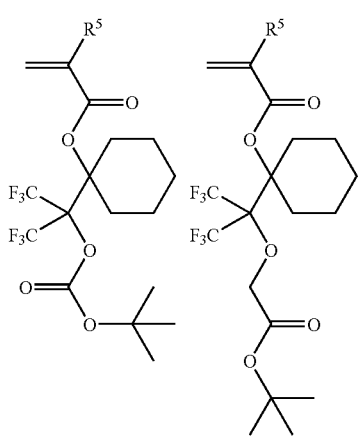

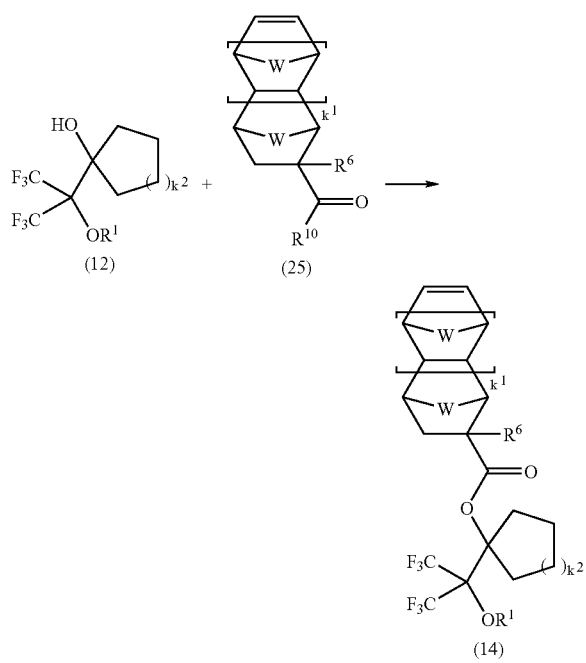

Herein $R^1$, $R^6$, $R^{10}$, W, $k^1$ and $k^2$ are as defined above.

The esterification reaction takes place readily by a well-known technique. The esterifying agent (25) used herein is preferably an acid chloride (corresponding to formula (25) wherein $R^{10}$ is chlorine), a carboxylic acid (corresponding to formula (25) wherein $R^{10}$ is $-OR^{11}$ wherein $R^{11}$ is hydrogen), or an acid anhydride (corresponding to formula (25) wherein $R^{10}$ is $-OR^{11}$ wherein $R^{11}$ is

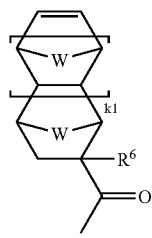

or the like). Where an acid chloride is used, the reaction may be conducted in a solventless system or in a solvent such as methylene chloride, toluene or hexane, by sequentially or simultaneously adding the alcohol (12), the acid chloride (e.g., 5-norbornene-2-carboxylic acid chloride or 7-oxa-5-norbornene-2-carboxylic acid chloride), and a base (e.g., triethylamine, pyridine or 4-dimethylaminopyridine), and allowing the reaction to take place while cooling or heating if necessary. Where a carboxylic acid is used, the reaction may be conducted in a solvent such as toluene or hexane, by adding the alcohol (12), the carboxylic acid (e.g., 5-norbornene-2-carboxylic acid or 7-oxa-5-norbornene-2-carboxylic acid), a mineral acid (e.g., hydrochloric acid, sulfuric acid, nitric acid or perchloric acid), and an organic acid (e.g., p-toluenesulfonic acid, benzenesulfonic acid or trifluoroacetic acid), heating the system, and removing the water resulting from reaction out of the system, if necessary; or in a solventless system or in a solvent such as toluene or hexane, by sequentially or simultaneously adding the alcohol (12), an aliphatic sulfonyl chloride (e.g., methane sulfonyl chloride), an aromatic sulfonyl chloride (e.g., p-toluenesulfonic acid chloride), and an acid anhydride (e.g., acetic anhydride or trifluoroacetic anhydride), and optionally, a base (e.g., triethylamine, pyridine or 4-dimethylaminopyridine), and allowing the reaction to take place while cooling or heating if necessary. Where an acid anhydride is used, the reaction may be conducted in a solventless system or in a solvent such as methylene chloride, toluene or hexane, by sequentially or simultaneously adding the alcohol (12), the acid anhydride (e.g., norbornenecarboxylic acid anhydride or tetracyclododecenecarboxylic acid anhydride), a mineral acid (e.g., hydrochloric acid, sulfuric acid, nitric acid or perchloric acid), and an organic acid (e.g., p-toluenesulfonic acid, benzenesulfonic acid or trifluoroacetic acid), or a base (e.g., triethylamine, pyridine or 4-dimethylaminopyridine), and allowing the reaction to take place while cooling or heating if necessary.

It is understood that the acid anhydride used herein may be a mixture of acid anhydride with another acid, examples of which include carboxylic acids such as formic acid, acetic acid and trifluoroacetic acid, sulfonic acids such as methanesulfonic acid and p-toluenesulfonic acid, and phenols such as phenol and p-nitrophenol.

The desired compound (14) may also be derived through Diels-Alder reaction of the fluorinated monomer (13) with furan or a corresponding diene compound such as cyclopentadiene.

Illustrative, non-limiting examples of the compound of formula (14) are given below.

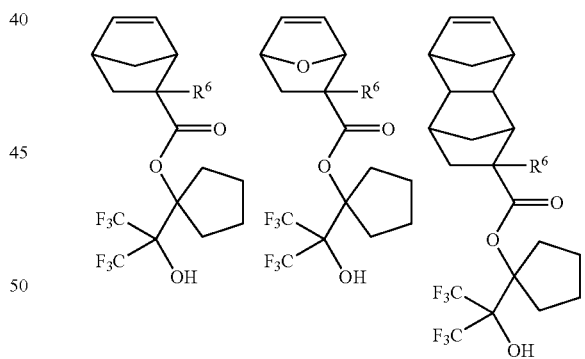

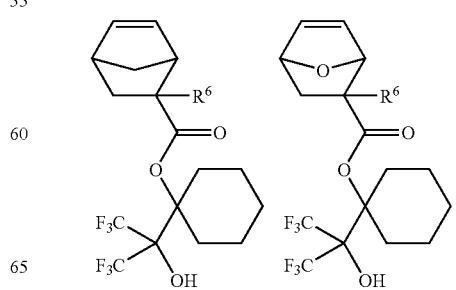

-continued
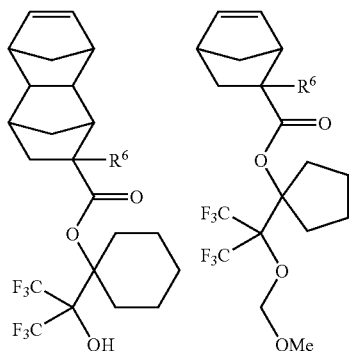
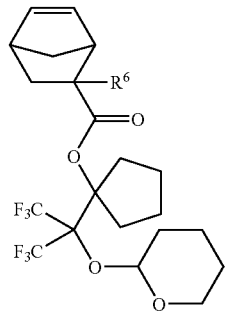
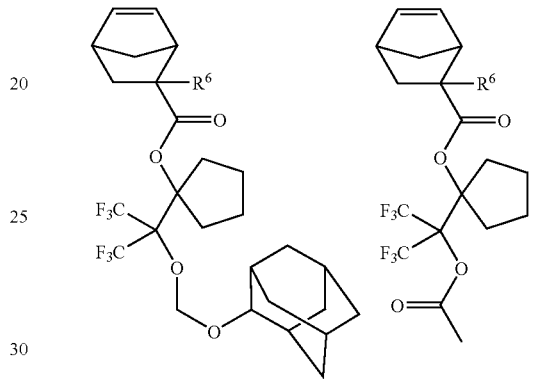
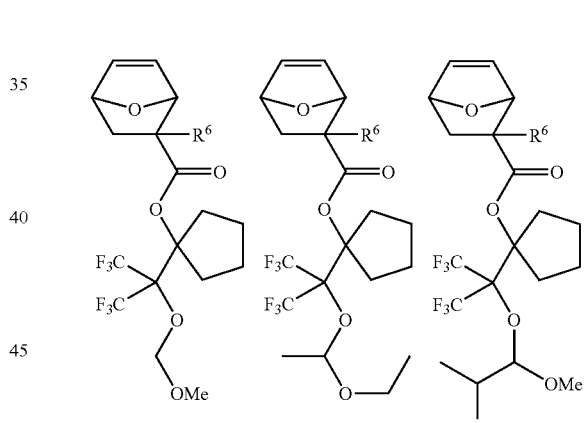
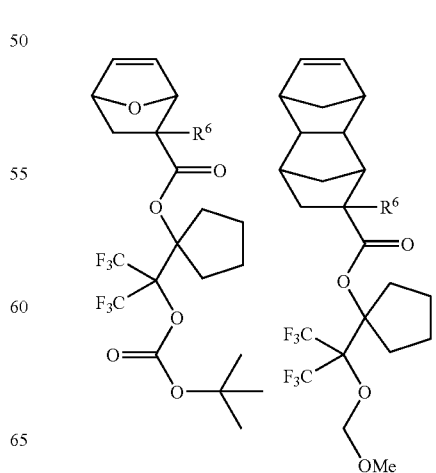

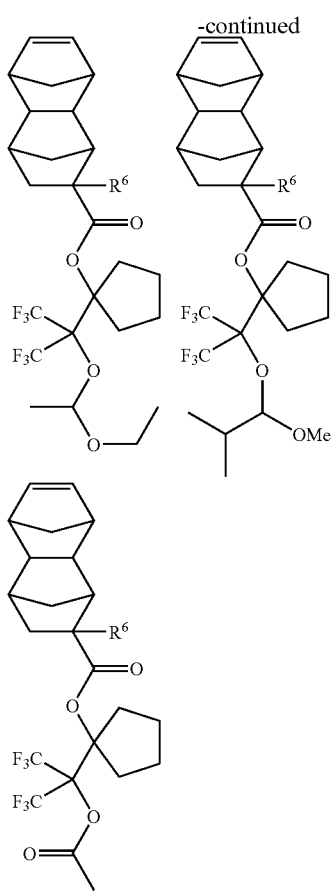

Herein, $R^6$ is as defined above and Me is methyl.

The fourth aspect of the invention also relates to a method for preparing a fluoroalcohol compound. The method comprises the step of addition reaction of an organometallic reagent having the general formula (15) to a fluorine compound having the general formula (1) for thereby forming a fluoroalcohol compound having the general formula (16).

$$MeM^2 \quad (15)$$

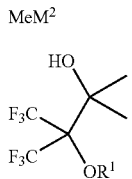

(16)

Herein $R^1$ and $M^2$ are as defined above, and Me is methyl.

The amount of the organometallic reagent (15) used varies over a wide range with conditions. In the case of a fluorine compound of formula (1) wherein $R^1$ is hydrogen, for example, the reagent is desirably used in an amount of 2.0 to 5.0 moles, more desirably 2.0 to 3.0 moles per mole of fluorine compound (1). Suitable solvents include ethers such as tetrahydrofuran, diethyl ether, di-n-butyl ether and 1,4-dioxane, and hydrocarbons such as n-hexane, n-heptane, benzene, toluene, xylene and cumene. These solvents may be used alone or in admixture. The reaction temperature and time vary with other conditions. Where a Grignard reagent (corresponding to formula (15) wherein $M^2$ is MgP wherein P is halogen) is used as the organometallic reagent, for example, the reaction may be conducted at a temperature of 0 to 100° C., preferably 20 to 70° C. It is desired for higher yields that the reaction be driven to completion by monitoring the progress of reaction by gas chromatography (GC) or silica gel thin-layer chromatography (TLC). The reaction time is usually about 0.5 hour to about 10 hours. The fluoroalcohol compound (16) may be recovered from the reaction mixture by ordinary aqueous work-up. If necessary, the fluoroalcohol compound (16) can be purified by any standard technique such as distillation or recrystallization.

The seventh fluorinated monomer of the invention is a compound having the general formula (17), which is obtained through esterification of the fluoroalcohol compound having formula (16).

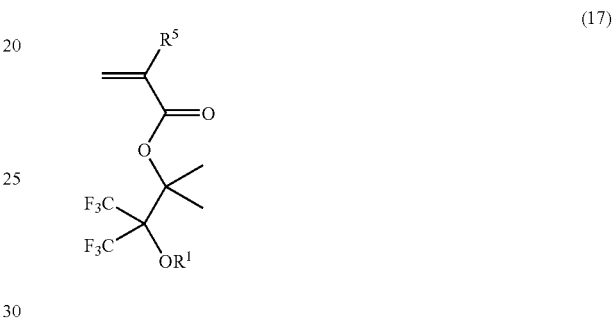

(17)

Herein $R^1$ and $R^5$ are as defined above.

The fluorinated monomer of formula (17) is obtained by esterifying the fluoroalcohol compound of formula (16) with an esterifying agent of formula (23) according to the following reaction scheme.

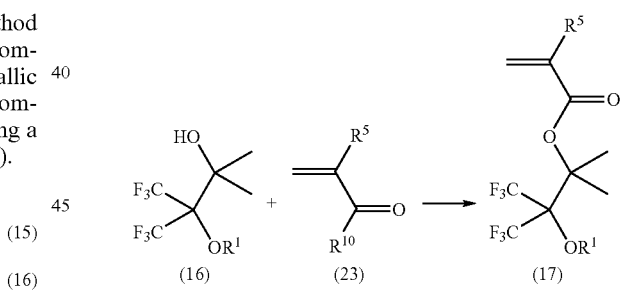

Herein $R^1$, $R^5$, and $R^{10}$ are as defined above.

The esterification reaction takes place readily by a well-known technique. The esterifying agent (23) used herein is preferably an acid chloride (corresponding to formula (23) wherein $R^{10}$ is chlorine), a carboxylic acid (corresponding to formula (23) wherein $R^{10}$ is —$OR^{11}$ wherein $R^{11}$ is hydrogen), or an acid anhydride (corresponding to formula (23) wherein $R^{10}$ is —$OR^{11}$ wherein $R^{11}$ is —C(=O)$R^5$C=$CH_2$ or the like). Where an acid chloride is used, the reaction may be conducted in a solventless system or in a solvent such as methylene chloride, toluene or hexane, by sequentially or simultaneously adding the alcohol (16), the acid chloride (e.g., methacrylic acid chloride or α-trifluoromethylacrylic acid chloride), and a base (e.g., triethylamine, pyridine or 4-dimethylaminopyridine), and allowing the reaction to take place while cooling or heating if necessary. Where a carboxylic acid is used, the reaction may be conducted in a solvent such as toluene or hexane, by adding the alcohol (16), the carboxylic acid (e.g., methacrylic acid or α-trifluoromethylacrylic acid), a mineral acid (e.g., hydrochloric acid, sulfuric acid, nitric acid or perchloric acid), and an organic acid (e.g., p-toluenesulfonic acid, benzenesulfonic acid or trifluoroacetic acid), heating the system, and removing the water resulting from reaction out of the system, if necessary; or in a solventless system or in a solvent such as toluene or hexane, by sequentially or simultaneously adding the alcohol (16), an aliphatic sulfonyl chloride (e.g., methane sulfonyl chloride), an aromatic sulfonyl chloride (e.g., p-toluenesulfonic acid chloride), and an acid anhydride (e.g., acetic anhydride or trifluoroacetic anhydride), and optionally, a base (e.g., triethylamine, pyridine or 4-dimethylaminopyridine), and allowing the reaction to take place while cooling or heating if necessary. Where an acid anhydride is used, the reaction may be conducted in a solventless system or in a solvent such as methylene chloride, toluene or hexane, by sequentially or simultaneously adding the alcohol (16), the acid anhydride (e.g., methacrylic acid anhydride or α-trifluoromethylacrylic acid anhydride), a mineral acid (e.g., hydrochloric acid, sulfuric acid, nitric acid or perchloric acid), and an organic acid (e.g., p-toluenesulfonic acid, benzenesulfonic acid or trifluoroacetic acid), or a base (e.g., triethylamine, pyridine or 4-dimethylaminopyridine), and allowing the reaction to take place while cooling or heating if necessary.

It is understood that the acid anhydride used herein may be a mixture of acid anhydride with another acid examples of which include carboxylic acids such as formic acid, acetic acid and trifluoroacetic acid, sulfonic acids such as methanesulfonic acid and p-toluenesulfonic acid, and phenols such as phenol and p-nitrophenol.

A fluorinated monomer of formula (17) wherein $R^1$ is hydrogen can be produced by using a corresponding fluoroalcohol compound of formula (16) wherein $R^1$ is hydrogen, and subjecting the hydroxyl group on the desired side to selective mono-esterification. Alternatively, the desired compound (17) can be produced by esterifying both the hydroxyl groups on the fluoroalcohol compound of formula (16) to form a diester compound having the general formula (28), shown below, and effecting deprotection such as hydrolytic reaction.

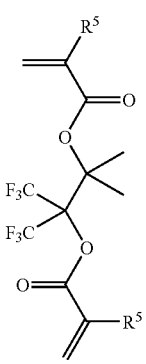

(28)

Herein, $R^5$ is as defined above.

Illustrative, non-limiting examples of the compound of formula (17) are given below.

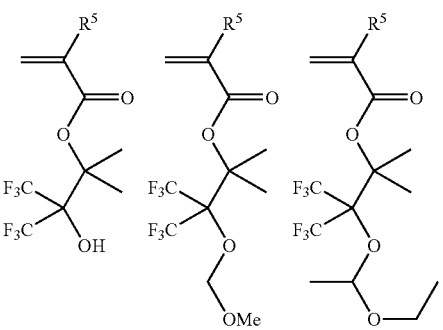

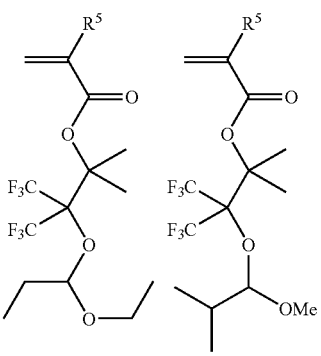

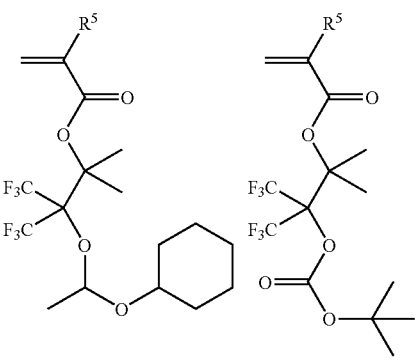

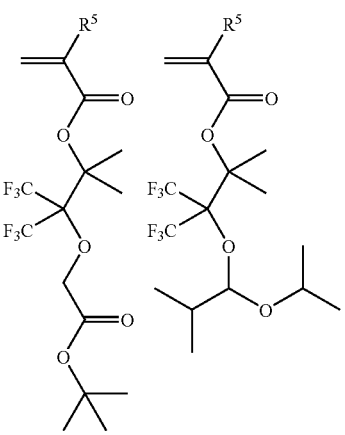

-continued

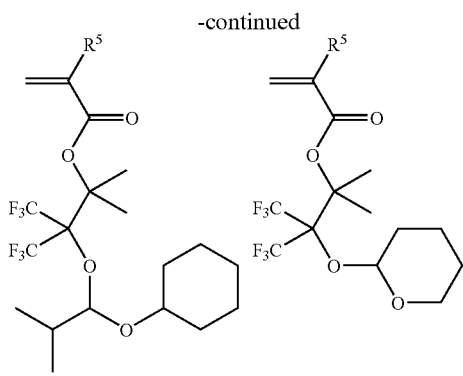

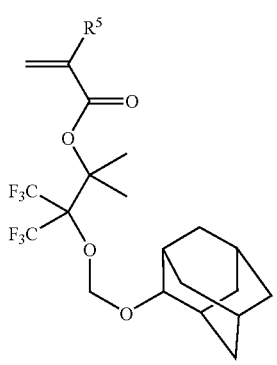

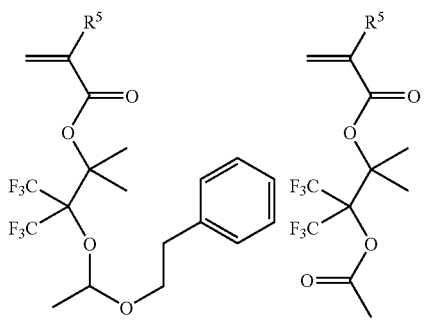

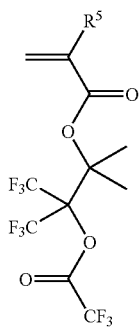

Herein, $R^5$ is as defined above and Me is methyl.

The eighth fluorinated monomer of the invention is a compound having the general formula (18), which is obtained through esterification of the fluoroalcohol compound having formula (16).

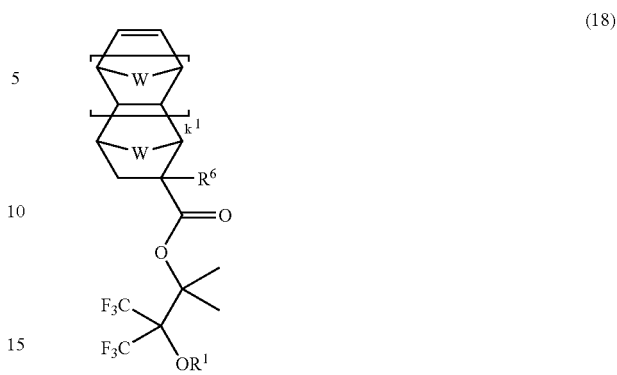

Herein $R^1$, $R^6$, W, and $k^1$ are as defined above.

The fluorinated monomer of formula (18) is obtained by esterifying the fluoroalcohol compound of formula (16) with an esterifying agent of formula (25) according to the following reaction scheme.

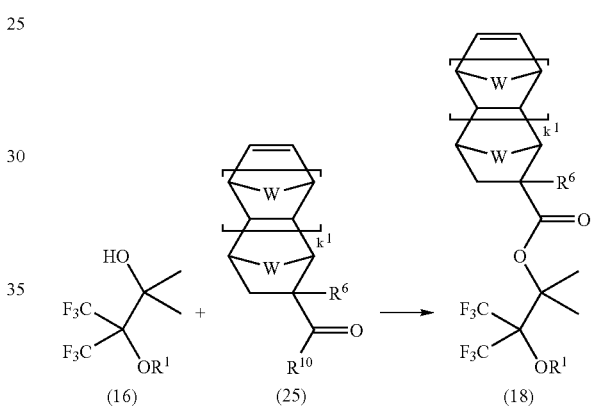

Herein $R^1$, $R^6$, $R^{10}$, W, and $k^1$ are as defined above.

The esterification reaction takes place readily by a well-known technique. The esterifying agent (25) used herein is preferably an acid chloride (corresponding to formula (25) wherein $R^{10}$ is chlorine), a carboxylic acid (corresponding to formula (25) wherein $R^{10}$ is —$OR^{11}$ wherein $R^{11}$ is hydrogen), or an acid anhydride (corresponding to formula (25) wherein $R^{10}$ is —$OR^{11}$ wherein $R^{11}$ is or the like). Where an acid chloride is used, the reaction may be conducted in a solventless system or in a solvent such as methylene chloride, toluene or hexane, by sequentially or simultaneously adding the alcohol (16), the acid chloride (e.g., 5-norbornene-2-carboxylic acid chloride or 7-oxa-5- norbornene-2-carboxylic acid chloride), and a base (e.g., triethylamine, pyridine or 4-dimethylaminopyridine), and allowing the reaction to take place while cooling or heating if necessary. Where a carboxylic acid is used, the reaction may be conducted in a solvent such as toluene or hexane, by adding the alcohol (16), the carboxylic acid (e.g., 5-norbornene-2-carboxylic acid or 7-oxa-5-norbornene-2-carboxylic acid), a mineral acid (e.g., hydrochloric acid, sulfuric acid, nitric acid or perchloric acid), and an organic acid (e.g., p-toluenesulfonic acid, benzenesulfonic acid or trifluoroacetic acid), heating the system, and removing the water resulting from reaction out of the system, if necessary; or in a solventless system or in a solvent such as toluene or hexane, by sequentially or simultaneously adding the alcohol (16), an aliphatic sulfonyl chloride (e.g., methane sulfonyl chloride), an aromatic sulfonyl chloride (e.g., p-toluenesulfonic acid chloride), and an acid anhydride (e.g., acetic anhydride or trifluoroacetic anhydride), and optionally, a base (e.g., triethylamine, pyridine or 4-dimethylaminopyridine), and allowing the reaction to take place while cooling or heating if necessary. Where an acid anhydride is used, the reaction may be conducted in a solventless system or in a solvent such as methylene chloride, toluene or hexane, by sequentially or simultaneously adding the alcohol (16), the acid anhydride (e.g., norbornenecarboxylic acid anhydride or tetracyclododecenecarboxylic acid anhydride), a mineral acid (e.g., hydrochloric acid, sulfuric acid, nitric acid or perchloric acid), and an organic acid (e.g., p-toluenesulfonic acid, benzenesulfonic acid or trifluoroacetic acid), or a base (e.g., triethylamine, pyridine or 4-dimethylaminopyridine), and allowing the reaction to take place while cooling or heating if necessary.

It is understood that the acid anhydride used herein may be a mixture of acid anhydride with another acid, examples of which include carboxylic acids such as formic acid, acetic acid and trifluoroacetic acid, sulfonic acids such as methanesulfonic acid and p-toluenesulfonic acid, and phenols such as phenol and p-nitrophenol.

The desired compound (18) may also be derived through Diels-Alder reaction of the fluorinated monomer (17) with furan or a corresponding diene compound such as cyclopentadiene.

Illustrative, non-limiting examples of the compound of formula (18) are given below.

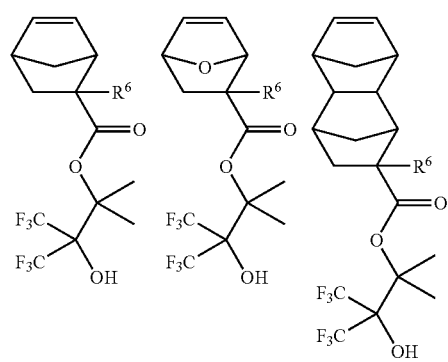

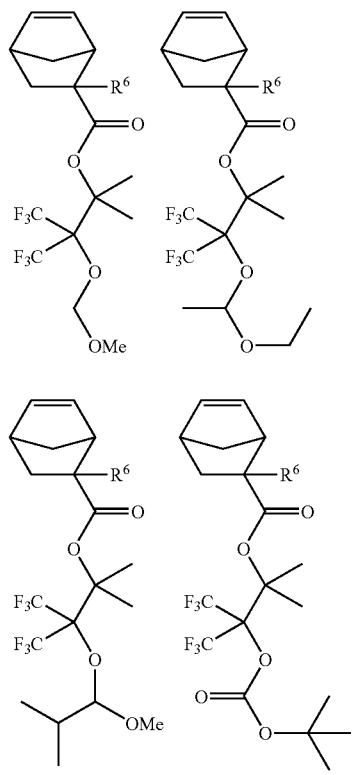

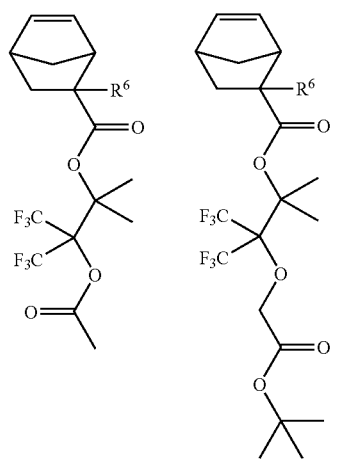

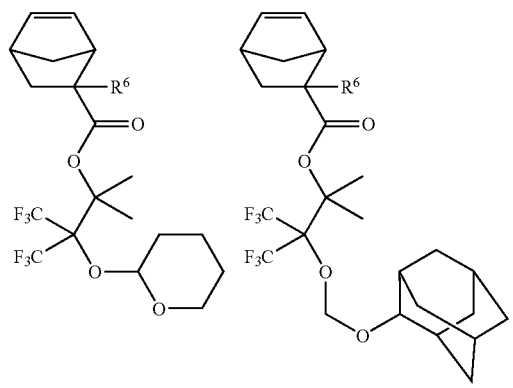

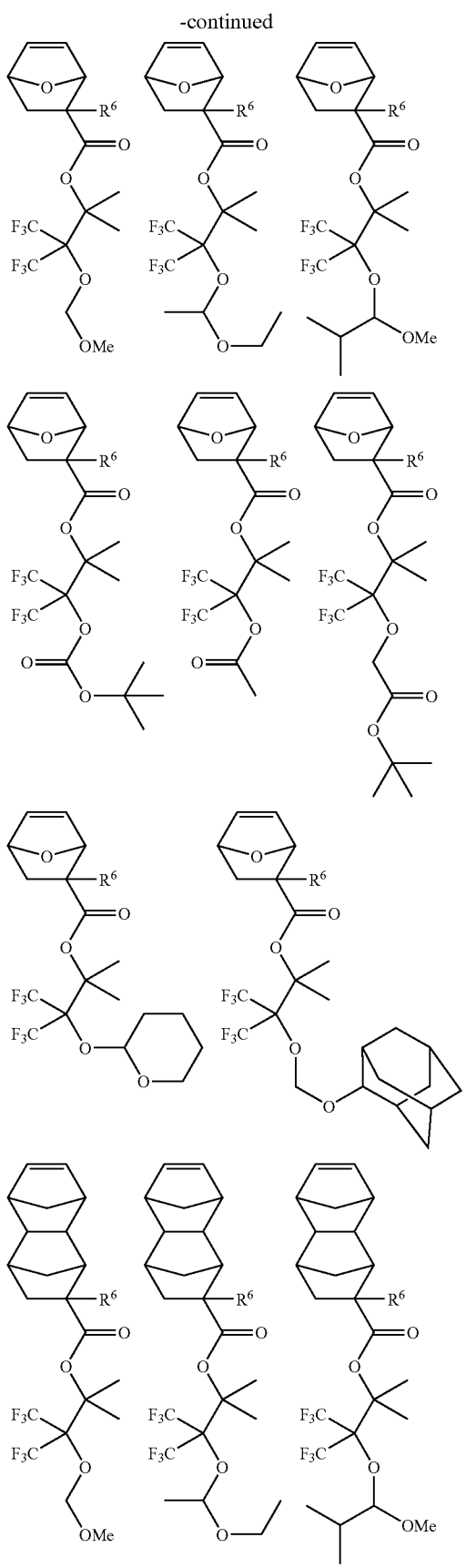
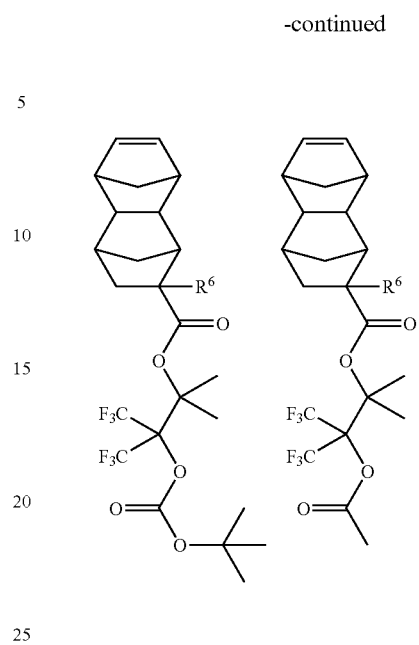

Herein, $R^6$ is as defined above and Me is methyl.

It is noted that JP-A 2003-040840 discloses the general structure encompassing the above general formulas (5), (9), (13), and (17), but not the synthesis method. It is unknown to those skilled in the art how to synthesize the compounds of the present invention, that is, compounds in which no carbon atoms intervene between the carbon having a trifluoromethyl group substituted thereon and the carbon having $CH_2$=$CR^5C$(=O)O— substituted thereon. The patent reference describes the structure with no intervening carbon (i.e., formula (2) in the patent reference) and illustrates the corresponding polymer (i.e., formula (12) in the patent reference). However, the monomer (i.e., formula (6) in the patent reference) from which the polymer is derived is a compound with one intervening carbon. The patent reference describes in its Example section a starting alcohol for the synthesis of the monomer, which supports the structure of formula (6) having one intervening carbon in the patent reference. Accordingly, in a substantial sense, the patent reference does not disclose compounds with no intervening carbon.

In a substantial sense, the present invention discloses for the first time those compounds in which no carbon atoms intervene between the carbon having a trifluoromethyl group substituted thereon and the carbon having $CH_2$=$CR^5C$(=O)O— substituted thereon as well as the synthesis method thereof.

Polymer

The polymer or high molecular weight compound of the invention is characterized by comprising recurring units derived from the fluorinated monomer of formula (5), (6), (9), (10), (13), (14), (17) or (18).

The recurring units derived from the fluorinated monomers of formulas (5) and (6) include those having the general formulas (1a) to (1c).

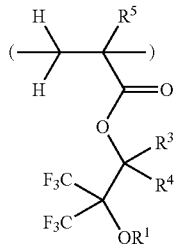
(1a)

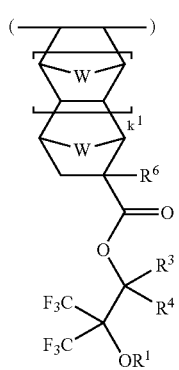
(1b)

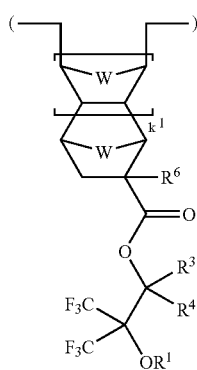
(1c)

Herein $R^1$, $R^3$ to $R^6$, W and $k^1$ are as defined above.

The recurring units derived from the fluorinated monomers of formulas (9) and (10) include those having the general formulas (2a) to (2c).

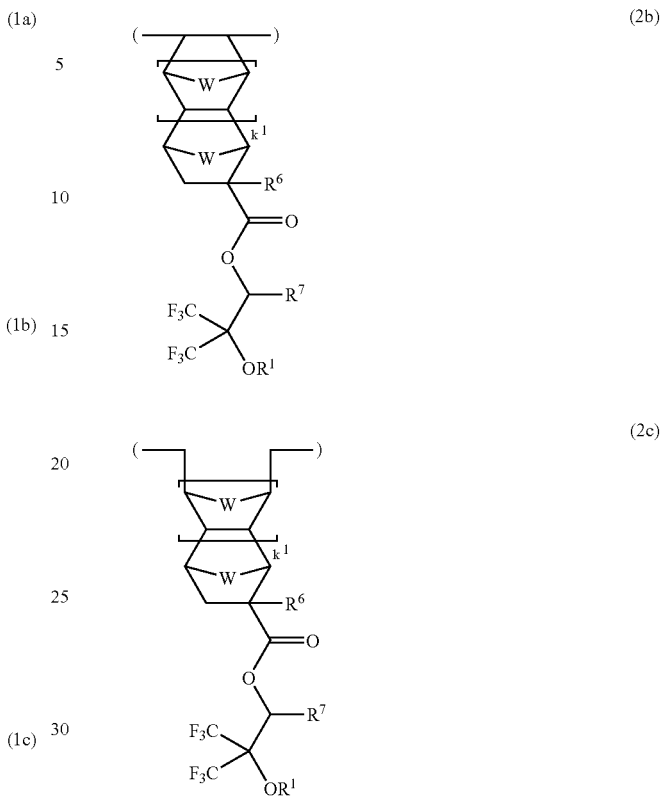

(2a)

(2b)

(2c)

Herein $R^1$, $R^5$ to $R^7$, W and $k^1$ are as defined above.

The recurring units derived from the fluorinated monomers of formulas (13) and (14) include those having the general formulas (3a) to (3c).

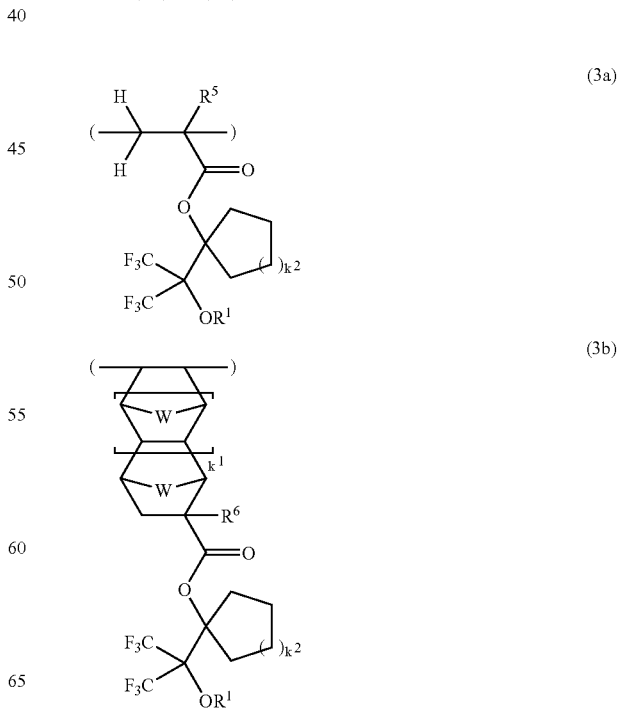

(3a)

(3b)

-continued

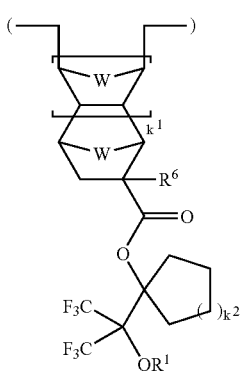
(3c)

Herein $R^1$, $R^5$, $R^6$, W, $k^1$ and $k^2$ are as defined above.

The recurring units derived from the fluorinated monomers of formulas (17) and (18) include those having the general formulas (4a) to (4c).

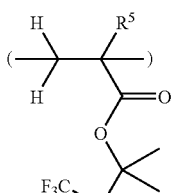
(4a)

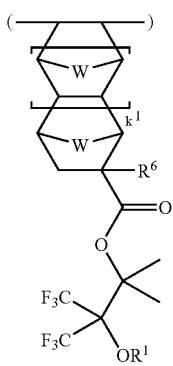
(4b)

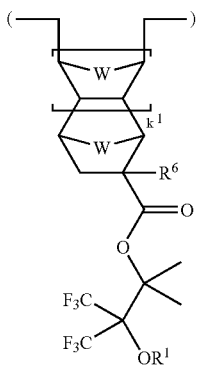
(4c)

Herein $R^1$, $R^5$, $R^6$, W and $k^1$ are as defined above.

In addition to the recurring units derived from the compounds having formulas (5), (6), (9), (10), (13), (14), (17), and (18) such as recurring units having formulas (1a) to (1c), (2a) to (2c), (3a) to (3c), and (4a) to (4c), the polymers of the invention may comprise recurring units of at least one type selected from the following general formulas (19) to (22).

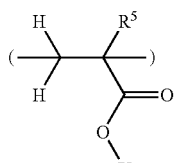
(19)

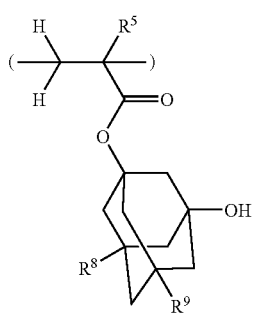
(20)

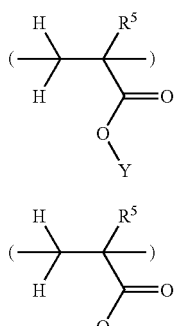
(21)

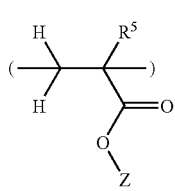
(22)

Herein $R^5$ is as defined above, $R^8$ and $R^9$ are each independently a hydrogen atom or hydroxyl group, X is an acid labile group, Y is a substituent group having a lactone structure, Z is a hydrogen atom, a fluoroalkyl group of 1 to 15 carbon atoms, or a fluoroalcohol-containing substituent group of 1 to 15 carbon atoms.

Under the action of acid, a polymer comprising recurring units of formula (19) is decomposed to generate carboxylic acid, turning to be an alkali soluble polymer. The acid labile group represented by X may be selected from a variety of such groups. Examples of the acid labile group are groups of the following general formulae (L1) to (L4), tertiary alkyl groups of 4 to 20 carbon atoms, preferably 4 to 15 carbon atoms, trialkylsilyl groups in which each alkyl moiety has 1 to 6 carbon atoms, and oxoalkyl groups of 4 to 20 carbon atoms.

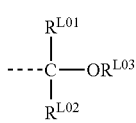
(L1)

-continued

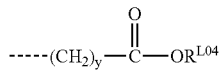
(L2)

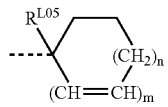
(L3)

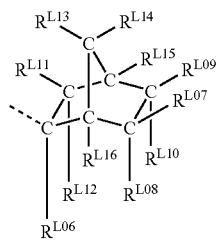
(L4)

In these formulae, the broken line denotes a valence bond. $R^{L01}$ and $R^{L02}$ are hydrogen or straight, branched or cyclic alkyl groups of 1 to 18 carbon atoms, preferably 1 to 10 carbon atoms. Exemplary alkyl groups include methyl, ethyl, propyl, isopropyl, n-butyl, sec-butyl, tert-butyl, cyclopentyl, cyclohexyl, 2-ethylhexyl, n-octyl, norbornyl, tricyclodecanyl, tetracyclododecanyl, and adamantyl. $R^{L03}$ is a monovalent hydrocarbon group of 1 to 18 carbon atoms, preferably 1 to 10 carbon atoms, which may contain a hetero atom such as oxygen, examples of which include unsubstituted straight, branched or cyclic alkyl groups and substituted forms of such alkyl groups in which some hydrogen atoms are replaced by hydroxyl, alkoxy, oxo, amino, alkylamino or the like. Illustrative examples are the substituted alkyl groups shown below.

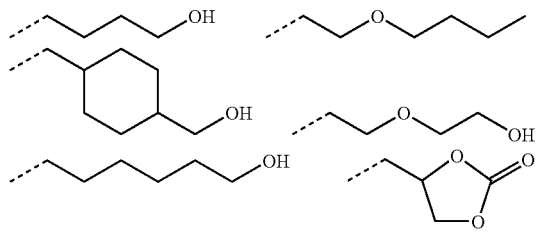

A pair of $R^{L01}$ and $R^{L02}$, $R^{L01}$ and $R^{L03}$, or $R^{L02}$ and $R^{L03}$ may form a ring with carbon and oxygen atoms to which they are attached. Each of $R^{L01}$, $R^{L02}$ and $R^{L03}$ is a straight or branched alkylene group of 1 to 18 carbon atoms, preferably 1 to 10 carbon atoms when they form a ring.

$R^{L04}$ is a tertiary alkyl group of 4 to 20 carbon atoms, preferably 4 to 15 carbon atoms, a trialkylsilyl group in which each alkyl moiety has 1 to 6 carbon atoms, an oxoalkyl group of 4 to 20 carbon atoms, or a group of formula (L1). Exemplary tertiary alkyl groups are tert-butyl, tert-amyl, 1,1-diethylpropyl, 2-cyclopentylpropan-2-yl, 2-cyclohexylpropan-2-yl, 2-(bicyclo[2.2.1]heptan-2-yl)propan-2-yl, 2-(adamantan-1-yl)propan-2-yl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, and 2-ethyl-2-adamantyl. Exemplary trialkylsilyl groups are trimethylsilyl, triethylsilyl, and dimethyl-tert-butylsilyl. Exemplary oxoalkyl groups are 3-oxocyclohexyl, 4-methyl-2-oxooxan-4-yl, and 5-methyl-2-oxooxolan-5-yl. Letter y is an integer of 0 to 6.

In formula (L3), $R^{L05}$ is a substituted or unsubstituted, straight, branched or cyclic alkyl group of 1 to 8 carbon atoms or a substituted or unsubstituted aryl group of 6 to 20 carbon atoms. Examples of the optionally substituted alkyl group include straight, branched or cyclic alkyl groups such as methyl, ethyl, n-propyl, isopropyl, n-butyl, sec-butyl, tert-butyl, tert-amyl, n-pentyl, n-hexyl, cyclopentyl, and cyclohexyl, and substituted forms of such groups in which some hydrogen atoms are substituted by hydroxyl, alkoxy, carboxy, alkoxycarbonyl, oxo, amino, alkylamino, cyano, mercapto, alkylthio, sulfo or other groups. Exemplary aryl groups are phenyl, methylphenyl, naphthyl, anthryl, phenanthryl, and pyrenyl. Letter m is equal to 0 or 1, n is equal to 0, 1, 2 or 3, and 2m+n is equal to 2 or 3.

In formula (L4), $R^{L06}$ is a substituted or unsubstituted, straight, branched or cyclic alkyl group of 1 to 8 carbon atoms or a substituted or unsubstituted aryl group of 6 to 20 carbon atoms. Examples of these groups are the same as exemplified for $R^{L05}$. $R^{L07}$ to $R^{L16}$ independently represent hydrogen or monovalent hydrocarbon groups of 1 to 15 carbon atoms. Exemplary hydrocarbon groups are straight, branched or cyclic alkyl groups such as methyl, ethyl, n-propyl, isopropyl, n-butyl, sec-butyl, tert-butyl, tert-amyl, n-pentyl, n-hexyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl and cyclohexylbutyl, and substituted forms of these groups in which some hydrogen atoms are replaced by hydroxyl, alkoxy, carboxy, alkoxycarbonyl, oxo, amino, alkylamino, cyano, mercapto, alkylthio, sulfo or other groups. Alternatively, $R^{L07}$ to $R^{L16}$, taken together, form a ring (for example, a pair of $R^{L07}$ and $R^{L08}$, $R^{L07}$ and $R^{L09}$, $R^{L08}$ and $R^{L10}$, $R^{L09}$ and $R^{L10}$, $R^{L11}$ and $R^{L12}$, $R^{L13}$ and $R^{L14}$, or a similar pair form a ring). Each of $R^{L07}$ to $R^{L16}$ represents a divalent $C_1$-$C_{15}$ hydrocarbon group when they form a ring, examples of which are the ones exemplified above for the monovalent hydrocarbon groups, with one hydrogen atom being eliminated. Two of $R^{L07}$ to $R^{L16}$ which are attached to adjoining carbon atoms (for example, a pair of $R^{L07}$ and $R^{L09}$, $R^{L09}$ and $R^{L15}$, $R^{L13}$ and $R^{L15}$, or a similar pair) may bond together directly to form a double bond.

Of the acid labile groups of formula (L1), the straight and branched ones are exemplified by the following groups.

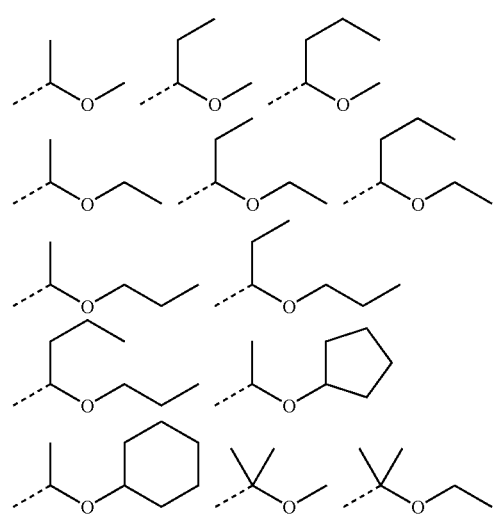

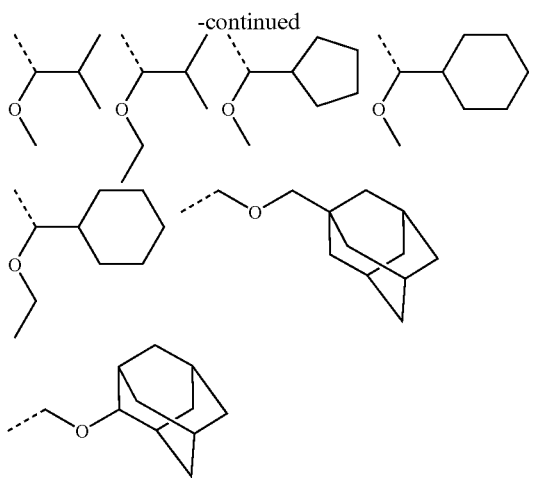

Of the acid labile groups of formula (L1), the cyclic ones are, for example, tetrahydrofuran-2-yl, 2-methyltetrahydrofuran-2-yl, tetrahydropyran-2-yl, and 2-methyltetrahydropyran-2-yl.

Examples of the acid labile groups of formula (L2) include tert-butoxycarbonyl, tert-butoxycarbonylmethyl, tert-amyloxycarbonyl, tert-amyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl groups.

Examples of the acid labile groups of formula (L3) include 1-methylcyclopentyl, 1-ethylcyclopentyl, 1-n-propylcyclopentyl, 1-isopropylcyclopentyl, 1-n-butylcyclopentyl, 1-sec-butylcyclopentyl, 1-cyclohexylcyclopentyl, 1-(4-methoxy-n-butyl)cyclopentyl, 1-methylcyclohexyl, 1-ethylcyclohexyl, 3-methyl-1-cyclopenten-3-yl, 3-ethyl-1-cyclopenten-3-yl, 3-methyl-1-cyclohexen-3-yl, and 3-ethyl-1-cyclohexen-3-yl groups.

Of the acid labile groups having formula (L4), groups having the following formulas (L4-1) to (L4-4) are preferred.

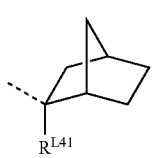

(L4-1)

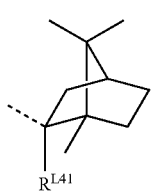

(L4-2)

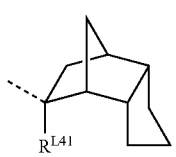

(L4-3)

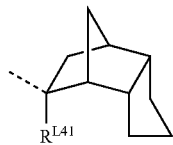

(L4-4)

In formulas (L4-1) to (L4-4), the broken line denotes a bonding site and direction. $R^{L41}$ is each independently a monovalent hydrocarbon group, typically a straight, branched or cyclic alkyl group of 1 to 10 carbon atoms, such as methyl, ethyl, propyl, isopropyl, n-butyl, sec-butyl, tert-butyl, tert-amyl, n-pentyl, n-hexyl, cyclopentyl and cyclohexyl.

For formulas (L4-1) to (L4-4), there can exist enantiomers and diastereomers. Each of formulae (L4-1) to (L4-4) collectively represents all such stereoisomers. Such stereoisomers may be used alone or in admixture.

For example, the general formula (L4-3) represents one or a mixture of two or more selected from groups having the following general formulas (L4-3-1) and (L4-3-2).

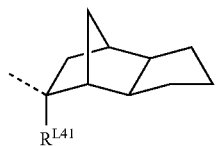

(L4-3-1)

(L4-3-2)

Similarly, the general formula (L4-4) represents one or a mixture of two or more selected from groups having the following general formulas (L4-4-1) to (L4-4-4).

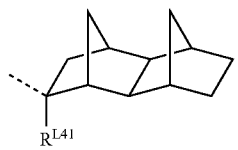

(L4-4-1)

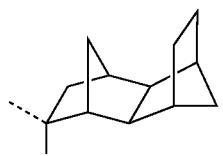

(L4-4-2)

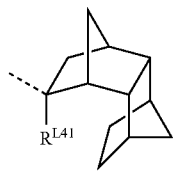

(L4-4-3)

-continued (L4-4-4)

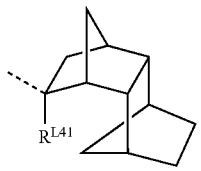

Each of formulas (L4-1) to (L4-4), (L4-3-1) and (L4-3-2), and (L4-4-1) to (L4-4-4) collectively represents an enantiomer thereof and a mixture of enantiomers.

It is noted that in the above formulas (L4-1) to (L4-4), (L4-3-1) and (L4-3-2), and (L4-4-1) to (L4-4-4), the bond direction is on the exo side relative to the bicyclo[2.2.1]heptane ring, which ensures high reactivity for acid catalyzed elimination reaction (see JP-A 2000-336121). In preparing these monomers having a tertiary exo-alkyl group of bicyclo[2.2.1]heptane skeleton as a substituent group, there may be contained monomers substituted with an endo-alkyl group as represented by the following formulas (L4-1-endo) to (L4-4-endo). For good reactivity, an exo proportion of at least 50 mol % is preferred, with an exo proportion of at least 80 mol % being more preferred.

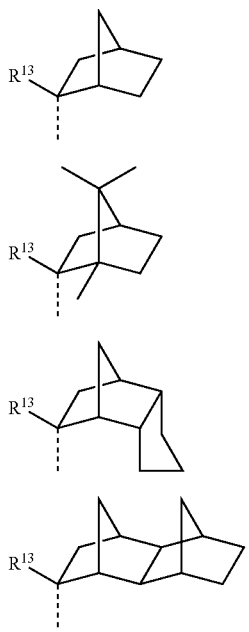

(L4-1-endo)

(L4-2-endo)

(L4-3-endo)

(L4-4-endo)

(See JP-A 2000-336121.)

Illustrative examples of the acid labile group of formula (L4) are given below

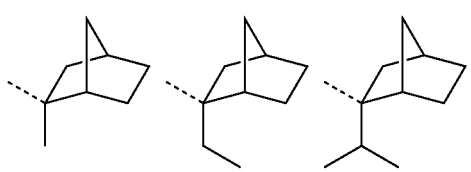

-continued

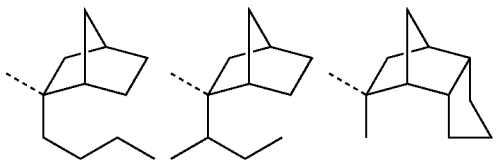

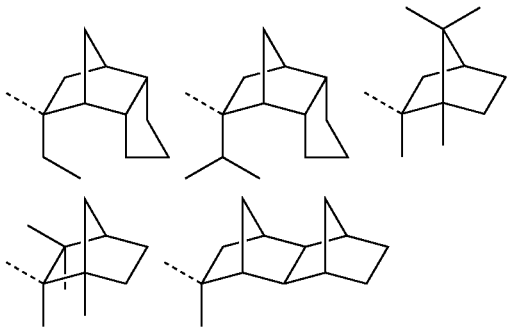

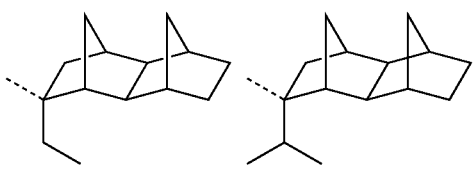

Examples of the tertiary alkyl groups of 4 to 20 carbon atoms, trialkylsilyl groups in which each alkyl moiety has 1 to 6 carbon atoms, and oxoalkyl groups of 4 to 20 carbon atoms are as exemplified for $R^{LO4}$.

Illustrative, non-limiting examples of the recurring units of formula (19) are given below.

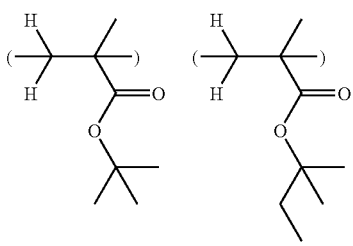

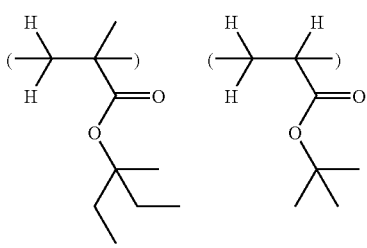

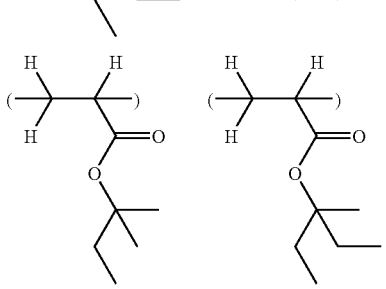

-continued
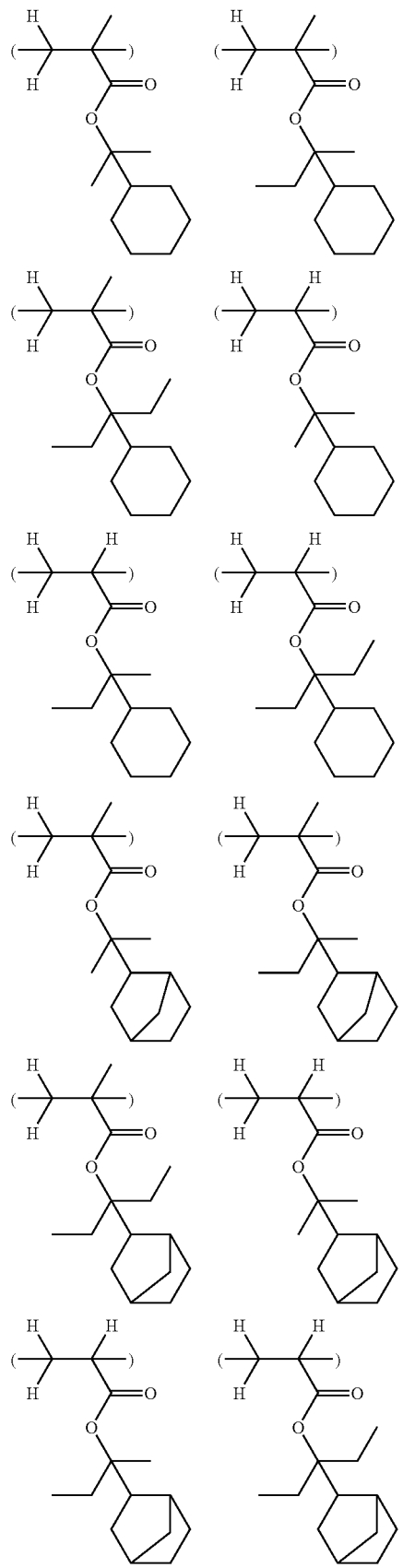
-continued
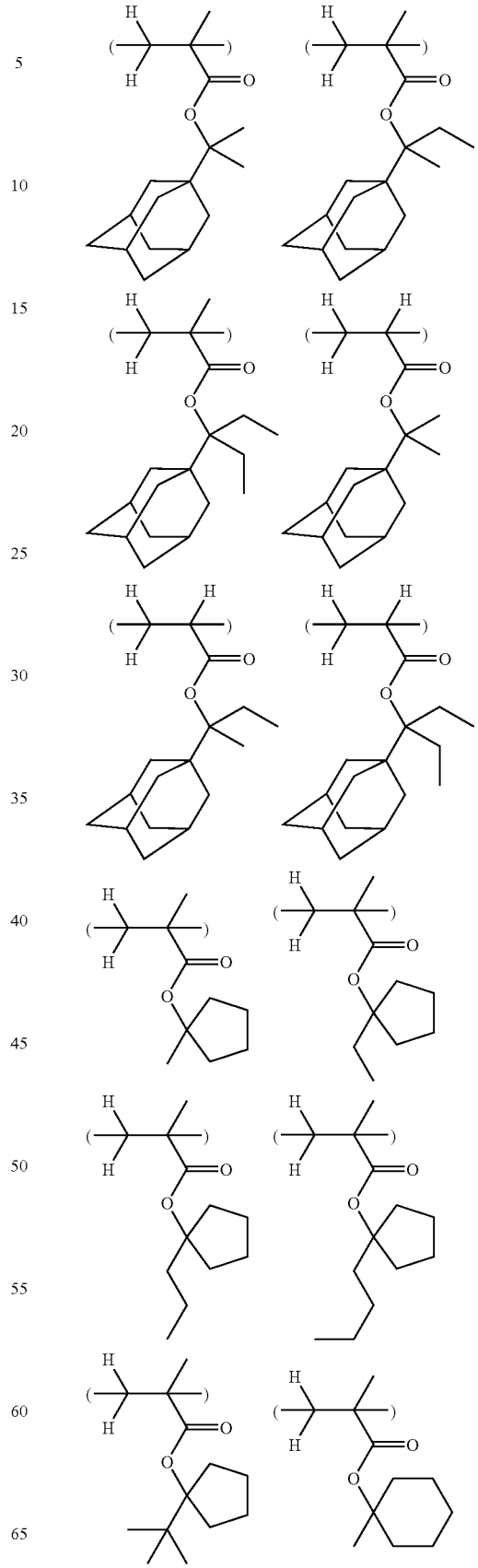

-continued
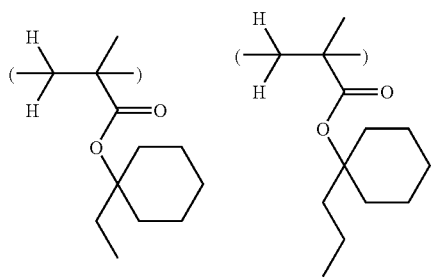
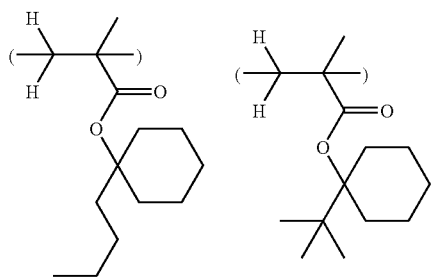
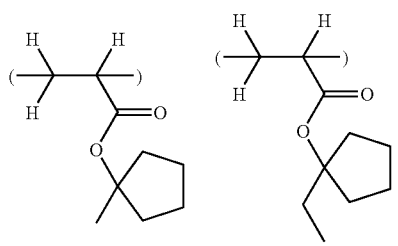
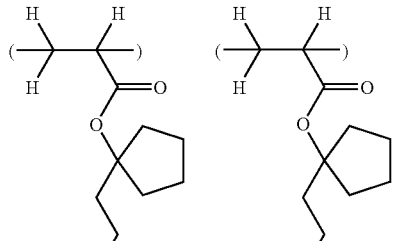
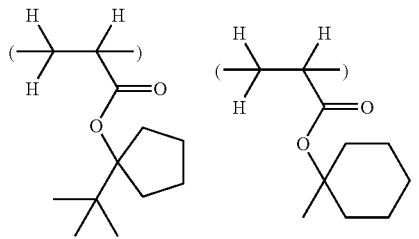
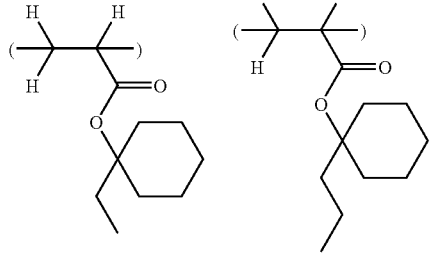
-continued
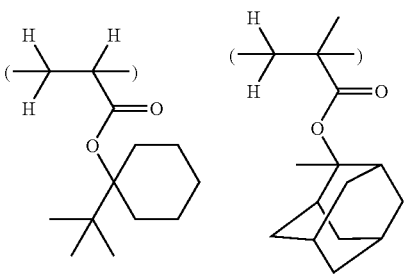
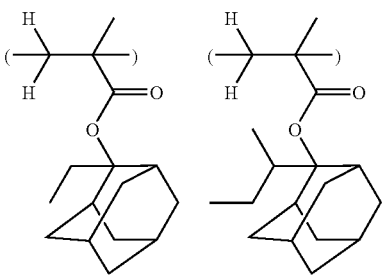
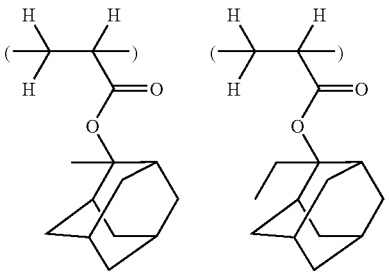
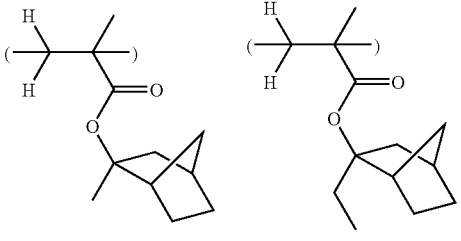
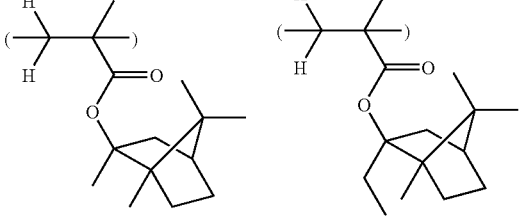
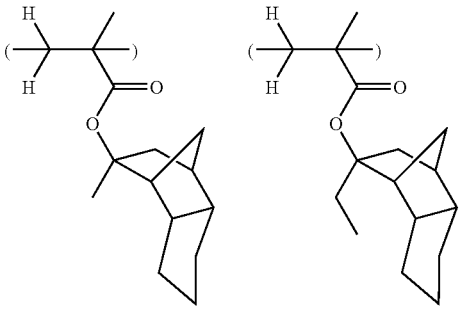

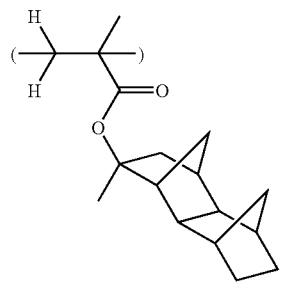
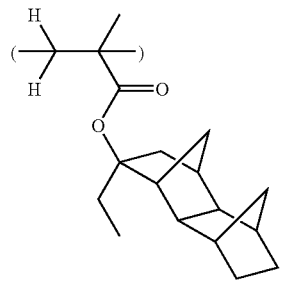
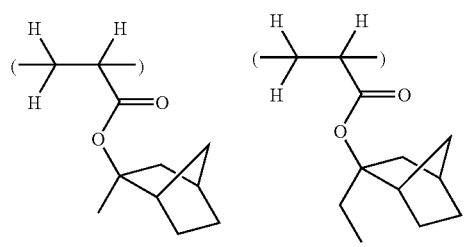
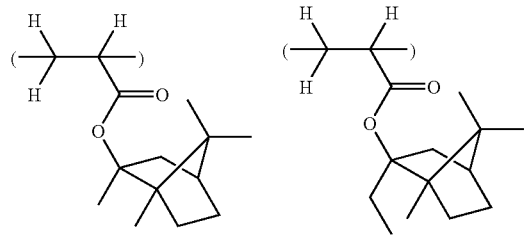
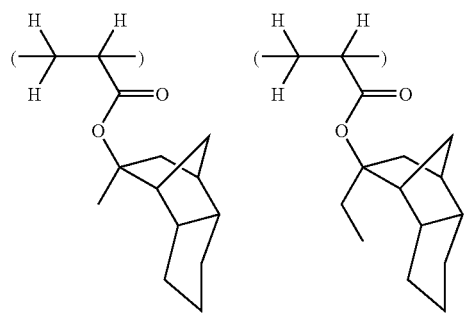
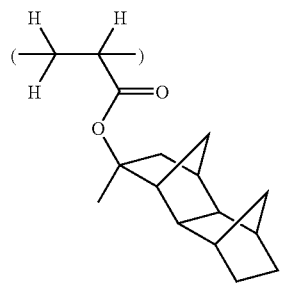
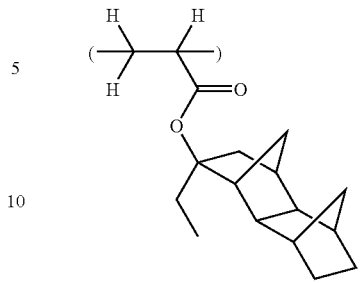
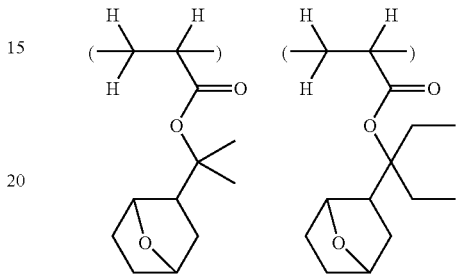
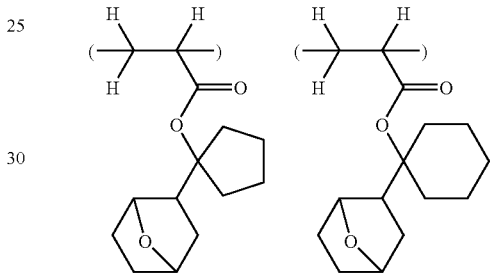
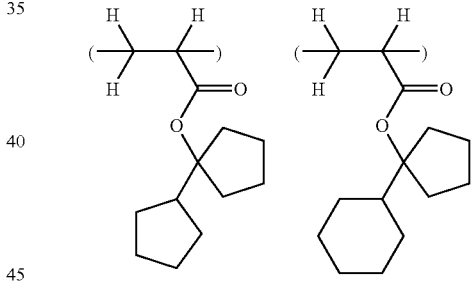
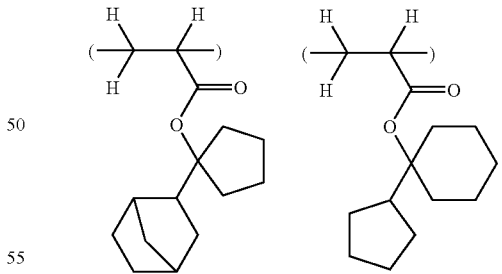
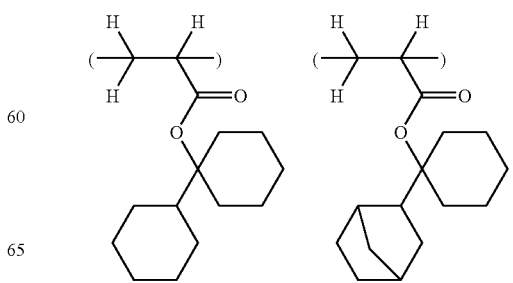

-continued
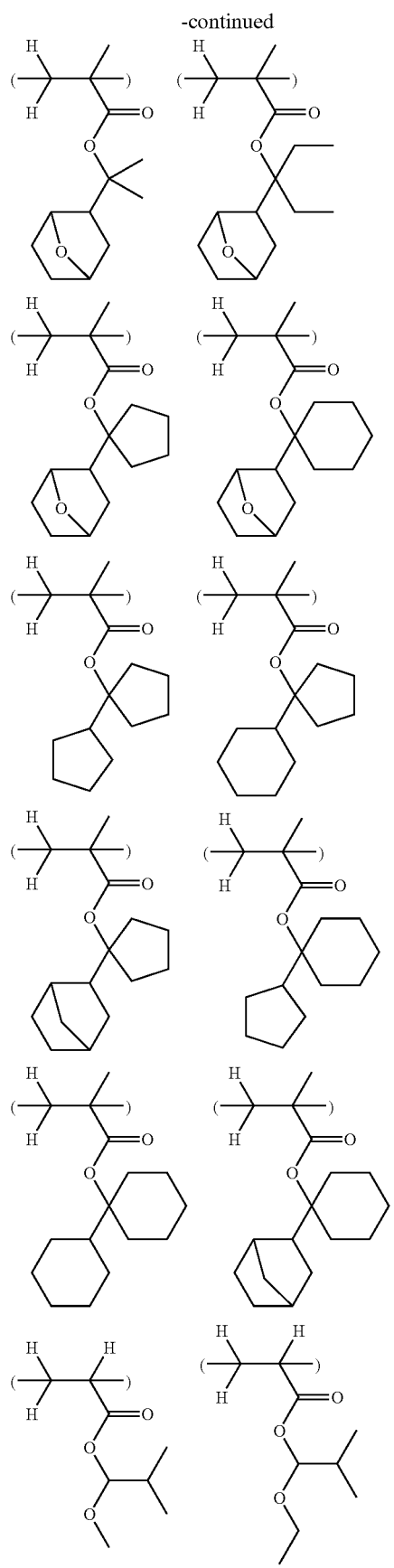
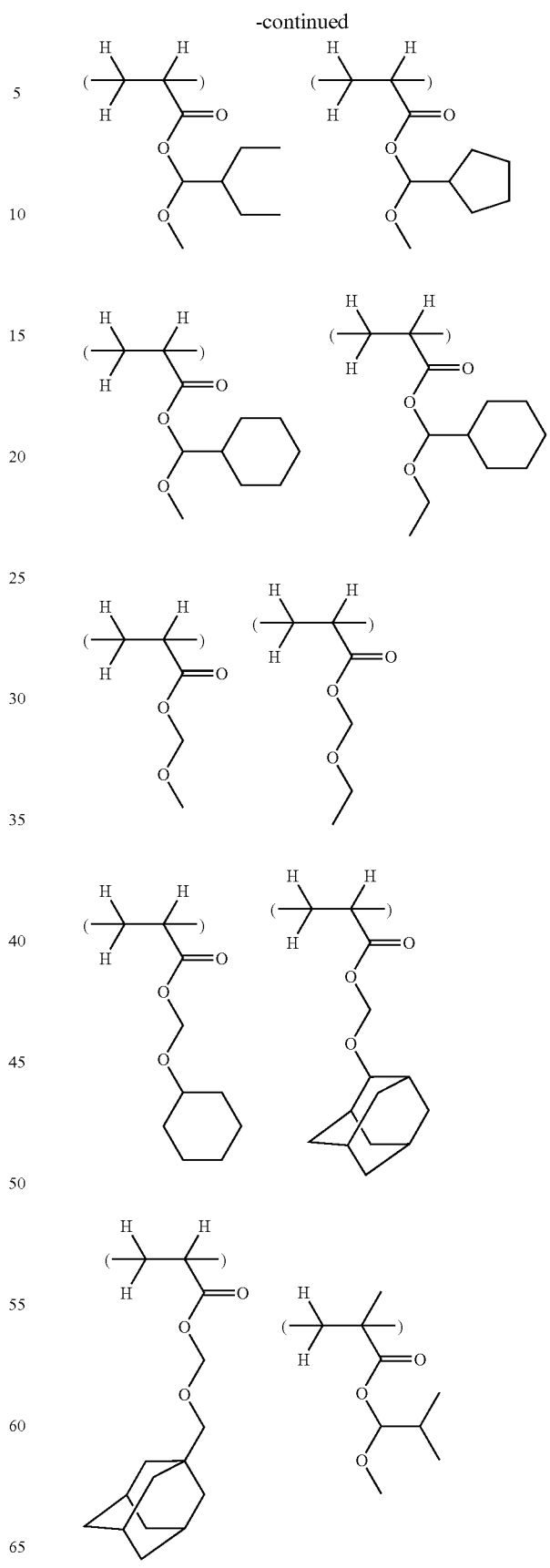

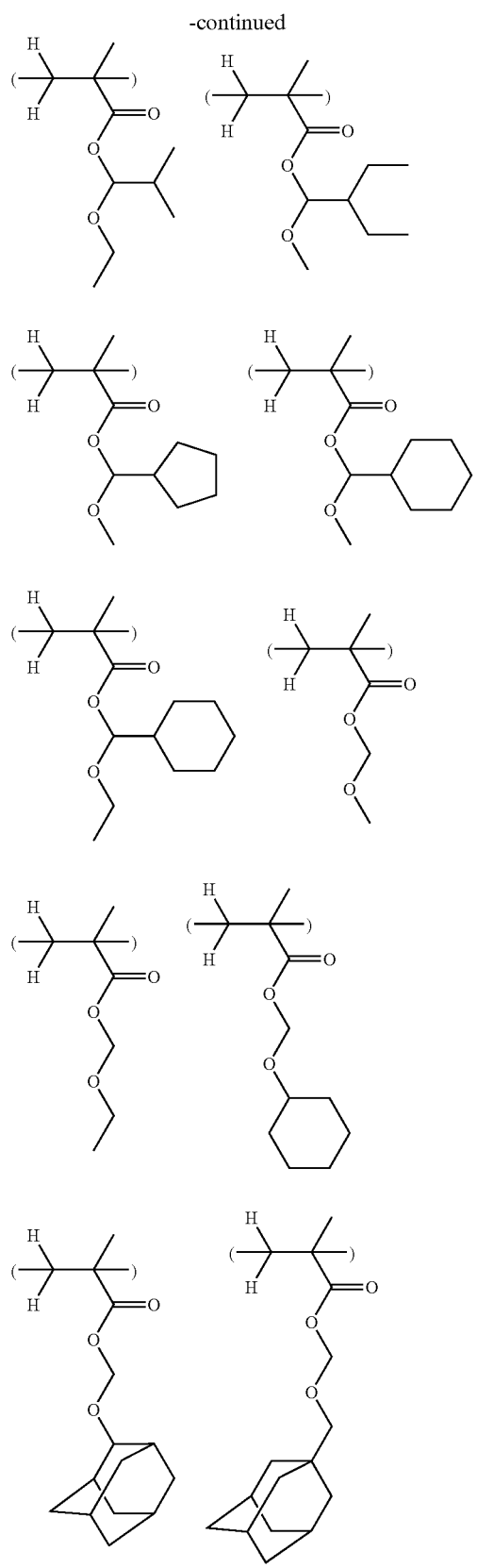
Illustrative, non-limiting examples of the recurring units of formula (20) are given below.
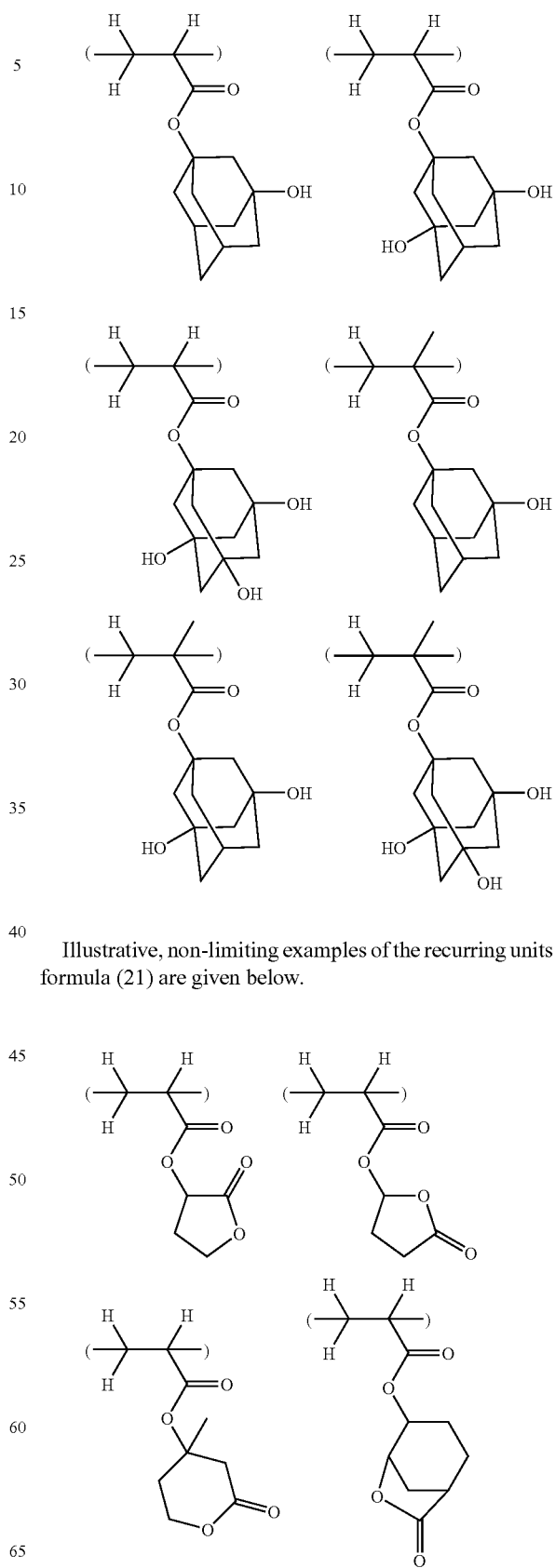
Illustrative, non-limiting examples of the recurring units of formula (21) are given below.

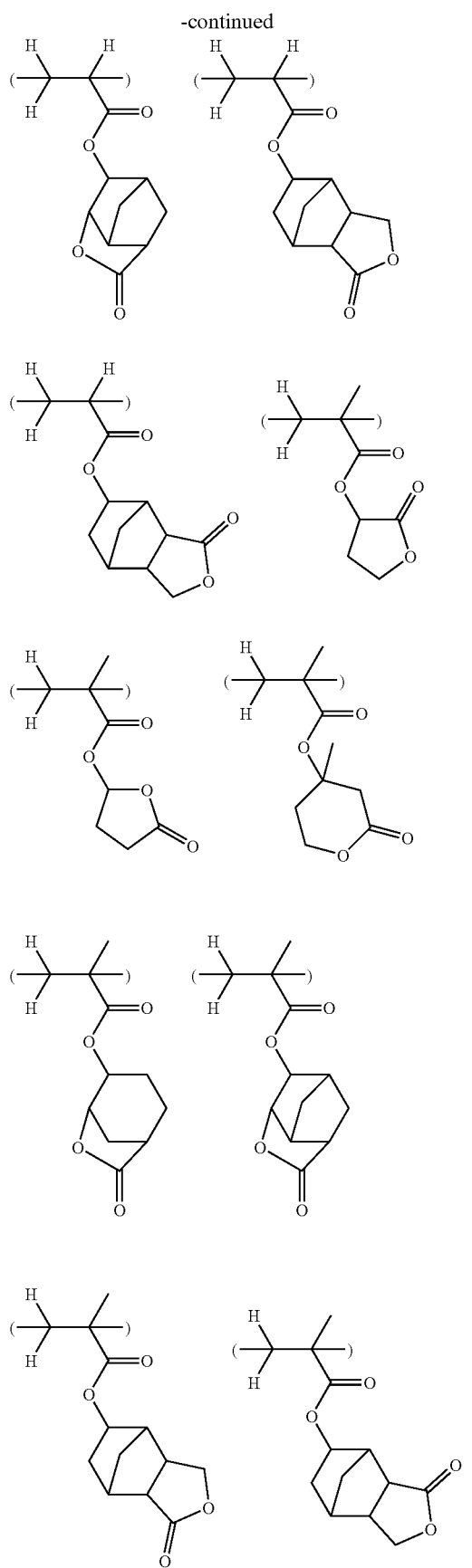
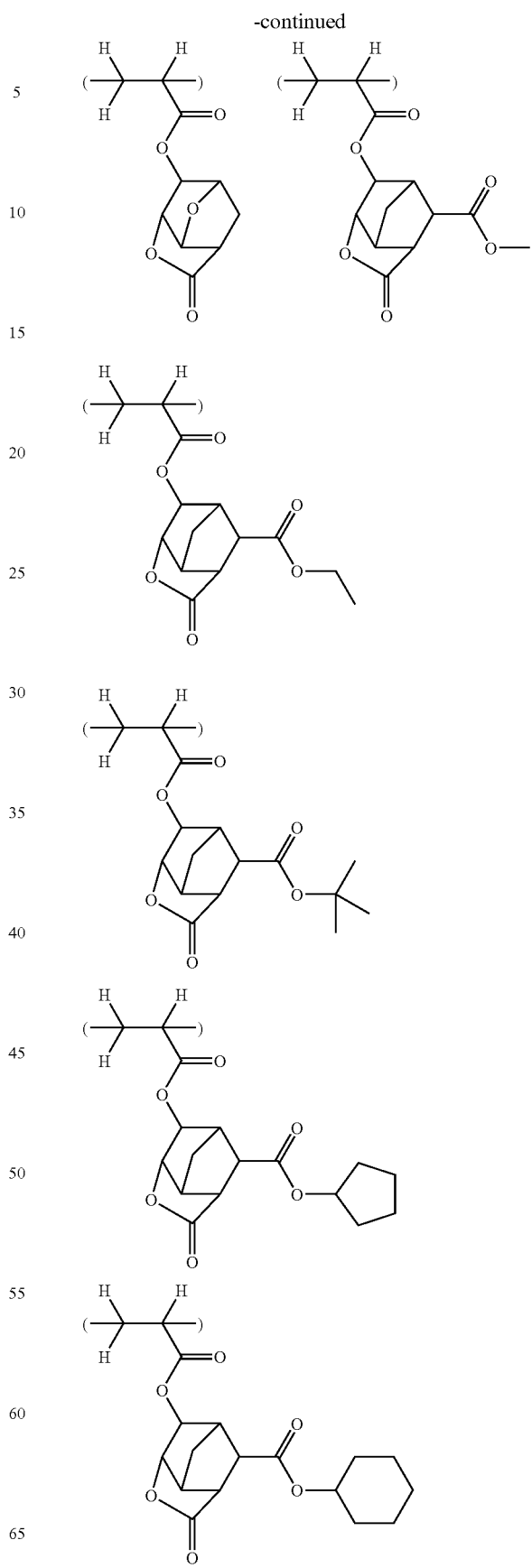

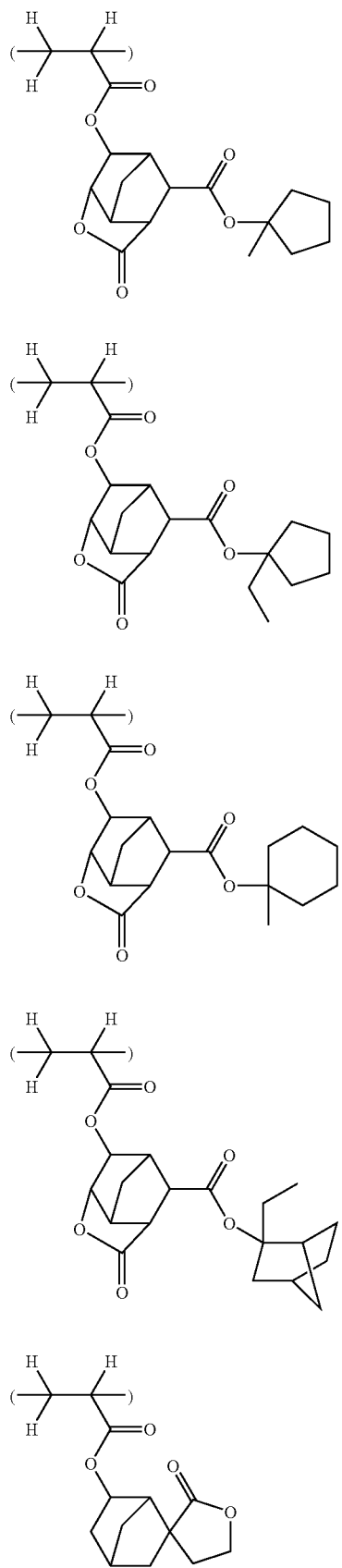
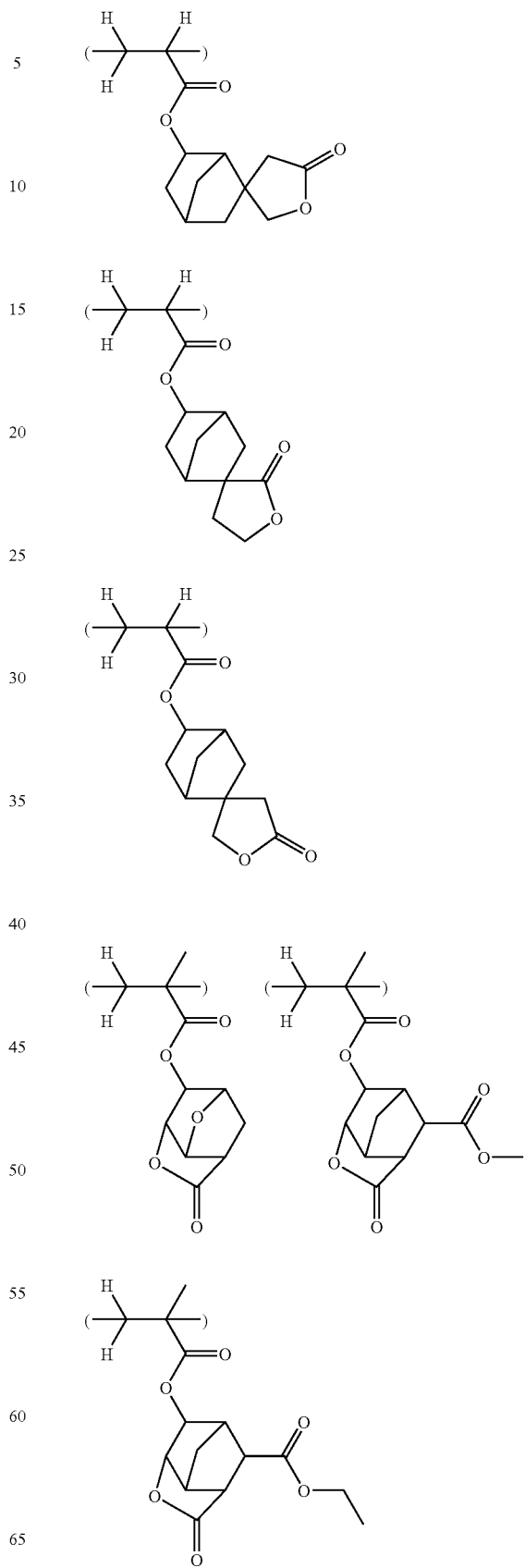

-continued
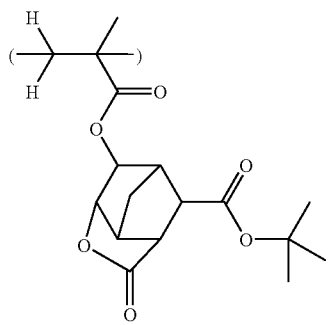
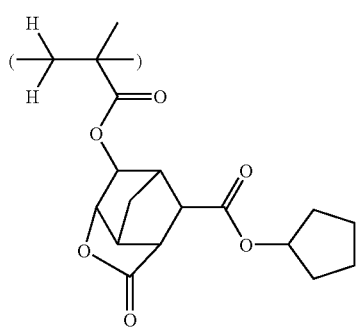
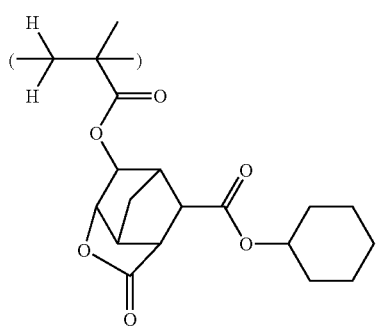
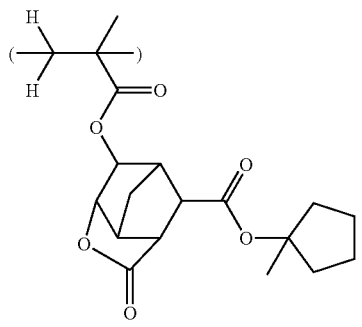
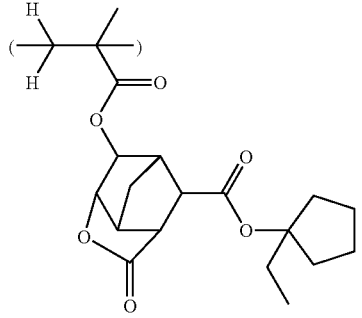
-continued
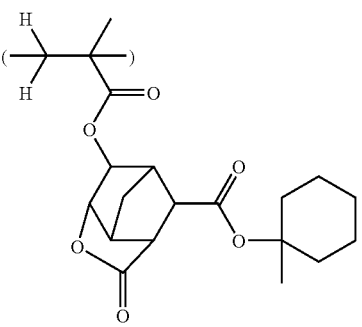
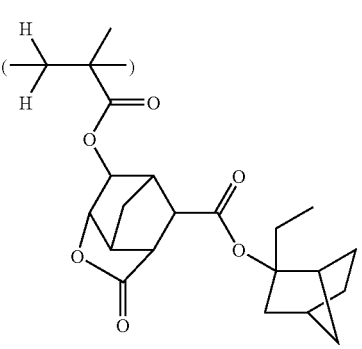
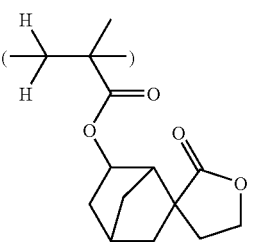
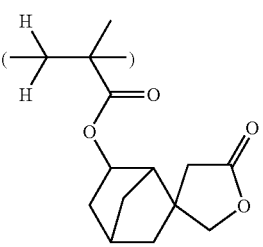
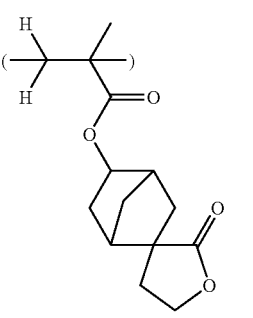

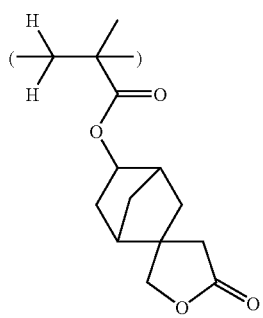
Illustrative, non-limiting examples of the recurring units of formula (22) are given below.
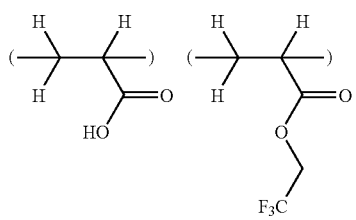
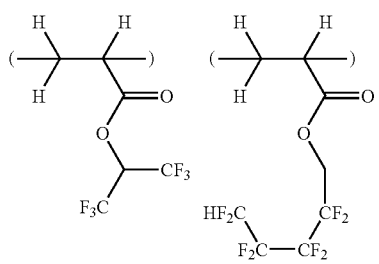
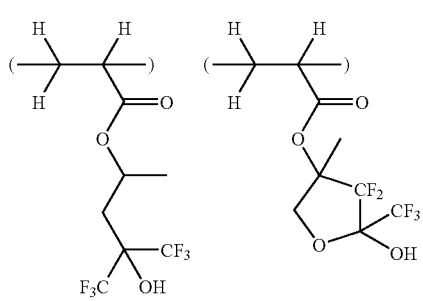
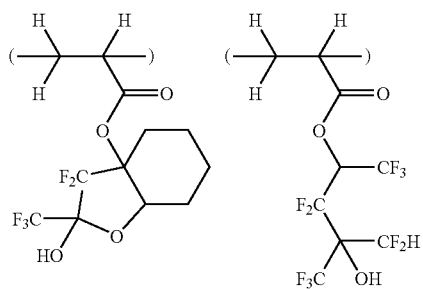
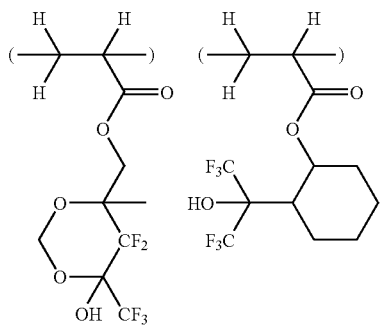
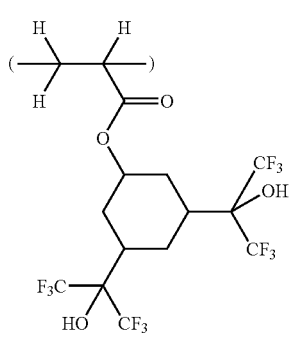
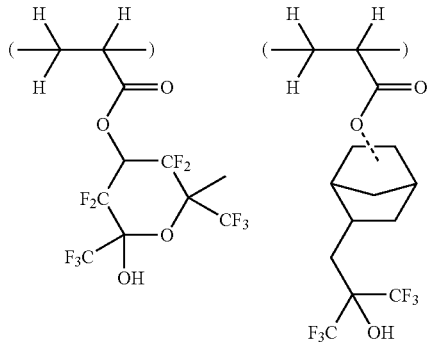
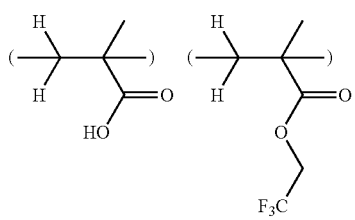
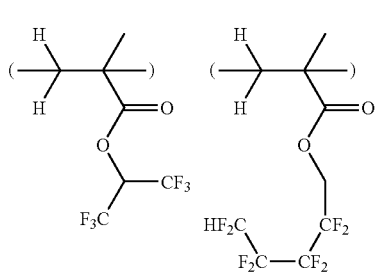

-continued

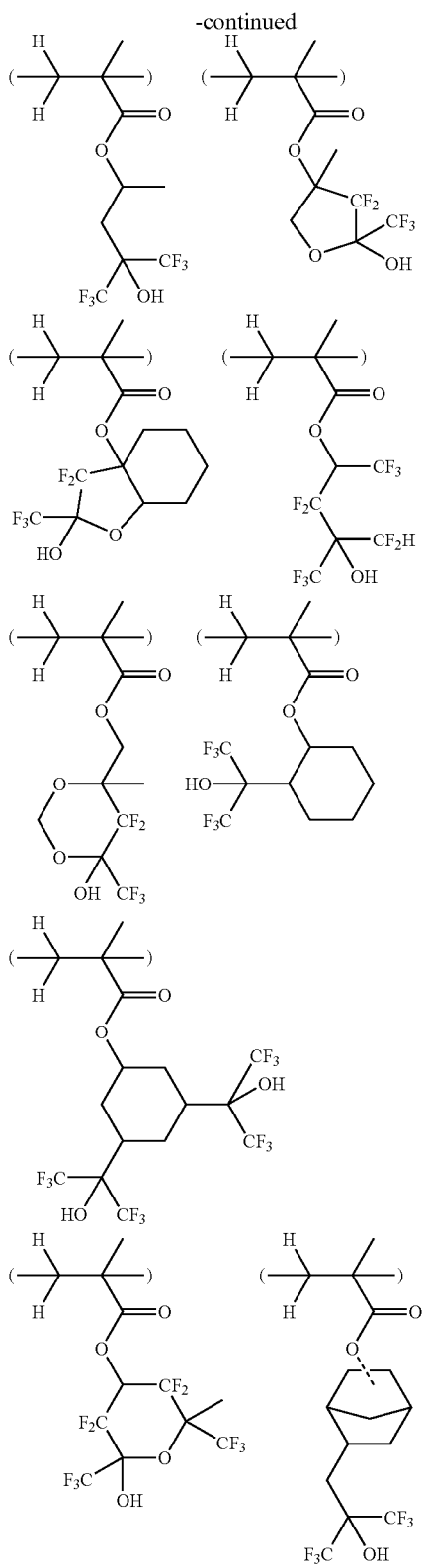

In addition to the foregoing units, the polymers of the invention may further comprise recurring units derived from carbon-to-carbon double bond-bearing monomers other than the above-described ones, for example, substituted acrylic acid esters such as methyl methacrylate, methyl crotonate, dimethyl maleate and dimethyl itaconate, unsaturated carboxylic acids such as maleic acid, fumaric acid, and itaconic acid, cyclic olefins such as norbornene, norbornene derivatives, and tetracyclo[4.4.0.1$^{2,5}$.1$^{7,10}$]dodecene derivatives, unsaturated acid anhydrides such as itaconic anhydride, and other monomers.

The polymers of the invention generally have a weight average molecular weight (Mw) of 1,000 to 500,000, and preferably 3,000 to 100,000, as measured by gel permeation chromatography (GPC) using polystyrene standards. Outside the range, there may result an extreme drop of etch resistance, and a drop of resolution due to difficulty to gain a dissolution rate difference before and after exposure.

In the inventive polymers, appropriate proportions of the respective recurring units derived from the monomers are given below although the invention is not limited thereto. The inventive polymers may contain:

(I) constituent units of one or more types having formulas (1a) to (1c), (2a) to (2c), (3a) to (3c), and (4a) to (4c) derived from monomers of formulas (5), (6), (9), (10), (13), (14), (17), and (18) in a proportion of more than 0 mol % to 100 mol %, preferably 5 to 70 mol %, and more preferably 10 to 50 mol %, (II) constituent units of one or more types having formulas (19) to (22) in a proportion of 0 mol % to less than 100 mol %, preferably 1 to 95 mol %, and more preferably 20 to 80 mol %, and (III) constituent units of one or more types derived from other monomers in a proportion of 0 to 80 mol %, preferably 0 to 70 mol %, and more preferably 0 to 50 mol %, based on the total moles of constituent units.

The polymers of the invention are prepared by copolymerization reaction using the compound of formula (5), (6), (9), (10), (13), (14), (17) or (18) as a first monomer and polymerizable double bond-bearing compounds as second and subsequent monomers.

The copolymerization reaction to produce the inventive polymers may be performed in various modes, preferably radical polymerization, anionic polymerization or coordination polymerization.

For radical polymerization, preferred reaction conditions include (a) a solvent selected from among hydrocarbons such as benzene, ethers such as tetrahydrofuran, alcohols such as ethanol, and ketones such as methyl isobutyl ketone, (b) a polymerization initiator selected from azo compounds such as 2,2'-azobisisobutyronitrile and peroxides such as benzoyl peroxide and lauroyl peroxide, (c) a temperature of about 0° C. to about 100° C., and (d) a time of about 0.5 to about 48 hours. Reaction conditions outside the described range may be employed if desired.

For anionic polymerization, preferred reaction conditions include (a) a solvent selected from among hydrocarbons such as benzene, ethers such as tetrahydrofuran, and liquid ammonia, (b) a polymerization initiator selected from metals such as sodium and potassium, alkyl metals such as n-butyllithium and sec-butyllithium, ketyl, and Grignard reagents, (c) a temperature of about −78° C. to about 0° C., (d) a time of about 0.5 to about 48 hours, and (e) a stopper selected from among proton-donative compounds such as methanol, halides such as methyl iodide, and electrophilic compounds. Reaction conditions outside the described range may be employed if desired.

For coordination polymerization, preferred reaction conditions include (a) a solvent selected from among hydrocarbons such as n-heptane and toluene, (b) a catalyst selected from Ziegler-Natta catalysts comprising a transition metal (e.g., titanium) and alkylaluminum, Phillips catalysts of metal oxides having chromium or nickel compounds carried thereon, and olefin-metathesis mixed catalysts as typified by tungsten and rhenium mixed catalysts, (c) a temperature of about 0° C. to about 100° C., and (d) a time of about 0.5 to about 48 hours. Reaction conditions outside the described range may be employed if desired.

Resist Composition

Since the polymer of the invention is useful as the base resin of a resist composition, the other aspect of the invention provides a resist composition comprising the polymer and specifically a chemically amplified positive resist composition comprising the polymer. Typically, the resist composition contains (A) the inventive polymer as a base resin, (B) an acid generator, (C) an organic solvent, and optionally (D) an organic nitrogen-containing compound and (E) a surfactant.

In addition to the inventive polymer, the base resin (A) may include another polymer having a dissolution rate in alkaline developer that increases under the action of acid, if necessary. Examples of the other polymer include, but are not limited to, (i) poly(meth)acrylic acid derivatives, (ii) norbornene derivative-maleic anhydride copolymers, (iii) hydrogenated products of ring-opening metathesis polymers, and (iv) vinyl ether-maleic anhydride-(meth)acrylic acid derivative copolymers.

Of these, the hydrogenated products of ring-opening metathesis polymers are synthesized by the method illustrated in JP-A 2003-66612. Illustrative examples of such hydrogenated polymers include those polymers having the recurring units shown below, but are not limited thereto.

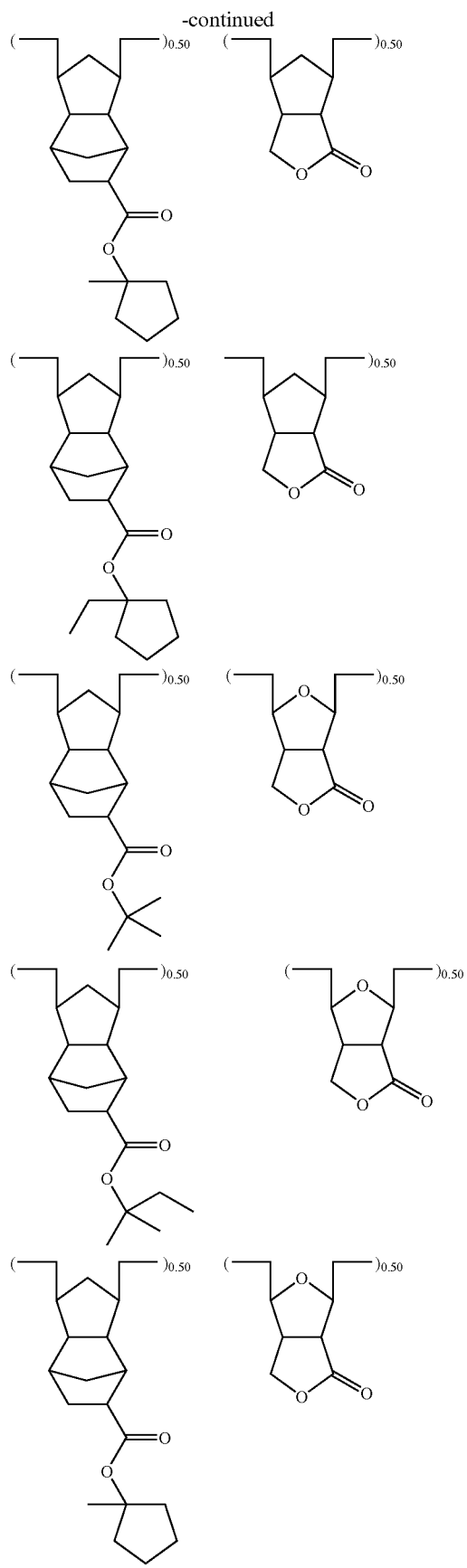

-continued
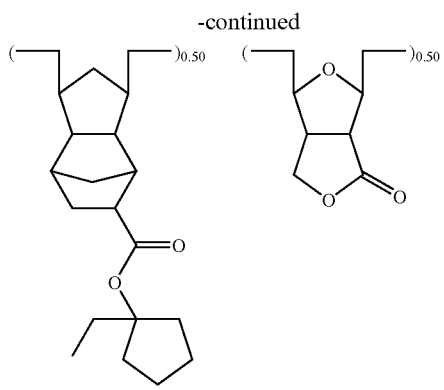
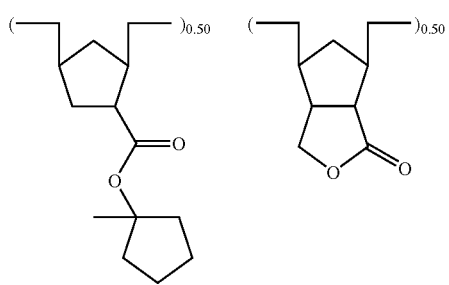
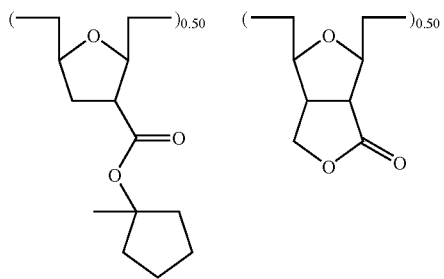
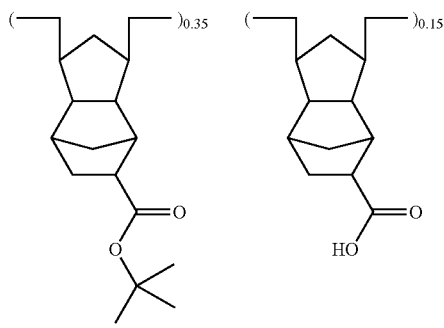
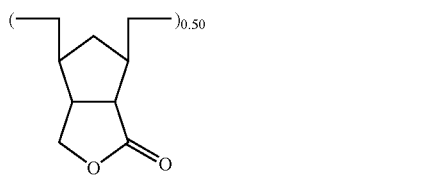
-continued
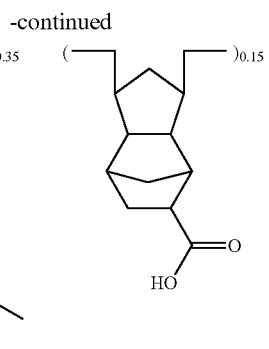
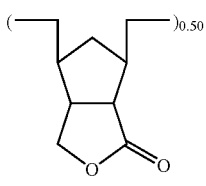
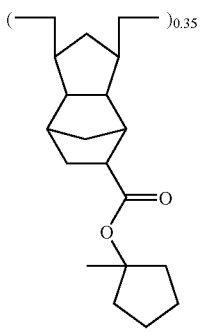
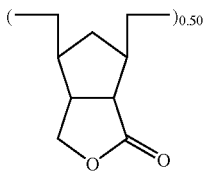

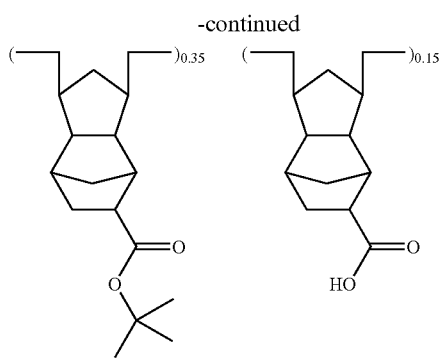
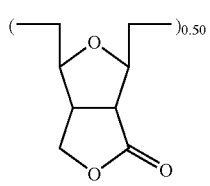
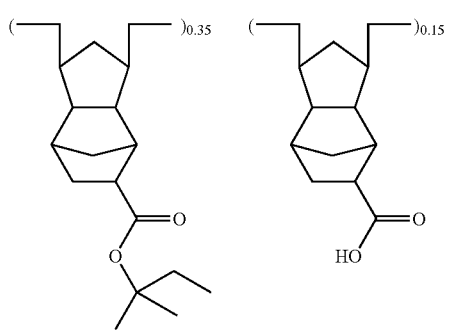
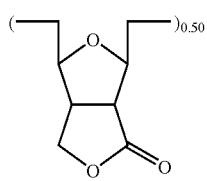
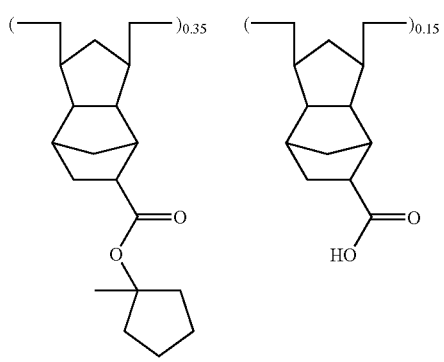
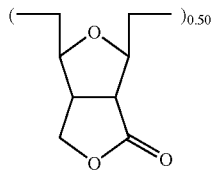

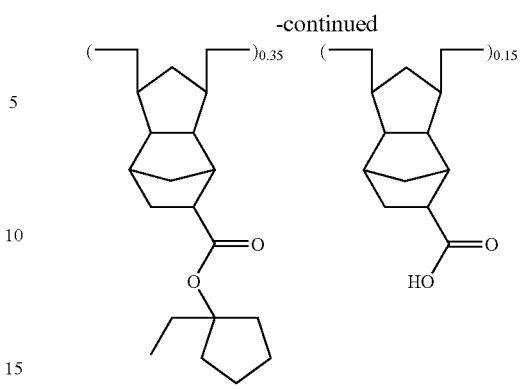
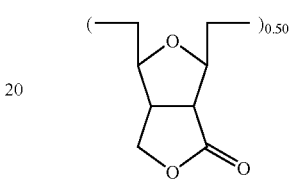
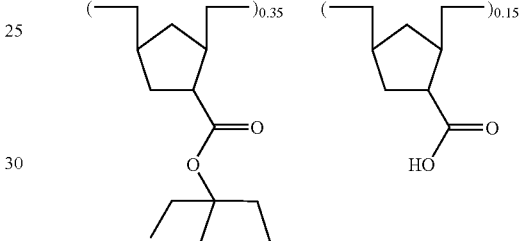
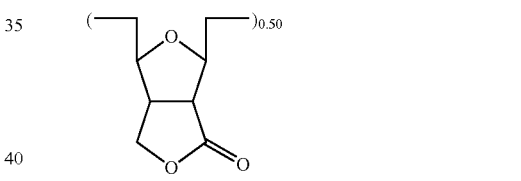
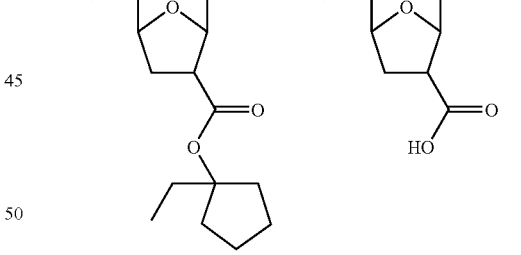
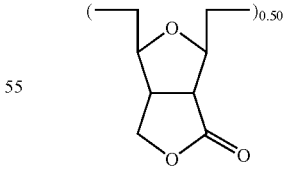

The inventive polymer and the other polymer are preferably blended in a weight ratio from 100:0 to 10:90, more preferably from 100:0 to 20:80. If the blend ratio of the inventive polymer is below this range, the resist composition would become poor in some of the desired properties. The properties of the resist composition can be adjusted by properly changing the blend ratio of the inventive polymer.

The other polymer is not limited to one type and a mixture of two or more other polymers may be added. The use of plural polymers allows for easy adjustment of resist properties.

Acid Generator

As the acid generator (B), a photoacid generator (PAG) is typically used. It is any compound capable of generating an acid upon exposure to high-energy radiation. Suitable photoacid generators include sulfonium salts, iodonium salts, sulfonyldiazomethane, N-sulfonyloxyimide, and oxime-O-sulfonate acid generators. Exemplary acid generators are given below while they may be used alone or in admixture of two or more.

Sulfonium salts are salts of sulfonium cations with sulfonates, bis(substituted alkylsulfonyl)imides and tris(substituted alkylsulfonyl)methides. Exemplary sulfonium cations include triphenylsulfonium, (4-tert-butoxyphenyl)diphenylsulfonium, bis(4-tert-butoxyphenyl)phenylsulfonium, tris(4-tert-butoxyphenyl)sulfonium, (3-tert-butoxyphenyl)diphenylsulfonium, bis(3-tert-butoxyphenyl)phenylsulfonium, tris(3-tert-butoxyphenyl)sulfonium, (3,4-di-tert-butoxyphenyl)diphenylsulfonium, bis(3,4-di-tert-butoxyphenyl)phenylsulfonium, tris(3,4-di-tert-butoxyphenyl)sulfonium, diphenyl(4-thiophenoxyphenyl)sulfonium, (4-tert-butoxycarbonylmethyloxyphenyl)diphenylsulfonium, tris(4-tert-butoxycarbonylmethyloxyphenyl)sulfonium, (4-tert-butoxyphenyl)bis(4-dimethylaminophenyl)sulfonium, tris(4-dimethylaminophenyl)sulfonium, 2-naphthyldiphenylsulfonium, dimethyl-2-naphthylsulfonium, 4-hydroxyphenyldimethylsulfonium, 4-methoxyphenyldimethylsulfonium, trimethylsulfonium, 2-oxocyclohexylcyclohexylmethylsulfonium, trinaphthylsulfonium, tribenzylsulfonium, diphenylmethylsulfonium, dimethylphenylsulfonium, 2-oxo-2-phenylethylthiacyclopentanium, 4-n-butoxynaphthyl-1-thiacyclopentanium, and 2-n-butoxynaphthyl-1-thiacyclopentanium. Exemplary sulfonates include trifluoromethanesulfonate, pentafluoroethanesulfonate, nonafluorobutanesulfonate, dodecafluorohexanesulfonate, pentafluoroethylperfluorocyclohexanesulfonate, heptadecafluorooctanesulfonate, 2,2,2-trifluoroethanesulfonate, pentafluorobenzenesulfonate, 4-trifluoromethylbenzenesulfonate, 4-fluorobenzenesulfonate, mesitylenesulfonate, 2,4,6-triisopropylbenzenesulfonate, toluenesulfonate, benzenesulfonate, 4-(4'-toluenesulfonyloxy)benzenesulfonate, naphthalenesulfonate, camphorsulfonate, octanesulfonate, dodecylbenzenesulfonate, butanesulfonate, methanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropanesulfonate, 2-adamantanecarbonyloxy-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-naphthylethanesulfonate, 1,1,2,2-tetrafluoro-2-(norbornan-2-yl)ethanesulfonate, and 1,1,2,2-tetrafluoro-2-(tetracyclo[4.4.0.1$^{2,5}$.1$^{7,10}$]dodec-3-en-8-yl)ethanesulfonate.

Exemplary bis(substituted alkylsulfonyl)imides include bistrifluoromethylsulfonylimide, bispentafluoroethylsulfonylimide, bisheptafluoropropylsulfonylimide, and 1,3-propylenebissulfonylimide. A typical tris(substituted alkylsulfonyl)methide is tristrifluoromethylsulfonylmethide. Sulfonium salts based on combination of the foregoing examples are included.

Iodonium salts are salts of iodonium cations with sulfonates, bis(substituted alkylsulfonyl)imides and tris(substituted alkylsulfonyl)methides. Exemplary iodonium cations are aryliodonium cations including diphenyliodinium, bis(4-tert-butylphenyl)iodonium, 4-tert-butoxyphenylphenyliodonium, and 4-methoxyphenylphenyliodonium. Exemplary sulfonates include trifluoromethanesulfonate, pentafluoroethanesulfonate, nonafluorobutanesulfonate, dodecafluorohexanesulfonate, pentafluoroethylperfluorocyclohexanesulfonate, heptadecafluorooctanesulfonate, 2,2,2-trifluoroethanesulfonate, pentafluorobenzenesulfonate, 4-trifluoromethylbenzenesulfonate, 4-fluorobenzenesulfonate, mesitylenesulfonate, 2,4,6-triisopropylbenzenesulfonate, toluenesulfonate, benzenesulfonate, 4-(4-toluenesulfonyloxy)benzenesulfonate, naphthalenesulfonate, camphorsulfonate, octanesulfonate, dodecylbenzenesulfonate, butanesulfonate, methanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropanesulfonate, 2-adamantanecarbonyloxy-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-naphthylethanesulfonate, 1,1,2,2-tetrafluoro-2-(norbornan-2-yl)ethanesulfonate, and 1,1,2,2-tetrafluoro-2-(tetracyclo[4.4.0.1$^{2,5}$.1$^{7,10}$]dodec-3-en-8-yl)ethanesulfonate.

Exemplary bis(substituted alkylsulfonyl)imides include bistrifluoromethylsulfonylimide, bispentafluoroethylsulfonylimide, bisheptafluoropropylsulfonylimide, and 1,3-propylenebissulfonylimide. A typical tris(substituted alkylsulfonyl)methide is tristrifluoromethylsulfonylmethide. Iodonium salts based on combination of the foregoing examples are included.

Exemplary sulfonyldiazomethane compounds include bissulfonyldiazomethane compounds and sulfonyl-carbonyldiazomethane compounds such as bis(ethylsulfonyl)diazomethane, bis(1-methylpropylsulfonyl)diazomethane, bis(2-methylpropylsulfonyl)diazomethane, bis(1,1-dimethylethylsulfonyl)diazomethane, bis(cyclohexylsulfonyl)diazomethane, bis(perfluoroisopropylsulfonyl)diazomethane, bis(phenylsulfonyl)diazomethane, bis(4-methylphenylsulfonyl)diazomethane, bis(2,4-dimethylphenylsulfonyl)diazomethane, bis(2-naphthylsulfonyl)diazomethane, bis(4-acetyloxyphenylsulfonyl)diazomethane, bis(4-methanesulfonyloxyphenylsulfonyl)diazomethane, bis(4-(4-toluenesulfonyloxy)phenylsulfonyl)diazomethane, bis(4-(n-hexyloxy)phenylsulfonyl)diazomethane, bis(2-methyl-4-(n-hexyloxy)phenylsulfonyl)diazomethane, bis(2,5-dimethyl-4-(n-hexyloxy)phenylsulfonyl)diazomethane, bis(3,5-dimethyl-4-(n-hexyloxy)phenylsulfonyl)diazomethane, bis(2-methyl-5-isopropyl-4-(n-hexyloxy)phenylsulfonyl)diazomethane, 4-methylphenylsulfonylbenzoyldiazomethane, tert-butylcarbonyl-4-methylphenylsulfonyldiazomethane, 2-naphthylsulfonylbenzoyldiazomethane, 4-methylphenylsulfonyl-2-naphthoyldiazomethane, methylsulfonylbenzoyldiazomethane, and tert-butoxycarbonyl-4-methylphenylsulfonyldiazomethane.

N-sulfonyloxyimide photoacid generators include combinations of imide skeletons with sulfonates. Exemplary imide skeletons are succinimide, naphthalene dicarboxylic acid imide, phthalimide, cyclohexyldicarboxylic acid imide, 5-norbornene-2,3-dicarboxylic acid imide, and 7-oxabicyclo [2.2.1]-5-heptene-2,3-dicarboxylic acid imide. Exemplary sulfonates include trifluoromethanesulfonate, pentafluoroethanesulfonate, nonafluorobutanesulfonate, dodecafluorohexanesulfonate, pentafluoroethylperfluorocyclohexanesulfonate, heptadecafluorooctanesulfonate, 2,2,2-trifluoroethanesulfonate, pentafluorobenzenesulfonate, 4-trifluoromethylbenzenesulfonate, 4-fluorobenzenesulfonate, mesitylenesulfonate, 2,4,6-triisopropylbenzenesulfonate, toluenesulfonate, benzenesulfonate, naphthalenesulfonate, camphorsulfonate, octanesulfonate, dodecylbenzenesulfonate, butanesulfonate, methanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropanesulfonate, 2-adamantanecarbonyloxy-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-naphthylethanesulfonate, 1,1,2,2-tetrafluoro-2-(norbornan-2-yl)ethanesulfonate, and 1,1,2,2-tetrafluoro-2-(tetracyclo [4.4.0.1$^{2,5}$.1$^{7,10}$]dodec-3-en-8-yl)ethanesulfonate.

Benzoinsulfonate photoacid generators include benzoin tosylate, benzoin mesylate, and benzoin butanesulfonate.

Pyrogallol trisulfonate photoacid generators include pyrogallol, phloroglucinol, catechol, resorcinol, and hydroquinone, in which all the hydroxyl groups are substituted by trifluoromethanesulfonate, pentafluoroethanesulfonate, nonafluorobutanesulfonate, dodecafluorohexanesulfonate, pentafluoroethylperfluorocyclohexanesulfonate, heptadecafluorooctanesulfonate, 2,2,2-trifluoroethanesulfonate, pentafluorobenzenesulfonate, 4-trifluoromethylbenzenesulfonate, 4-fluorobenzenesulfonate, toluenesulfonate, benzenesulfonate, naphthalenesulfonate, camphorsulfonate, octanesulfonate, dodecylbenzenesulfonate, butanesulfonate, methanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropanesulfonate, 2-adamantanecarbonyloxy-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-naphthylethanesulfonate, 1,1,2,2-tetrafluoro-2-(norbornan-2-yl)ethanesulfonate, and 1,1,2,2-tetrafluoro-2-(tetracyclo [4.4.0.1$^{2,5}$.1$^{7,10}$]dodec-3-en-8-yl)ethanesulfonate.

Nitrobenzyl sulfonate photoacid generators include 2,4-dinitrobenzyl sulfonates, 2-nitrobenzyl sulfonates, and 2,6-dinitrobenzyl sulfonates, with exemplary sulfonates including trifluoromethanesulfonate, pentafluoroethanesulfonate, nonafluorobutanesulfonate, dodecafluorohexanesulfonate, pentafluoroethylperfluorocyclohexanesulfonate, heptadecafluorooctanesulfonate, 2,2,2-trifluoroethanesulfonate, pentafluorobenzenesulfonate, 4-trifluoromethylbenzenesulfonate, 4-fluorobenzenesulfonate, toluenesulfonate, benzenesulfonate, naphthalenesulfonate, camphorsulfonate, octanesulfonate, dodecylbenzenesulfonate, butanesulfonate, methanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropanesulfonate, 2-adamantanecarbonyloxy-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-naphthylethanesulfonate, 1,1,2,2-tetrafluoro-2-(norbornan-2-yl)ethanesulfonate, and 1,1,2,2-tetrafluoro-2-(tetracyclo [4.4.0.1$^{2,5}$.1$^{7,10}$]dodec-3-en-8-yl)ethanesulfonate. Also useful are analogous nitrobenzyl sulfonate compounds in which the nitro group on the benzyl side is substituted by a trifluoromethyl group.

Sulfone photoacid generators include bis(phenylsulfonyl)methane, bis(4-methylphenylsulfonyl)methane, bis(2-naphthylsulfonyl)methane, 2,2-bis(phenylsulfonyl)propane, 2,2-bis(4-methylphenylsulfonyl)propane, 2,2-bis(2-naphthylsulfonyl)propane, 2-methyl-2-(p-toluenesulfonyl)propiophenone, 2-cyclohexylcarbonyl-2-(p-toluenesulfonyl)propane, and 2,4-dimethyl-2-(p-toluenesulfonyl)pentan-3-one.

Photoacid generators in the form of glyoxime derivatives are described in Japanese Patent No. 2,906,999 and JP-A 9-301948 and include bis-O-(p-toluenesulfonyl)-α-dimethylglyoxime, bis-O-(p-toluenesulfonyl)-α-diphenylglyoxime, bis-O-(p-toluenesulfonyl)-α-dicyclohexylglyoxime, bis-O-(p-toluenesulfonyl)-2,3-pentanedioneglyoxime, bis-O-(n-butanesulfonyl)-α-dimethylglyoxime, bis-O-(n-butanesulfonyl)-α-diphenylglyoxime, bis-O-(n-butanesulfonyl)-α-dicyclohexylglyoxime, bis-O-(methanesulfonyl)-α-dimethylglyoxime, bis-O-(trifluoromethanesulfonyl)-α-dimethylglyoxime, bis-O-(2,2,2-trifluoroethanesulfonyl)-α-dimethylglyoxime, bis-O-(10-camphorsulfonyl)-α-dimethylglyoxime, bis-O-(benzenesulfonyl)-α-dimethylglyoxime, bis-O-(p-fluorobenzenesulfonyl)-α-dimethylglyoxime, bis-O-(p-trifluoromethylbenzenesulfonyl)-α-dimethylglyoxime, bis-O-(xylenesulfonyl)-α-dimethylglyoxime, bis-O-(trifluoromethanesulfonyl)-nioxime, bis-O-(2,2,2-trifluoroethanesulfonyl)-nioxime, bis-O-(10-camphorsulfonyl)-nioxime, bis-O-(benzenesulfonyl)-nioxime, bis-O-(p-fluorobenzenesulfonyl)-nioxime, bis-O-(p-trifluoromethylbenzenesulfonyl)-nioxime, and bis-O-(xylenesulfonyl)-nioxime.

Also included are the oxime sulfonates described in U.S. Pat. No. 6,004,724, for example, (5-(4-toluenesulfonyl)oxyimino-5H-thiophen-2-ylidene)phenylacetonitrile, (5-(10-camphorsulfonyl)oxyimino-5H-thiophen-2-ylidene)phenylacetonitrile, (5-n-octanesulfonyloxyimino-5H-thiophen-2-ylidene)phenylacetonitrile, (5-(4-toluenesulfonyl)oxyimino-5H-thiophen-2-ylidene)(2-methylphenyl)acetonitrile, (5-(10-camphorsulfonyl)oxyimino-5H-thiophen-2-ylidene)(2-methylphenyl)acetonitrile, (5-n-octanesulfonyloxyimino-5H-thiophen-2-ylidene)(2-methylphenyl)acetonitrile, etc.

Also included are the oxime sulfonates described in U.S. Pat. No. 6,916,591, for example, (5-(4-(4-toluenesulfonyloxy)benzenesulfonyl)oxyimino-5H-thiophen-2-ylidene)phenylacetonitrile and (5-(2,5-bis(4-toluenesulfonyloxy)benzenesulfonyl)oxyimino-5H-thiophen-2-ylidene) phenylacetonitrile.

Also included are the oxime sulfonates described in U.S. Pat. No. 6,261,738 and JP-A 2000-314956, for example, 2,2,2-trifluoro-1-phenyl-ethanone oxime-O-methylsulfonate; 2,2,2-trifluoro-1-phenyl-ethanone oxime-O-(10-camphorylsulfonate); 2,2,2-trifluoro-1-phenyl-ethanone oxime-O-(4-methoxyphenylsulfonate); 2,2,2-trifluoro-1-phenyl-ethanone oxime-O-(1-naphthylsulfonate); 2,2,2-trifluoro-1-phenyl-ethanone oxime-O-(2-naphthylsulfonate); 2,2,2-trifluoro-1-phenyl-ethanone oxime-O-(2,4,6-trimethylphenylsulfonate); 2,2,2-trifluoro-1-(4-methylphenyl)-ethanone oxime-O-(10-camphorylsulfonate); 2,2,2-trifluoro-1-(4-methylphenyl)ethanone oxime-O-(methylsulfonate); 2,2,2-trifluoro-1-(2-methylphenyl)-ethanone oxime-O-(10-camphorylsulfonate); 2,2,2-trifluoro-1-(2,4-dimethylphenyl)-ethanone oxime-O-(10-camphorylsulfonate); 2,2,2-trifluoro-1-(2,4-dimethylphenyl)ethanone oxime-O-(1-naphthylsulfonate); 2,2,2-trifluoro-1-(2,4-dimethylphenyl)-ethanone oxime-O-(2-naphthylsulfonate); 2,2,2-trifluoro-1-(2,4,6-trimethylphenyl)-ethanone oxime-O-(10-camphorylsulfonate); 2,2,2-trifluoro-1-(2,4,6-trimethylphenyl)-ethanone oxime-O-(1-naphthylsulfonate); 2,2,2-trifluoro-1-(2,4,6-trimethylphenyl)-ethanone oxime-O-(2-naphthylsulfonate); 2,2,2-trifluoro-1-(4-methoxyphenyl)ethanone oxime-O-methylsulfonate; 2,2,2-trifluoro-1-(4-methylthiophenyl)-ethanone oxime-O-methylsulfonate; 2,2,2-trifluoro-1-(3,4-dimethoxyphenyl)-ethanone oxime-O-methylsulfonate; 2,2,3,3,4,4,4-heptafluoro-1-phenyl-butanone oxime-O-(10-camphorylsulfonate); 2,2,2-trifluoro-1-(phenyl)ethanone oxime-O-methylsulfonate; 2,2,2-trifluoro-1-(phenyl)ethanone oxime-O-10-camphorylsulfonate; 2,2,2-trifluoro-1-(phenyl)-ethanone oxime-O-(4-methoxyphenyl)sulfonate; 2,2,2-trifluoro-1-(phenyl)-ethanone oxime-O-(1-naphthyl)sulfonate; 2,2,2-trifluoro-1-(phenyl)-ethanone oxime-O-(2-naphthyl)sulfonate; 2,2,2-trifluoro-1-(phenyl)-ethanone oxime-O-(2,4,6-trimethylphenyl)sulfonate; 2,2,2-trifluoro-1-(4-methylphenyl)-ethanone oxime-O-(10-camphoryl)sulfonate; 2,2,2-trifluoro-1-(4-methylphenyl)-ethanone oxime-O-methylsulfonate; 2,2,2-trifluoro-1-(2-methylphenyl)-ethanone oxime-O-(10-camphoryl)sulfonate; 2,2,2-trifluoro-1-(2,4-dimethylphenyl)-ethanone oxime-O-(1-naphthyl)sulfonate; 2,2,2-trifluoro-1-(2,4-dimethylphenyl)-ethanone oxime-O-(2-naphthyl)sulfonate; 2,2,2-trifluoro-1-(2,4,6-trimethylphenyl)-ethanone oxime-O-(10-camphoryl)sulfonate; 2,2,2-trifluoro-1-(2,4,6-trimethylphenyl)-ethanone oxime-O-(1-naphthyl)sulfonate; 2,2,2-trifluoro-1-(2,4,6-trimethylphenyl)-ethanone oxime-O-(2-naphthyl)sulfonate; 2,2,2-trifluoro-1-(4-methoxyphenyl)-ethanone oxime-O-methylsulfonate; 2,2,2-trifluoro-1-(4-thiomethylphenyl)ethanone oxime-O-methylsulfonate; 2,2,2-trifluoro-1-(3,4-dimethoxyphenyl)-ethanone oxime-O-methylsulfonate; 2,2,2-trifluoro-1-(4-methoxyphenyl)-ethanone oxime-O-(4-methylphenyl)sulfonate; 2,2,2-trifluoro-1-(4-methoxyphenyl)ethanone oxime-O-(4-methoxyphenyl)sulfonate; 2,2,2-trifluoro-1-(4-methoxyphenyl)-ethanone oxime-O-(4-dodecylphenyl)sulfonate; 2,2,2-trifluoro-1-(4-methoxyphenyl)-ethanone oxime-O-octylsulfonate; 2,2,2-trifluoro-1-(4-thiomethylphenyl)-ethanone oxime-O-(4-methoxyphenyl)sulfonate; 2,2,2-trifluoro-1-(4-thiomethylphenyl)-ethanone oxime-O-(4-dodecylphenyl) sulfonate; 2,2,2-trifluoro-1-(4-thiomethylphenyl)-ethanone oxime-O-octylsulfonate; 2,2,2-trifluoro-1-(4-thiomethylphenyl)-ethanone oxime-O-(2-naphthyl)sulfonate; 2,2,2-trifluoro-1-(2-methylphenyl)-ethanone oxime-O-methylsulfonate; 2,2,2-trifluoro-1-(4-methylphenyl)ethanone oxime-O-phenylsulfonate; 2,2,2-trifluoro-1-(4-chlorophenyl)-ethanone oxime-O-phenylsulfonate; 2,2,3,3,4,4,4-heptafluoro-1-(phenyl)-butanone oxime-O-(10-camphoryl)sulfonate; 2,2,2-trifluoro-1-naphthyl-ethanone oxime-O-methylsulfonate; 2,2,2-trifluoro-2-naphthyl-ethanone oxime-O-methylsulfonate; 2,2,2-trifluoro-1-[4-benzylphenyl]-ethanone oxime-O-methylsulfonate; 2,2,2-trifluoro-1-[4-(phenyl-1,4-dioxa-but-1-yl)phenyl]-ethanone oxime-O-methylsulfonate; 2,2,2-trifluoro-1-naphthyl-ethanone oxime-O-propylsulfonate; 2,2,2-trifluoro-2-naphthyl-ethanone oxime-O-propylsulfonate; 2,2,2-trifluoro-1-[4-benzylphenyl]-ethanone oxime-O-propylsulfonate; 2,2,2-trifluoro-1-[4-methylsulfonylphenyl]-ethanone oxime-O-propylsulfonate; 1,3-bis[1-(4-phenoxyphenyl)-2,2,2-trifluoroethanone oxime-O-sulfonyl]phenyl; 2,2,2-trifluoro-1-[4-methylsulfonyloxyphenyl]-ethanone oxime-O-propylsulfonate; 2,2,2-trifluoro-1-[4-methylcarbonyloxyphenyl]-ethanone oxime-O-propylsulfonate; 2,2,2-trifluoro-1-[6H,7H-5,8-dioxonaphth-2-yl]-ethanone oxime-O-propylsulfonate; 2,2,2-trifluoro-1-[4-methoxycarbonylmethoxyphenyl]-ethanone oxime-O-propylsulfonate; 2,2,2-trifluoro-1-[4-(methoxycarbonyl)-(4-amino-1-oxa-pent-1-yl)-phenyl]-ethanone oxime-O-propylsulfonate; 2,2,2-trifluoro-1-[3,5-dimethyl-4-ethoxyphenyl]-ethanone oxime-O-propylsulfonate; 2,2,2-trifluoro-1-[4-benzyloxyphenyl]-ethanone oxime-O-propylsulfonate; 2,2,2-trifluoro-1-[2-thiophenyl]-ethanone oxime-O-propylsulfonate; 2,2,2-trifluoro-1-[1-dioxathiophen-2-yl)]-ethanone oxime-O-propylsulfonate; 2,2,2-trifluoro-1-(4-(3-(4-(2,2,2-trifluoro-1-(trifluoromethanesulfonyloxyimino)-ethyl)-phenoxy)-propoxy)-phenyl)ethanone oxime(trifluoromethanesulfonate); 2,2,2-trifluoro-1-(4-(3-(4-(2,2,2-trifluoro-1-(1-propanesulfonyloxyimino)-ethyl)phenoxy)-propoxy)-phenyl)ethanone oxime(1-propanesulfonate); and 2,2,2-trifluoro-1-(4-(3-(4-(2,2,2-trifluoro-1-(1-butanesulfonyloxyimino)-ethyl)-phenoxy)-propoxy)phenyl)ethanone oxime(1-butanesulfonate). Also included are the oxime sulfonates described in U.S. Pat. No. 6,916,591, for example, 2,2,2-trifluoro-1-(4-(3-(4-(2,2,2-trifluoro-1-(4-(4-methylphenylsulfonyloxy)phenylsulfonyloxyimino)-ethyl)phenoxy)-propoxy)-phenyl)ethanone oxime(4-(4-methylphenylsulfonyloxy)phenylsulfonate) and 2,2,2-trifluoro-1-(4-(3-(4-(2,2,2-trifluoro-1-(2,5-bis(4-methylphenylsulfonyloxy)benzenesulfonyloxy)phenylsulfonyloxyimino)-ethyl)-phenoxy)-propoxy)phenyl)ethanone oxime(2,5-bis(4-methylphenylsulfonyloxy)benzenesulfonyloxy)phenylsulfonate).

Also included are the oxime sulfonates described in JP-A 9-95479 and JP-A 9-230588 and the references cited therein, for example, α-(p-toluenesulfonyloxyimino)-phenylacetonitrile, α-(p-chlorobenzenesulfonyloxyimino)-phenylacetonitrile, α-(4-nitrobenzenesulfonyloxyimino)-phenylacetonitrile, α-(4-nitro-2-trifluoromethylbenzenesulfonyloxyimino)-phenylacetonitrile, α-(benzenesulfonyloxyimino)-4-chlorophenylacetonitrile, α-(benzenesulfonyloxyimino)-2,4-dichlorophenylacetonitrile, α-(benzenesulfonyloxyimino)-2,6-dichlorophenylacetonitrile, α-(benzenesulfonyloxyimino)-4-methoxyphenylacetonitrile, α-(2-chlorobenzenesulfonyloxyimino)-4-methoxyphenylacetonitrile, α-(benzenesulfonyloxyimino)-2-thienylacetonitrile, α-(4-dodecylbenzenesulfonyloxyimino)- phenylacetonitrile, α-[(4-toluenesulfonyloxyimino)-4-methoxyphenyl]acetonitrile, α-[(dodecylbenzenesulfonyloxyimino)-4-methoxyphenyl]acetonitrile, α-(tosyloxyimino)-3-thienylacetonitrile, α-(methylsulfonyloxyimino)-1-cyclopentenylacetonitrile, α-(ethylsulfonyloxyimino)-1-cyclopentenylacetonitrile, α-(isopropylsulfonyloxyimino)-1-cyclopentenylacetonitrile, α-(n-butylsulfonyloxyimino)-1-cyclopentenylacetonitrile, α-(ethylsulfonyloxyimino)-1-cyclohexenylacetonitrile, α-(isopropylsulfonyloxyimino)-1-cyclohexenylacetonitrile, and α-(n-butylsulfonyloxyimino)-1-cyclohexenylacetonitrile.

Also included are oxime sulfonates having the formula:

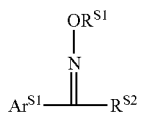

wherein $R^{s1}$ is a substituted or unsubstituted haloalkylsulfonyl or halobenzenesulfonyl group of 1 to 10 carbon atoms, $R^{s2}$ is a haloalkyl group of 1 to 11 carbon atoms, and $Ar^{s1}$ is substituted or unsubstituted aromatic or hetero-aromatic group, as described in WO 2004/074242. Examples include 2-[2,2,3,3,4,4,5,5-octafluoro-1-(nonafluorobutylsulfonyloxyimino)-pentyl]-fluorene, 2-[2,2,3,3,4,4-pentafluoro-1-(nonafluorobutylsulfonyloxyimino)-butyl]-fluorene, 2-[2,2,3,3,4,4,5,5,6,6-decafluoro-1-(nonafluorobutylsulfonyloxyimino)-hexyl]-fluorene, 2-[2,2,3,3,4,4,5,5-octafluoro-1-(nonafluorobutylsulfonyloxyimino)-pentyl]-4-biphenyl, 2-[2,2,3,3,4,4-pentafluoro-1-(nonafluorobutylsulfonyloxyimino)-butyl]-4-biphenyl, and 2-[2,2,3,3,4,4,5,5,6,6-decafluoro-1-(nonafluorobutylsulfonyloxyimino)-hexyl]-4-biphenyl.

Suitable bisoxime sulfonates include those described in JP-A 9-208554, for example, bis(α-(4-toluenesulfonyloxy)imino)-p-phenylenediacetonitrile, bis(α-(benzenesulfonyloxy)imino)-p-phenylenediacetonitrile, bis(α-(methanesulfonyloxy)imino)-p-phenylenediacetonitrile, bis(α-(butanesulfonyloxy)imino)-p-phenylenediacetonitrile, bis(α-(10-camphorsulfonyloxy)imino)-p-phenylenediacetonitrile, bis(α-(4-toluenesulfonyloxy)imino)-p-phenylenediacetonitrile, bis(α-(trifluoromethanesulfonyloxy)imino)-p-phenylenediacetonitrile, bis(α-(4-methoxybenzenesulfonyloxy)imino)-p-phenylenediacetonitrile, bis(α-(4-toluenesulfonyloxy)imino)-m-phenylenediacetonitrile, bis(α-(benzenesulfonyloxy)imino)-m-phenylenediacetonitrile, bis(α-(methanesulfonyloxy)imino)-m-phenylenediacetonitrile, bis(α-(butanesulfonyloxy)imino)-m-phenylenediacetonitrile, bis(α-(10-camphorsulfonyloxy)imino)-m-phenylenediacetonitrile, bis(α-(4-toluenesulfonyloxy)imino)-m-phenylenediacetonitrile, bis(α-(trifluoromethanesulfonyloxy)imino)-m-phenylenediacetonitrile, bis(α-(4-methoxybenzenesulfonyloxy)imino)-m-phenylenediacetonitrile, etc.

Of these, preferred photoacid generators are sulfonium salts, bissulfonyldiazomethanes, N-sulfonyloxyimides, oxime-O-sulfonates and glyoxime derivatives. More preferred photoacid generators are sulfonium salts, bissulfonyldiazomethanes, N-sulfonyloxyimides, and oxime-O-sulfonates. Typical examples include triphenylsulfonium p-toluenesulfonate, triphenylsulfonium camphorsulfonate, triphenylsulfonium pentafluorobenzenesulfonate, triphenylsulfonium nonafluorobutanesulfonate, triphenylsulfonium 4-(4'-toluenesulfonyloxy)benzenesulfonate, triphenylsulfonium 2,4,6-triisopropylbenzenesulfonate, 4-tert-butoxyphenyldiphenylsulfonium p-toluenesulfonate, 4-tert-butoxyphenyldiphenylsulfonium camphorsulfonate, 4-tert-butoxyphenyldiphenylsulfonium 4-(4'-toluenesulfonyloxy)benzenesulfonate, tris(4-methylphenyl)sulfonium camphorsulfonate, tris(4-tert-butylphenyl)sulfonium camphorsulfonate, 4-tert-butylphenyldiphenylsulfonium camphorsulfonate, 4-tert-butylphenyldiphenylsulfonium nonafluoro-1'-butanesulfonate, 4-tert-butylphenyldiphenylsulfonium pentafluoroethylperfluorocyclohexanesulfonate, 4-tert-butylphenyldiphenylsulfonium perfluoro-1-octanesulfonate, triphenylsulfonium 1,1-difluoro-2-naphthyl-ethanesulfonate, triphenylsulfonium 1,1,2,2-tetrafluoro-2-(norbornan-2-yl)ethanesulfonate, bis(tert-butylsulfonyl)diazomethane, bis(cyclohexylsulfonyl)diazomethane, bis(2,4-dimethylphenylsulfonyl)diazomethane, bis(4-(n-hexyloxy)phenylsulfonyl)diazomethane, bis(2-methyl-4-(n-hexyloxy)phenylsulfonyl)diazomethane, bis(2,5-dimethyl-4-(n-hexyloxy)phenylsulfonyl)diazomethane, bis(3,5-dimethyl-4-(n-hexyloxy)phenylsulfonyl)diazomethane, bis(2-methyl-5-isopropyl-4-(n-hexyloxy)phenylsulfonyl)diazomethane, bis(4-tert-butylphenylsulfonyl)diazomethane, N-camphorsulfonyloxy-5-norbornene-2,3-dicarboxylic acid imide, N-p-toluenesulfonyloxy-5-norbornene-2,3-dicarboxylic acid imide, 2-[2,2,3,3,4,4,5,5-octafluoro-1-(nonafluorobutylsulfonyloxyimino)-pentyl]-fluorene, 2-[2,2,3,3,4,4-pentafluoro-1-(nonafluorobutylsulfonyloxyimino)-butyl]-fluorene, and 2-[2,2,3,3,4,4,5,5,6,6-decafluoro-1-(nonafluorobutylsulfonyloxyimino)-hexyl]-fluorene.

In the resist composition, an appropriate amount of the photoacid generator is, but not limited to, 0.1 to 20 parts, and especially 0.1 to 10 parts by weight per 100 parts by weight of the base resin. Too high a proportion of the photoacid generator may give rise to problems of degraded resolution and foreign matter upon development and resist film peeling. The photoacid generators may be used alone or in admixture of two or more. The transmittance of the resist film can be controlled by using a photoacid generator having a low transmittance at the exposure wavelength and adjusting the amount of the photoacid generator added.

In the resist composition, there may be added a compound which is decomposed with an acid to generate an acid, that is, acid-amplifier compound. For these compounds, reference should be made to J. Photopolym. Sci. and Tech., 8, 43-44, 45-46 (1995), and ibid., 9, 29-30 (1996).

Examples of the acid-amplifier compound include tert-butyl-2-methyl-2-tosyloxymethyl acetoacetate and 2-phenyl-2-(2-tosyloxyethyl)-1,3-dioxolane, but are not limited thereto. Of well-known photoacid generators, many of those compounds having poor stability, especially poor thermal stability exhibit an acid amplifier-like behavior.

In the resist composition, an appropriate amount of the acid-amplifier compound is up to 2 parts, and especially up to 1 part by weight per 100 parts by weight of the base resin. Excessive amounts of the acid-amplifier compound make diffusion control difficult, leading to degradation of resolution and pattern profile.

Organic Solvent

The organic solvent (C) used herein may be any organic solvent in which the base resin, acid generator, and other components are soluble. Illustrative, non-limiting, examples of the organic solvent include ketones such as cyclohexanone and methyl n-amyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone. These solvents may be used alone or in combinations of two or more thereof. Of the above organic solvents, it is recommended to use diethylene glycol dimethyl ether, 1-ethoxy-2-propanol, propylene glycol monomethyl ether acetate, and mixtures thereof because the acid generator is most soluble therein.

An appropriate amount of the organic solvent used is about 200 to 1,000 parts, especially about 400 to 800 parts by weight per 100 parts by weight of the base resin in the resist composition.

Nitrogen-Containing Compound

In the resist composition, an organic nitrogen-containing compound or compounds (D) may be compounded. The organic nitrogen-containing compound used herein is preferably a compound capable of suppressing the rate of diffusion when the acid generated by the acid generator diffuses within the resist film. The inclusion of this type of organic nitrogen-containing compound holds down the rate of acid diffusion within the resist film, resulting in better resolution. In addition, it suppresses changes in sensitivity following exposure and reduces substrate and environment dependence, as well as improving the exposure latitude and the pattern profile.

Examples of organic nitrogen-containing compounds include primary, secondary, and tertiary aliphatic amines, mixed amines, aromatic amines, heterocyclic amines, nitrogen-containing compounds having carboxyl group, nitrogen-containing compounds having sulfonyl group, nitrogen-containing compounds having hydroxyl group, nitrogen-containing compounds having hydroxyphenyl group, alcoholic nitrogen-containing compounds, amide derivatives, imide derivatives, and carbamate derivatives.

Examples of suitable primary aliphatic amines include ammonia, methylamine, ethylamine, n-propylamine, isopropylamine, n-butylamine, isobutylamine, sec-butylamine, tert-butylamine, pentylamine, tert-amylamine, cyclopentylamine, hexylamine, cyclohexylamine, heptylamine, octylamine, nonylamine, decylamine, dodecylamine, cetylamine, methylenediamine, ethylenediamine, and tetraethylenepentamine. Examples of suitable secondary aliphatic amines include dimethylamine, diethylamine, di-n-propylamine, diisopropylamine, di-n-butylamine, diisobutylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N-dimethylmethylenediamine, N,N-dimethylethylenediamine, and N,N-dimethyltetraethylenepentamine. Examples of suitable tertiary aliphatic amines include trimethylamine, triethylamine, tri-n-propylamine, triisopropylamine, tri-n-butylamine, triisobutylamine, tri-sec-butylamine, tripentylamine, tricyclopentylamine, trihexylamine, tricyclohexylamine, triheptylamine, trioctylamine, trinonylamine, tridecylamine, tridodedylamine, tricetylamine, N,N,N',N'-tetramethylmethylenediamine, N,N,N',N'-tetramethylethylenediamine, and N,N,N',N'-tetramethyltetraethylenepentamine.

Examples of suitable mixed amines include dimethylethylamine, methylethylpropylamine, benzylamine, phenethylamine, and benzyldimethylamine. Examples of suitable aromatic and heterocyclic amines include aniline derivatives (e.g., aniline, N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine), diphenyl(p-tolyl)amine, methyldiphenylamine, triphenylamine, phenylenediamine, naphthylamine, diaminonaphthalene, pyrrole derivatives (e.g., pyrrole, 2H-pyrrole, 1-methylpyrrole, 2,4-dimethylpyrrole, 2,5-dimethylpyrrole, and N-methylpyrrole), oxazole derivatives (e.g., oxazole and isooxazole), thiazole derivatives (e.g., thiazole and isothiazole), imidazole derivatives (e.g., imidazole, 4-methylimidazole, and 4-methyl-2-phenylimidazole), pyrazole derivatives, furazan derivatives, pyrroline derivatives (e.g., pyrroline and 2-methyl-1-pyrroline), pyrrolidine derivatives (e.g., pyrrolidine, N-methylpyrrolidine, pyrrolidinone, and N-methylpyrrolidone), imidazoline derivatives, imidazolidine derivatives, pyridine derivatives (e.g., pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 4-pyrrolidinopyridine, 2-(1-ethylpropyl)pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (e.g., quinoline and 3-quinolinecarbonitrile), isoquinoline derivatives, cinnoline derivatives, quinazoline derivatives, quinoxaline derivatives, phthalazine derivatives, purine derivatives, pteridine derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivatives, and uridine derivatives.

Examples of suitable nitrogen-containing compounds having carboxyl group include aminobenzoic acid, indolecarboxylic acid, and amino acid derivatives (e.g. nicotinic acid, alanine, alginine, aspartic acid, glutamic acid, glycine, histidine, isoleucine, glycylleucine, leucine, methionine, phenylalanine, threonine, lysine, 3-aminopyrazine-2-carboxylic acid, and methoxyalanine). Examples of suitable nitrogen-containing compounds having sulfonyl group include 3-pyridinesulfonic acid and pyridinium p-toluenesulfonate. Examples of suitable nitrogen-containing compounds having hydroxyl group, nitrogen-containing compounds having hydroxyphenyl group, and alcoholic nitrogen-containing compounds include 2-hydroxypyridine, aminocresol, 2,4-quinolinediol, 3-indolemethanol hydrate, monoethanolamine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(2-hydroxyethyl)morpholine, 2-(2-hydroxyethyl)pyridine, 1-(2-hydroxyethyl)piperazine, 1-[2-(2-hydroxyethoxy)ethyl]piperazine, piperidine ethanol, 1-(2-hydroxyethyl)pyrrolidine, 1-(2-hydroxyethyl)-2-pyrrolidinone, 3-piperidino-1,2-propanediol, 3-pyrrolidino-1,2-propanediol, 8-hydroxyjulolidine, 3-quinuclidinol, 3-tropanol, 1-methyl-2-pyrrolidine ethanol, 1-aziridine ethanol, N-(2-hydroxyethyl)phthalimide, and N-(2-hydroxyethyl)isonicotinamide. Examples of suitable amide derivatives include formamide, N-methylformamide, N,N-dimethylformamide, acetamide, N-methylacetamide, N,N-dimethylacetamide, propionamide, benzamide, and 1-cyclohexylpyrrolidone. Suitable imide derivatives include phthalimide, succinimide, and maleimide. Suitable carbamate derivatives include N-t-butoxycarbonyl-N,N-dicyclohexylamine, N-t-butoxycarbonylbenzimidazole and oxazolidinone.

In addition, organic nitrogen-containing compounds of the following general formula (B)-1 may also be included alone or in admixture.

$$N(X)_n(Y)_{3-n} \tag{B-1}$$

In the formula, n is equal to 1, 2 or 3; side chain Y is independently hydrogen or a straight, branched or cyclic alkyl group of 1 to 20 carbon atoms which may contain an ether or hydroxyl group; and side chain X is independently selected from groups of the following general formulas (X)-1 to (X)-3, and two or three X's may bond together to form a ring.

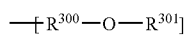   (X)-1

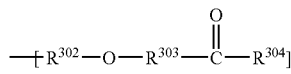   (X)-2

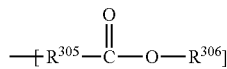   (X)-3

In the formulas, $R^{300}$, $R^{302}$ and $R^{305}$ are independently straight or branched alkylene groups of 1 to 4 carbon atoms; $R^{301}$ and $R^{304}$ are independently hydrogen, straight, branched or cyclic alkyl groups of 1 to 20 carbon atoms, which may contain at least one hydroxyl, ether, ester group or lactone ring; $R^{303}$ is a single bond or a straight or branched alkylene group of 1 to 4 carbon atoms; and $R^{306}$ is a straight, branched or cyclic alkyl group of 1 to 20 carbon atoms, which may contain at least one hydroxyl, ether, ester group or lactone ring.

Illustrative examples of the compounds of formula (B)-1 include tris(2-methoxymethoxyethyl)amine, tris{2-(2-methoxyethoxy)ethyl}amine, tris{2-(2-methoxyethoxymethoxy)ethyl}amine, tris{2-(1-methoxyethoxy)ethyl}amine, tris{2-(1-ethoxyethoxy)ethyl}amine, tris{2-(1-ethoxypropoxy)ethyl}amine, tris[2-{2-(2-hydroxyethoxy)ethoxy}ethyl]amine, 4,7,13,16,21,24-hexaoxa-1,10-diazabicyclo[8.8.8] hexacosane, 4,7,13,18-tetraoxa-1,10-diazabicyclo[8.5.5] eicosane, 1,4,10,13-tetraoxa-7,16-diazabicyclooctadecane, 1-aza-12-crown-4, 1-aza-15-crown-5, 1-aza-18-crown-6, tris (2-formyloxyethyl)amine, tris(2-acetoxyethyl)amine, tris(2-propionyloxyethyl)amine, tris(2-butyryloxyethyl)amine, tris (2-isobutyryloxyethyl)amine, tris(2-valeryloxyethyl)amine, tris(2-pivaloyloxyethyl)amine, N,N-bis(2-acetoxyethyl)-2-(acetoxyacetoxy)ethylamine, tris(2-methoxycarbonyloxyethyl)amine, tris(2-tert-butoxycarbonyloxyethyl)amine, tris [2-(2-oxopropoxy)ethyl]amine, tris[2-(methoxycarbonylmethyl)oxyethyl]amine, tris[2-(tert-butoxycarbonylmethyloxy)ethyl]amine, tris[2-(cyclohexyloxycarbonylmethyloxy)ethyl]amine, tris(2-methoxycarbonylethyl)amine, tris(2-ethoxycarbonylethyl) amine, N,N-bis(2-hydroxyethyl)-2-(methoxycarbonyl) ethylamine, N,N-bis(2-acetoxyethyl)-2-(methoxycarbonyl) ethylamine, N,N-bis(2-hydroxyethyl)-2-(ethoxycarbonyl) ethylamine, N,N-bis(2-acetoxyethyl)-2-(ethoxycarbonyl) ethylamine, N,N-bis(2-hydroxyethyl)-2-(2-methoxyethoxycarbonyl)ethylamine, N,N-bis(2-acetoxyethyl)-2-(2-methoxyethoxycarbonyl)ethylamine, N,N-bis(2-hydroxyethyl)-2-(2-hydroxyethoxycarbonyl) ethylamine, N,N-bis(2-acetoxyethyl)-2-(2-acetoxyethoxycarbonyl)ethylamine, N,N-bis(2-hydroxyethyl)-2-[(methoxycarbonyl)methoxycarbonyl]-ethylamine, N,N-bis(2-acetoxyethyl)-2-[(methoxycarbonyl)methoxycarbonyl]-ethylamine, N,N-bis(2-hydroxyethyl)-2-(2-oxopropoxycarbonyl)ethylamine, N,N-bis(2-acetoxyethyl)-2-(2-oxopropoxycarbonyl)ethylamine, N,N-bis(2-hydroxyethyl)-2-(tetrahydrofurfuryloxycarbonyl) ethylamine, N,N-bis(2-acetoxyethyl)-2-(tetrahydrofurfuryloxycarbonyl)ethylamine, N,N-bis(2-hydroxyethyl)-2-[(2-oxotetrahydrofuran-3-yl)oxycarbonyl] ethylamine, N,N-bis(2-acetoxyethyl)-2-[(2-oxotetrahydrofuran-3-yl)oxycarbonyl]ethylamine, N,N-bis (2-hydroxyethyl)-2-(4-hydroxybutoxycarbonyl)ethylamine, N,N-bis(2-formyloxyethyl)-2-(4-formyloxybutoxycarbonyl)ethylamine, N,N-bis(2-formyloxyethyl)-2-(2-formyloxyethoxycarbonyl)ethylamine, N,N-bis(2-methoxyethyl)-2-(methoxycarbonyl)ethylamine, N-(2-hydroxyethyl)-bis[2-(methoxycarbonyl)ethyl]amine, N-(2-acetoxyethyl)-bis[2-(methoxycarbonyl)ethyl]amine, N-(2-hydroxyethyl)-bis[2-(ethoxycarbonyl)ethyl]amine, N-(2-acetoxyethyl)-bis[2-(ethoxycarbonyl)ethyl]amine, N-(3-hydroxy-1-propyl)-bis [2-(methoxycarbonyl)ethyl]amine, N-(3-acetoxy-1-propyl)-bis[2-(methoxycarbonyl)ethyl]amine, N-(2-methoxyethyl)-bis[2-(methoxycarbonyl)ethyl]amine, N-butyl-bis[2-(methoxycarbonyl)ethyl]amine, N-butyl-bis[2-(2-methoxyethoxycarbonyl)ethyl]amine, N-methyl-bis(2-acetoxyethyl)amine, N-ethyl-bis(2-acetoxyethyl)amine, N-methyl-bis(2-pivaloyloxyethyl)amine, N-ethyl-bis[2-(methoxycarbonyloxy)ethyl]amine, N-ethyl-bis[2-(tert-butoxycarbonyloxy)ethyl]amine, tris(methoxycarbonylmethyl) amine, tris(ethoxycarbonylmethyl)amine, N-butyl-bis (methoxycarbonylmethyl)amine, N-hexyl-bis (methoxycarbonylmethyl)amine, and β-(diethylamino)-δ-valerolactone.

Also useful are one or more organic nitrogen-containing compounds having cyclic structure represented by the following general formula (B)-2.

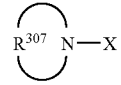   (B)-2

Herein X is as defined above, and $R^{307}$ is a straight or branched alkylene group of 2 to 20 carbon atoms which may contain one or more carbonyl, ether, ester or sulfide groups.

Illustrative examples of the organic nitrogen-containing compounds having formula (B)-2 include 1-[2-(methoxymethoxy)ethyl]pyrrolidine, 1-[2-(methoxymethoxy) ethyl]piperidine, 4-[2-(methoxymethoxy)ethyl]morpholine, 1-[2-[(2-methoxyethoxy)methoxy]ethyl]pyrrolidine, 1-[2-[(2-methoxyethoxy)methoxy]ethyl]piperidine, 4-[2-[(2-methoxyethoxy)methoxy]ethyl]morpholine, 2-(1-pyrrolidinyl)ethyl acetate, 2-piperidinoethyl acetate, 2-morpholinoethyl acetate, 2-(1-pyrrolidinyl)ethyl formate, 2-piperidinoethyl propionate, 2-morpholinoethyl acetoxyacetate, 2-(1-pyrrolidinyl)ethyl methoxyacetate, 4-[2-(methoxycarbonyloxy)ethyl]morpholine, 1-[2-(t-butoxycarbonyloxy)ethyl]piperidine, 4-[2-(2-methoxyethoxycarbonyloxy)

ethyl]morpholine, methyl 3-(1-pyrrolidinyl)propionate, methyl 3-piperidinopropionate, methyl 3-morpholinopropionate, methyl 3-(thiomorpholino)propionate, methyl 2-methyl-3-(1-pyrrolidinyl)propionate, ethyl 3-morpholinopropionate, methoxycarbonylmethyl 3-piperidinopropionate, 2-hydroxyethyl 3-(1-pyrrolidinyl)propionate, 2-acetoxyethyl 3-morpholinopropionate, 2-oxotetrahydrofuran-3-yl 3-(1-pyrrolidinyl)propionate, tetrahydrofurfuryl 3-morpholinopropionate, glycidyl 3-piperidinopropionate, 2-methoxyethyl 3-morpholinopropionate, 2-(2-methoxyethoxy)ethyl 3-(1-pyrrolidinyl)propionate, butyl 3-morpholinopropionate, cyclohexyl 3-piperidinopropionate, α-(1-pyrrolidinyl)methyl-γ-butyrolactone, β-piperidino-γ-butyrolactone, β-morpholino-δ-valerolactone, methyl 1-pyrrolidinylacetate, methyl piperidinoacetate, methyl morpholinoacetate, methyl thiomorpholinoacetate, ethyl 1-pyrrolidinylacetate, 2-methoxyethyl morpholinoacetate, 2-morpholinoethyl 2-methoxyacetate, 2-morpholinoethyl 2-(2-methoxyethoxy)acetate, 2-morpholinoethyl 2-[2-(2-methoxyethoxy)ethoxy]acetate, 2-morpholinoethyl hexanoate, 2-morpholinoethyl octanoate, 2-morpholinoethyl decanoate, 2-morpholinoethyl laurate, 2-morpholinoethyl myristate, 2-morpholinoethyl palmitate, and 2-morpholinoethyl stearate.

Also, one or more organic nitrogen-containing compounds having cyano group represented by the following general formulae (B)-3 to (B)-6 may be blended.

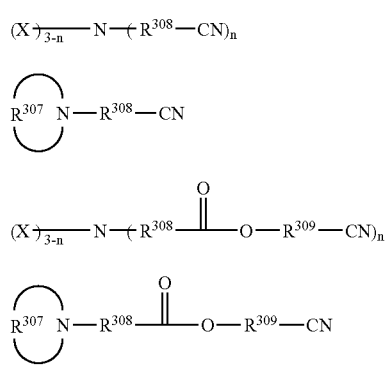

Herein, X, $R^{307}$ and n are as defined above, and $R^{308}$ and $R^{309}$ are each independently a straight or branched alkylene group of 1 to 4 carbon atoms.

Illustrative examples of the organic nitrogen-containing compounds having cyano represented by formulae (B)-3 to (B)-6 include 3-(diethylamino)propiononitrile, N,N-bis(2-hydroxyethyl)-3-aminopropiononitrile, N,N-bis(2-acetoxyethyl)-3-aminopropiononitrile, N,N-bis(2-formyloxyethyl)-3-aminopropiononitrile, N,N-bis(2-methoxyethyl)-3-aminopropiononitrile, N,N-bis[2-(methoxymethoxy)ethyl]-3-aminopropiononitrile, methyl N-(2-cyanoethyl)-N-(2-methoxyethyl)-3-aminopropionate, methyl N-(2-cyanoethyl)-N-(2-hydroxyethyl)-3-aminopropionate, methyl N-(2-acetoxyethyl)-N-(2-cyanoethyl)-3-aminopropionate, N-(2-cyanoethyl)-N-ethyl-3-aminopropiononitrile, N-(2-cyanoethyl)-N-(2-hydroxyethyl)-3-aminopropiononitrile, N-(2-acetoxyethyl)-N-(2-cyanoethyl)-3-aminopropiononitrile, N-(2-cyanoethyl)-N-(2-formyloxyethyl)-3-aminopropiononitrile, N-(2-cyanoethyl)-N-(2-methoxyethyl)-3-aminopropiononitrile, N-(2-cyanoethyl)-N-[2-(methoxymethoxy)ethyl]-3-aminopropiononitrile, N-(2-cyanoethyl)-N-(3-hydroxy-1-propyl)-3-aminopropiononitrile, N-(3-acetoxy-1-propyl)-N-(2-cyanoethyl)-3-aminopropiononitrile, N-(2-cyanoethyl)-N-(3-formyloxy-1-propyl)-3-aminopropiononitrile, N-(2-cyanoethyl)-N-tetrahydrofurfuryl-3-aminopropiononitrile, N,N-bis(2-cyanoethyl)-3-aminopropiononitrile, diethylaminoacetonitrile, N,N-bis(2-hydroxyethyl)aminoacetonitrile, N,N-bis(2-acetoxyethyl)aminoacetonitrile, N,N-bis(2-formyloxyethyl)aminoacetonitrile, N,N-bis(2-methoxyethyl)aminoacetonitrile, N,N-bis[2-(methoxymethoxy)ethyl]aminoacetonitrile, methyl N-cyanomethyl-N-(2-methoxyethyl)-3-aminopropionate, methyl N-cyanomethyl-N-(2-hydroxyethyl)-3-aminopropionate, methyl N-(2-acetoxyethyl)-N-cyanomethyl-3-aminopropionate, N-cyanomethyl-N-(2-hydroxyethyl)aminoacetonitrile, N-(2-acetoxyethyl)-N-(cyanomethyl)aminoacetonitrile, N-cyanomethyl-N-(2-formyloxyethyl)aminoacetonitrile, N-cyanomethyl-N-(2-methoxyethyl)aminoacetonitrile, N-cyanomethyl-N-[2-(methoxymethoxy)ethyl]aminoacetonitrile, N-cyanomethyl-N-(3-hydroxy-1-propyl)aminoacetonitrile, N-(3-acetoxy-1-propyl)-N-(cyanomethyl)aminoacetonitrile, N-cyanomethyl-N-(3-formyloxy-1-propyl)aminoacetonitrile, N,N-bis(cyanomethyl)aminoacetonitrile, 1-pyrrolidinepropiononitrile, 1-piperidinepropiononitrile, 4-morpholinepropiononitrile, 1-pyrrolidineacetonitrile, 1-piperidineacetonitrile, 4-morpholineacetonitrile, cyanomethyl 3-diethylaminopropionate, cyanomethyl N,N-bis(2-hydroxyethyl)-3-aminopropionate, cyanomethyl N,N-bis(2-acetoxyethyl)-3-aminopropionate, cyanomethyl N,N-bis(2-formyloxyethyl)-3-aminopropionate, cyanomethyl N,N-bis(2-methoxyethyl)-3-aminopropionate, cyanomethyl N,N-bis[2-(methoxymethoxy)ethyl]-3-aminopropionate, 2-cyanoethyl 3-diethylaminopropionate, 2-cyanoethyl N,N-bis(2-hydroxyethyl)-3-aminopropionate, 2-cyanoethyl N,N-bis(2-acetoxyethyl)-3-aminopropionate, 2-cyanoethyl N,N-bis(2-formyloxyethyl)-3-aminopropionate, 2-cyanoethyl N,N-bis(2-methoxyethyl)-3-aminopropionate, 2-cyanoethyl N,N-bis[2-(methoxymethoxy)ethyl]-3-aminopropionate, cyanomethyl 1-pyrrolidinepropionate, cyanomethyl 1-piperidinepropionate, cyanomethyl 4-morpholinepropionate, 2-cyanoethyl 1-pyrrolidinepropionate, 2-cyanoethyl 1-piperidinepropionate, and 2-cyanoethyl 4-morpholinepropionate.

Also included are organic nitrogen-containing compounds having an imidazole structure and a polar functional group, represented by the general formula (B)-7.

Herein, $R^{310}$ is a straight, branched or cyclic alkyl group of 2 to 20 carbon atoms bearing at least one polar functional group selected from among hydroxyl, carbonyl, ester, ether, sulfide, carbonate, cyano and acetal groups; $R^{311}$, $R^{312}$ and $R^{313}$ are each independently a hydrogen atom, a straight, branched or cyclic alkyl group, aryl group or aralkyl group having 1 to 10 carbon atoms.

Also included are organic nitrogen-containing compounds having a benzimidazole structure and a polar functional group, represented by the general formula (B)-8.

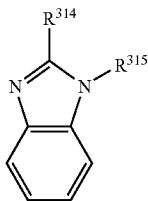

(B)-8

Herein, $R^{314}$ is a hydrogen atom, a straight, branched or cyclic alkyl group, aryl group or aralkyl group having 1 to 10 carbon atoms. $R^{315}$ is a polar functional group-bearing, straight, branched or cyclic alkyl group of 1 to 20 carbon atoms, and the alkyl group contains as the polar functional group at least one group selected from among ester, acetal and cyano groups, and may additionally contain at least one group selected from among hydroxyl, carbonyl, ether, sulfide and carbonate groups.

Further included are heterocyclic nitrogen-containing compounds having a polar functional group, represented by the general formulae (B)-9 and (B)-10.

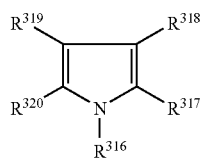

(B)-9

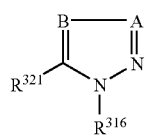

(B)-10

Herein, A is a nitrogen atom or =C—$R^{322}$, B is a nitrogen atom or =C—$R^{323}$, $R^{316}$ is a straight, branched or cyclic alkyl group of 2 to 20 carbon atoms bearing at least one polar functional group selected from among hydroxyl, carbonyl, ester, ether, sulfide, carbonate, cyano and acetal groups; $R^{317}$, $R^{318}$, $R^{319}$ and $R^{320}$ are each independently a hydrogen atom, a straight, branched or cyclic alkyl group or aryl group having 1 to 10 carbon atoms, or a pair of $R^{317}$ and $R^{318}$ and a pair of $R^{319}$ and $R^{320}$, taken together, may form a benzene, naphthalene or pyridine ring; $R^{321}$ is a hydrogen atom, a straight, branched or cyclic alkyl group or aryl group having 1 to 10 carbon atoms; $R^{322}$ and $R^{323}$ each are a hydrogen atom, a straight, branched or cyclic alkyl group or aryl group having 1 to 10 carbon atoms, or a pair of $R^{321}$ and $R^{323}$, taken together, may form a benzene or naphthalene ring.

Also included are organic nitrogen-containing compounds of aromatic carboxylic ester structure having the general formulae (B)-11 to (B)-14.

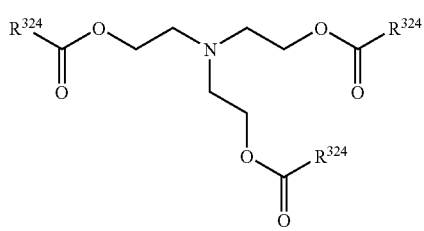

(B)-11

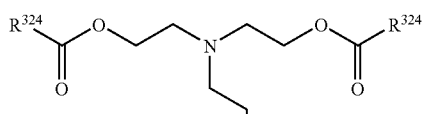

(B)-12

(B)-13

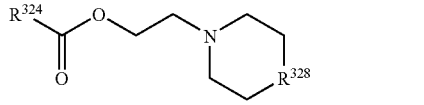

(B)-14

Herein $R^{324}$ is a $C_6$-$C_{20}$ aryl group or $C_4$-$C_{20}$ hetero-aromatic group, in which some or all of hydrogen atoms may be replaced by halogen atoms, straight, branched or cyclic $C_1$-$C_{20}$ alkyl groups, $C_6$-$C_{20}$ aryl groups, $C_1$-$C_{20}$ aralkyl groups, $C_1$-$C_{10}$ alkoxy groups, $C_1$-$C_{10}$ acyloxy groups or $C_1$-$C_{10}$ alkylthio groups. $R^{325}$ is $CO_2R^{326}$, $OR^{327}$ or cyano group. $R^{326}$ is a $C_1$-$C_{10}$ alkyl group, in which some methylene groups may be replaced by oxygen atoms. $R^{327}$ is a $C_1$-$C_{10}$ alkyl or acyl group, in which some methylene groups may be replaced by oxygen atoms. $R^{328}$ is a single bond, methylene, ethylene, sulfur atom or —$O(CH_2CH_2O)_n$— group wherein n is 0, 1, 2, 3 or 4. $R^{329}$ is hydrogen, methyl, ethyl or phenyl. X is a nitrogen atom or $CR^{330}$. Y is a nitrogen atom or $CR^{331}$. Z is a nitrogen atom or $CR^{332}$. $R^{330}$, $R^{331}$ and $R^{332}$ are each independently hydrogen, methyl or phenyl. Alternatively, a pair of $R^{330}$ and $R^{331}$ or a pair of $R^{331}$ and $R^{332}$ may bond together to form a $C_6$-$C_{20}$ aromatic ring or $C_2$-$C_{20}$ hetero-aromatic ring.

Further included are organic nitrogen-containing compounds of 7-oxanorbornane-2-carboxylic ester structure having the general formula (B)-15.

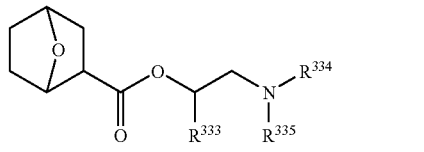

(B)-15

Herein $R^{333}$ is hydrogen or a straight, branched or cyclic $C_1$-$C_{10}$ alkyl group. $R^{334}$ and $R^{335}$ are each independently a $C_1$-$C_{20}$ alkyl group, $C_6$-$C_{20}$ aryl group or $C_1$-$C_{20}$ aralkyl group, which may contain one or more polar functional groups selected from among ether, carbonyl, ester, alcohol, sulfide, nitrile, amine, imine, and amide and in which some hydrogen atoms may be replaced by halogen atoms. $R^{334}$ and $R^{335}$, taken together, may form a heterocyclic or hetero-aromatic ring of 2 to 20 carbon atoms.

The organic nitrogen-containing compounds may be used alone or in admixture of two or more. The organic nitrogen-containing compound is preferably formulated in an amount of 0.001 to 2 parts, and especially 0.01 to 1 part by weight, per 100 parts by weight of the entire base resin. Less than 0.001 part of the nitrogen-containing compound achieves no or little addition effect whereas more than 2 parts would result in too low a sensitivity.

The resist composition of the invention may include optional ingredients, for example, a surfactant which is commonly used for improving the coating characteristics. Optional ingredients may be added in conventional amounts so long as this does not compromise the objects of the invention.

Nonionic surfactants are preferred, examples of which include perfluoroalkylpolyoxyethylene ethanols, fluorinated alkyl esters, perfluoroalkylamine oxides, perfluoroalkyl EO-addition products, and fluorinated organosiloxane compounds. Useful surfactants are commercially available under the trade names Fluorad FC-430 and FC-431 from Sumitomo 3M, Ltd., Surflon S-141, S-145, KH-10, KH-20, KH-30 and KH-40 from Asahi Glass Co., Ltd., Unidyne DS-401, DS-403 and DS-451 from Daikin Industry Co., Ltd., Megaface F-8151 from Dai-Nippon Ink & Chemicals, Inc., and X-70-092 and X-70-093 from Shin-Etsu Chemical Co., Ltd. Preferred surfactants are Fluorad FC-430 from Sumitomo 3M, Ltd., KH-20 and KH-30 from Asahi Glass Co., Ltd., and X-70-093 from Shin-Etsu Chemical Co., Ltd.

While the resist composition of the invention typically comprises a polymer, acid generator, organic solvent and organic nitrogen-containing compound as described above, there may be added optional other ingredients such as dissolution inhibitors, acidic compounds, stabilizers, and dyes. Optional ingredients may be added in conventional amounts so long as this does not compromise the objects of the invention.

Pattern formation using the resist composition of the invention may be carried out by a known lithographic technique. For example, the resist composition is applied onto a substrate such as a silicon wafer by spin coating or the like to form a resist film having a thickness of 0.05 to 2.0 μm, which is then pre-baked on a hot plate at 60 to 150° C. for 1 to 10 minutes, and preferably at 80 to 140° C. for 1 to 5 minutes. A patterning mask having the desired pattern is then placed over the resist film, and the film exposed through the mask to an electron beam or to high-energy radiation such as deep-UV rays, an excimer laser, or x-rays in a dose of about 1 to 200 mJ/cm², and preferably about 10 to 100 mJ/cm². Light exposure may be done by a conventional exposure process or in some cases, by an immersion process of providing liquid (typically water) impregnation between the mask and the resist. The resist film is then post-exposure baked (PEB) on a hot plate at 60 to 150° C. for 1 to 5 minutes, and preferably at 80 to 140° C. for 1 to 3 minutes. Finally, development is carried out using as the developer an aqueous alkali solution, such as a 0.1 to 5 wt % (preferably 2 to 3 wt %) aqueous solution of tetramethylammonium hydroxide (TMAH), this being done by a conventional method such as dip, puddle, or spray development for a period of 0.1 to 3 minutes, and preferably 0.5 to 2 minutes. These steps result in the formation of the desired pattern on the substrate. Of the various types of high-energy radiation that may be used, the resist composition of the invention is best suited to fine pattern formation with, in particular, deep-UV rays having a wavelength of 250 to 190 nm, an excimer laser, x-rays, or an electron beam. The desired pattern may not be obtainable outside the upper and lower limits of the above range.

EXAMPLE

Synthesis Examples and Examples are given below by way of illustration and not by way of limitation. The abbreviation Mw is a weight average molecular weight as measured by GPC using polystyrene standards. PGMEA is propylene glycol monomethyl ether acetate. Me stands for methyl.

Synthesis Example 1

Fluorinated monomers within the scope of the invention were synthesized according to the following formulation.

Synthesis Example 1-1

Synthesis of Monomer 1

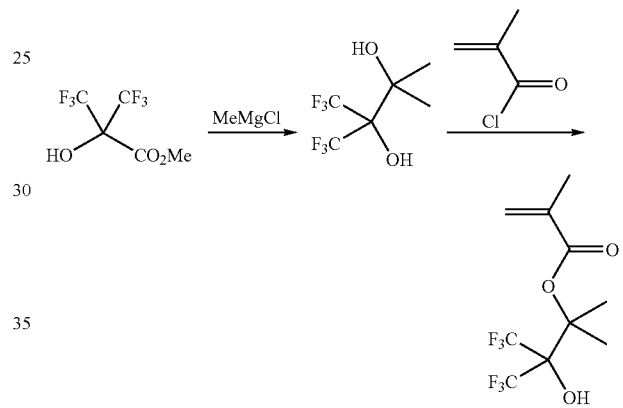

Synthesis Example 1-1-1

Synthesis of 1,1,1-trifluoro-2-trifluoromethyl-3-methyl-2,3-butane diol

A flask was charged with 1,260 ml of a tetrahydrofuran solution of 1M methylmagnesium chloride, to which 73.0 g of methyl 2-hydroxy-3,3,3-trifluoro-2-trifluoromethylpropionate was added dropwise below 50° C. The contents were stirred at room temperature for one hour, after which an ammonium chloride aqueous solution was added. This was followed by ordinary work-up and recrystallization from n-heptane, obtaining 59.1 g of the target compound (yield 81%).

melting point: 48° C. (start at 36° C., ramp 1° C./min)
$^1$H-NMR (600 MHz in DMSO-$d_6$): δ=1.31 (6H, s), 5.25 (1H, s), 7.43 (1H, s) ppm Synthesis Example 1-1-2

Synthesis of 3-hydroxy-2-methyl-4,4,4-trifluoro-3-trifluoromethylbutan-2-yl methacrylate In 300 ml of toluene were dissolved 55.0 g of the alcohol obtained in [1-1-1] and 32.0 g of triethylamine. 26.7 g of methacrylic chloride was added to the solution at 10° C., which was stirred at the temperature for 3 hours. 100 ml of water was added below 30° C. This was followed by ordinary work-up and vacuum distillation, obtaining 57.2 g of the target compound (yield 80%).

boiling point: 54-55° C./500 Pa

IR (thin film): ν=3255, 3039, 3014, 2966, 2935, 1697, 1635, 1475, 1456, 1338, 1315, 1257, 1238, 1226, 1193, 1170, 1153, 1137, 987, 946, 904 cm$^{-1}$ $^1$H-NMR (600 MHz in DMSO-d$_6$): δ=1.72 (6H, s), 1.81 (3H, s), 5.67 (1H, t-like), 5.97 (1H, t-like), 8.41 (1H, s) ppm $^{19}$F-NMR (565 MHz in DMSO-d$_6$, trifluoroacetic acid standard): δ=−70.1 (6F, s) ppm Synthesis Example 1-2

Synthesis of Monomer 2

The procedure of Synthesis Example 1-1-2 was repeated aside from using acrylic chloride instead of methacrylic chloride. There was obtained 3-hydroxy-2-methyl-4,4,4-trifluoro-3-trifluoromethylbutan-2-yl acrylate (yield 74%).

boiling point: 48-50° C./500 Pa

IR (thin film): ν=3259, 3039, 3014, 2967, 1704, 1637, 1619, 1475, 1448, 1407, 1307, 1226, 1193, 1155, 1137, 1049, 1022, 987, 956, 925 cm$^{-1}$ $^1$H-NMR (600 MHz in DMSO-d$_6$): δ=1.72 (6H, s), 5.94 (1H, dd), 6.03 (1H, dd), 6.26 (1H, dd), 8.39 (1H, s) ppm $^{19}$F-NMR (565 MHz in DMSO-d$_6$, trifluoroacetic acid standard): δ=−70.2 (6F, s) ppm Synthesis Example 1-3

Synthesis of Monomer 3

The procedure of Synthesis Example 1-1-2 was repeated aside from using α-trifluoromethylacrylic chloride instead of methacrylic chloride. There was obtained 3-hydroxy-2-methyl-4,4,4-trifluoro-3-trifluoromethylbutan-2-yl α-trifluoromethylacrylate (yield 70%).

Synthesis Example 1-4

Synthesis of Monomer 4

The procedure of Synthesis Example 1-1-2 was repeated aside from using α-fluoroacrylic chloride instead of methacrylic chloride. There was obtained 3-hydroxy-2-methyl-4,4,4-trifluoro-3-trifluoromethylbutan-2-yl α-fluoroacrylate (yield 60%).

Synthesis Example 1-5

Synthesis of Monomer 5

The procedure of Synthesis Example 1-1-2 was repeated aside from using 5-norbornene-2-carboxylic chloride instead of methacrylic chloride. There was obtained 3-hydroxy-2-methyl-4,4,4-trifluoro-3-trifluoromethylbutan-2-yl 5-norbornene-2-carboxylate (yield 80%).

boiling point: 65° C./16 Pa

IR (NaCl): ν=3241, 2979, 1706, 1257, 1236, 1193, 1172, 1153, 1137, 987, 723 cm$^{-1}$ $^1$H-NMR of main isomer (600 MHz in DMSO-d$_6$): δ=1.23-1.29 (3H, m), 1.62 (3H, s), 1.63 (3H, s), 1.76 (1H, dt), 2.84 (1H, br), 2.94 (1H, q), 3.08 (1H, br), 5.84 (1H, dd), 6.17 (1H, dd), 8.31 (1H, s) ppm $^{19}$F-NMR of main isomer (565 MHz in DMSO-d$_6$, trifluoroacetic acid standard): δ=−70.1 (3F, t), −70.0 (3F, t) ppm Synthesis Example 1-6

Synthesis of Monomer 6

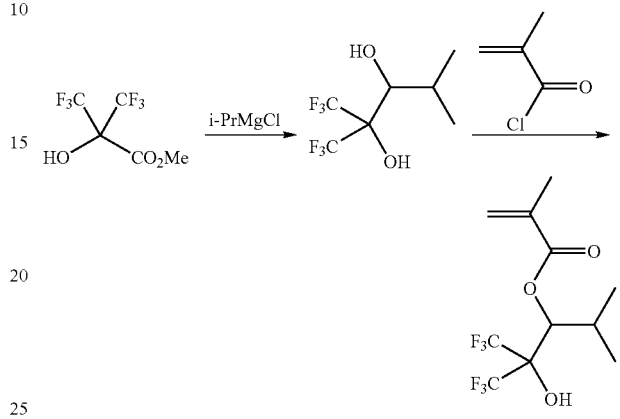

Synthesis Example 1-6-1

Synthesis of 4-methyl-1,1,1-trifluoro-2-trifluoromethyl-2,3-pentane diol

A flask was charged with 9.5 g of magnesium and 300 ml of tetrahydrofuran, to which 35.0 g of isopropyl chloride was added dropwise at 50° C. After the completion of dropwise addition, the contents were stirred for one hour at 60° C., and 22.6 g of methyl 2-hydroxy-3,3,3-trifluoro-2-trifluoromethylpropionate was added dropwise below 50° C. The mixture was stirred for one hour at room temperature, after which an ammonium chloride aqueous solution was added. This was followed by ordinary work-up and vacuum distillation, obtaining 20.2 g of the target compound (yield 84%).

boiling point: 96-98° C./13 kPa

Synthesis Example 1-6-2

Synthesis of 2-hydroxy-4-methyl-1,1,1-trifluoro-2-trifluoromethylpentan-3-yl methacrylate In 60 ml of toluene were dissolved 18.9 g of the alcohol obtained in [1-6-1] and 10.4 g of triethylamine. 9.1 g of methacrylic chloride was added to the solution at 10° C., which was stirred at the temperature for 3 hours. 40 ml of water was added below 30° C. This was followed by ordinary work-up and vacuum distillation, obtaining 19.9 g of the target compound (yield 82%).

boiling point: 72-75° C./270 Pa

IR (thin film): ν=3413, 2977, 2939, 2885, 1716, 1639, 1469, 1456, 1398, 1382, 1324, 1214, 1166, 1076, 1016, 950, 925 cm$^{-1}$ $^1$H-NMR (600 MHz in DMSO-d$_6$): δ=0.82 (3H, d), 1.03 (3H, d), 1.88 (3H, t-like), 2.28 (1H, sept), 5.16-5.18 (1H, m), 5.77 (1H, t-like), 6.09 (1H, t-like), 8.46 (1H, s) ppm $^{19}$F-NMR (565 MHz in DMSO-d$_6$, trifluoroacetic acid standard): δ=−75.3 (3F, m), −72.3 (3F, m) ppm

Synthesis Example 1-7

Synthesis of Monomer 7

The procedure of Synthesis Example 1-6-2 was repeated aside from using acrylic chloride instead of methacrylic chloride. There was obtained 2-hydroxy-4-methyl-1,1,1-trifluoro-2-trifluoromethylpentan-3-yl acrylate (yield 81%).

Synthesis Example 1-8

Synthesis of Monomer 8

The procedure of Synthesis Example 1-6-2 was repeated aside from using 5-norbornene-2-carboxylic chloride instead of methacrylic chloride. There was obtained 2-hydroxy-4-methyl-1,1,1-trifluoro-2-trifluoromethylpentan-3-yl 5-norbornene-2-carboxylate (yield 84%).

Synthesis Example 1-9

Synthesis of Monomer 9

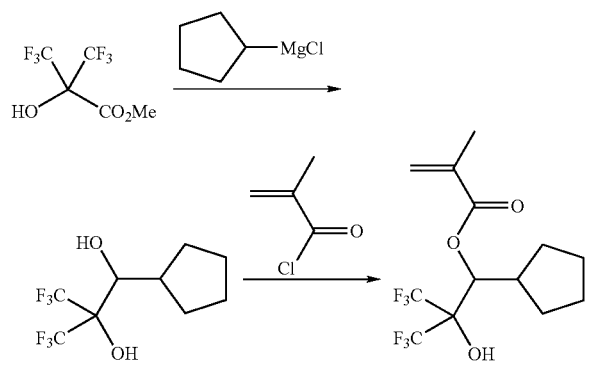

Synthesis Example 1-9-1

Synthesis of 3-cyclopentyl-3,3,3-trifluoro-2-trifluoromethyl-1,2-propane diol A flask was charged with 16.8 g of magnesium and 300 ml of tetrahydrofuran, to which 75.8 g of cyclopentyl chloride was added dropwise at 60° C. After the completion of dropwise addition, the contents were stirred for one hour at 60° C., and 40.0 g of methyl 2-hydroxy-3,3,3-trifluoro-2-trifluoromethylpropionate was added dropwise below 50° C. The mixture was stirred for one hour at room temperature, after which an ammonium chloride aqueous solution was added. This was followed by ordinary work-up and vacuum distillation, obtaining 39.1 g of the target compound (yield 83%).

boiling point: 88-90° C./1.3 kPa $^1$H-NMR (600 MHz in DMSO-d$_6$): δ=1.32-1.62 (6H, m), 1.65-1.77 (2H, m), 2.07-2.15 (1H, m), 3.72 (1H, dt), 5.53 (1H, d), 5.77 (1H, t-like), 7.50 (1H, s) ppm

Synthesis Example 1-9-2

Synthesis of 1-cyclopentyl-2-hydroxy-3,3,3-trifluoro-2-trifluoromethylpropyl methacrylate In 120 ml of toluene were dissolved 29.0 g of the alcohol obtained in [1-9-1] and 13.2 g of triethylamine. 11.0 g of methacrylic chloride was added to the solution at 10° C., which was stirred at the temperature for 3 hours. 40 ml of water was added to the reaction solution below 30° C., followed by ordinary work-up. Recrystallization from n-heptane gave 28.4 g of the target compound (yield 85%).

melting point: 59.0° C. (start at 50° C., ramp 1° C./min)

IR (thin film): ν=3382, 2983, 2958, 2877, 1706, 1637, 1627, 1457, 1440, 1409, 1384, 1353, 1330, 1272, 1240, 1218, 1168, 1151, 1137, 1066, 1014, 954, 931 cm$^{-1}$ $^1$H-NMR (600 MHz in DMSO-d$_6$): δ=1.23-1.63 (7H, m), 1.82-1.89 (4H, m), 2.27-2.37 (1H, m), 2.28 (1H, sept), 5.34 (1H, dd), 5.76 (1H, t-like), 6.07 (1H, t-like), 8.41 (1H, s) ppm $^{19}$F-NMR (565 MHz in DMSO-d$_6$, trifluoroacetic acid standard): δ=−75.0 (3F, m), −72.1 (3F, m) ppm

Synthesis Example 1-10

Synthesis of Monomer 10

The procedure of Synthesis Examples 1-9-1 to 1-9-2 was repeated aside from using cyclohexyl chloride instead of cyclopentyl chloride. There was obtained 1-cyclohexyl-2-hydroxy-3,3,3-trifluoro-2-trifluoromethylpropyl methacrylate (two-step yield 64%).

IR (thin film): ν=3388, 2985, 2954, 2939, 2865, 1708, 1637, 1457, 1438, 1405, 1384, 1348, 1332, 1321, 1301, 1274, 1251, 1230, 1214, 1189, 1168, 1151, 1132, 1105, 1066, 1014, 968, 954, 937 cm$^{-1}$ $^1$H-NMR (600 MHz in DMSO-d$_6$): δ=0.78-0.88 (1H, m), 1.00-1.24 (4H, m), 1.56 (1H, d), 1.66 (3H, m), 1.86-1.92 (4H, m), 1.97 (1H, m), 5.14 (1H, dd), 5.76 (1H, t-like), 6.08 (1H, t-like), 8.46 (1H, s) ppm $^{19}$F-NMR (565 MHz in DMSO-d$_6$, trifluoroacetic acid standard): δ=−75.3 (3F, m), −72.2 (3F, m) ppm

Synthesis Example 1-11

Synthesis of Monomer 11

The procedure of Synthesis Examples 1-9-1 to 1-9-2 was repeated aside from using bromoethane instead of cyclopentyl chloride. There was obtained 2-hydroxy-1,1,1-trifluoro-2-trifluoromethylpentan-3-yl methacrylate (two-step yield 61%).

Synthesis Example 1-12

Synthesis of Monomer 12

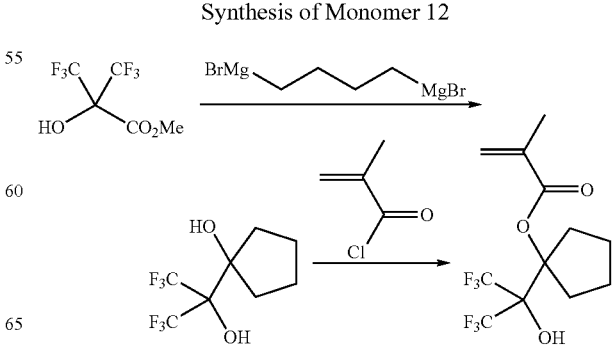

Synthesis Example 1-12-1

Synthesis of 1-[1-hydroxy-2,2,2-trifluoro-1-(trifluoromethyl)ethyl]cyclopentanol A flask was charged with 9.7 g of magnesium and 200 ml of tetrahydrofuran, to which 43.2 g of 1,4-dibromobutane was added dropwise at 60° C. After the completion of dropwise addition, the contents were stirred for one hour at 60° C., and 22.6 g of methyl 2-hydroxy-3,3,3-trifluoro-2-trifluoromethylpropionate was added dropwise below 50° C. The mixture was stirred for one hour at room temperature, after which an ammonium chloride aqueous solution was added. This was followed by ordinary work-up and vacuum distillation, obtaining 22.4 g of the target compound (yield 89%).

boiling point: 111-113° C./8.4 kPa $^1$H-NMR (600 MHz in DMSO-$d_6$): δ=1.50-1.58 (2H, m), 1.61-1.72 (4H, m), 1.92-2.02 (2H, m), 5.00 (1H, s), 7.55 (1H, s) ppm $^{19}$F-NMR (565 MHz in DMSO-$d_6$, trifluoroacetic acid standard): δ=−70.7 (6F, m) ppm

Synthesis Example 1-12-2

Synthesis of 1-[1-hydroxy-2,2,2-trifluoro-1-(trifluoromethyl)ethyl]cyclopentyl methacrylate In 100 ml of toluene were dissolved 19.2 g of the alcohol obtained in [1-12-1] and 12.3 g of triethylamine. 11.1 g of methacrylic chloride was added to the solution at 10° C., which was stirred at the temperature for 3 hours. 40 ml of water was added to the reaction solution below 30° C., followed by ordinary work-up. Vacuum distillation gave 19.5 g of the target compound (yield 80%).

boiling point: 49-50° C./23 Pa

IR (thin film): ν=3236, 2967, 2885, 1695, 1635, 1456, 1405, 1382, 1344, 1313, 1213, 1170, 1151, 1066, 1025, 1012, 931 cm$^{-1}$ $^1$H-NMR (600 MHz in DMSO-$d_6$): δ=1.58-1.65 (2H, m), 1.81 (3H, t), 1.88-1.95 (2H, m), 2.14-2.22 (2H, m), 2.26-2.34 (2H, m), 5.66 (1H, t-like), 5.96 (1H, t-like), 8.45 (1H, s) ppm $^{19}$F-NMR (565 MHz in DMSO-$d_6$, trifluoroacetic acid standard): δ=−70.3 (6F, s) ppm

Synthesis Example 1-13

Synthesis of Monomer 13

The procedure of Synthesis Example 1-12-2 was repeated aside from using acrylic chloride instead of methacrylic chloride. There was obtained 1-[1-hydroxy-2,2,2-trifluoro-1-(trifluoromethyl)ethyl]cyclopentyl acrylate (yield 78%).

Synthesis Example 1-14

Synthesis of Monomer 14

The procedure of Synthesis Examples 1-12-1 to 1-12-2 was repeated aside from using 1,5-dibromopentane instead of 1,4-dibromobutane. There was obtained 1-[1-hydroxy-2,2,2-trifluoro-1-(trifluoromethyl)ethyl]cyclohexyl methacrylate (two-step yield 62%).

Synthesis Example 1-15

Synthesis of Monomer 15

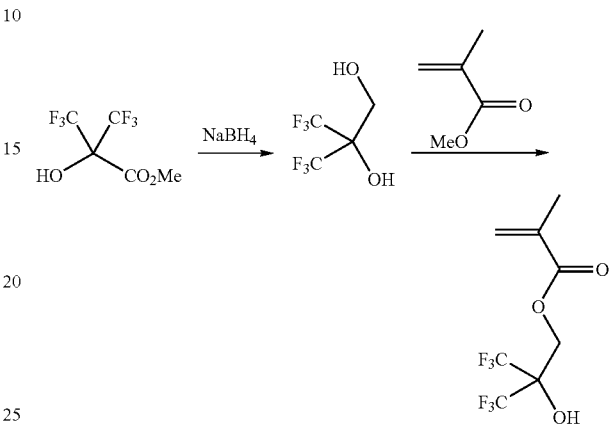

Synthesis Example 1-15-1

Synthesis of 3,3,3-trifluoro-2-trifluoromethyl-1,2-propane diol

To a mixture of 25.0 g of sodium boron hydride, 500 g of water, and 500 g of diethyl ether, with stirring, 100 g of methyl 2-hydroxy-3,3,3-trifluoro-2-trifluoromethylpropionate was added dropwise. The mixture was stirred for 10 hours, after which hydrochloric acid was added to quench the reaction. An organic layer was separated from the reaction mixture, concentrated, and distilled, obtaining 83.9 g of 3,3,3-trifluoro-2-trifluoromethyl-1,2-propane diol (yield 96%).

boiling point: 138° C.

melting point: 47° C.

Synthesis Example 1-15-2

Synthesis of 2-hydroxy-3,3,3-trifluoro-2-(trifluoromethyl)-propyl methacrylate A mixture of 50.0 g of the alcohol obtained in [1-15-1], 76.0 g of methyl methacrylate, 15 ml of toluene, and 300 mg of sodium methoxide was heated under reflux for 5 hours while distilling off the methanol resulting from reaction. The reaction solution was cooled, followed by ordinary aqueous work-up and vacuum concentration, obtaining a crude product. It was purified by vacuum distillation, obtaining 51.4 g of 2-hydroxy-3,3,3-trifluoro-2-(trifluoromethyl)-propyl methacrylate (yield 77%).

boiling point: 75° C./1,330 Pa

IR (thin film): ν=3411, 2973, 2937, 1714, 1639, 1457, 1407, 1382, 1328, 1268, 1220, 1157, 1089, 1041, 977, 952, 873, 813 cm$^{-1}$ $^1$H-NMR (600 MHz in DMSO-$d_6$): δ=1.87 (3H), 4.53 (2H), 5.77 (1H), 6.07 (1H), 8.47 (1H) ppm $^{19}$F-NMR (565 MHz in DMSO-$d_6$, trifluoroacetic acid standard): δ=−76.36 (3F), −76.35 (3F) ppm

Synthesis Example 1-16

Synthesis of Monomer 16

The procedure of Synthesis Example 1-15-2 was repeated aside from using methyl acrylate instead of methyl methacrylate. There was obtained 2-hydroxy-3,3,3-trifluoro-2-(trifluoromethyl)-propyl acrylate (yield 76%).

Synthesis Example 1-17

Synthesis of Monomer 17

The procedure of Synthesis Example 1-15-2 was repeated aside from using methyl 5-norbornene-2-carboxylate instead of methyl methacrylate. There was obtained 2-hydroxy-3,3,3-trifluoro-2-(trifluoromethyl)-propyl 5-norbornene-2-carboxylate (yield 82%).

The monomers used in the following Synthesis Examples are identified below.

Monomer 1

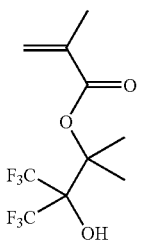

Monomer 2

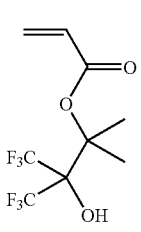

Monomer 3

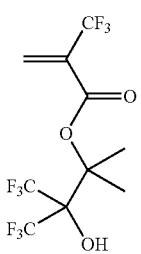

Monomer 4

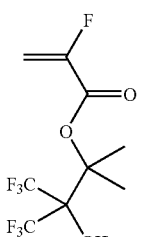

Monomer 5

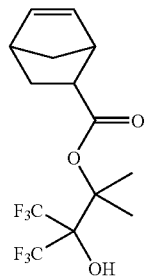

Monomer 6

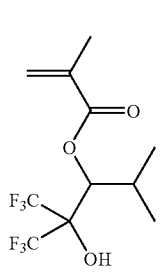

Monomer 7

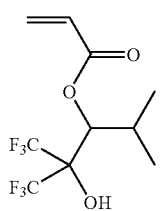

Monomer 8

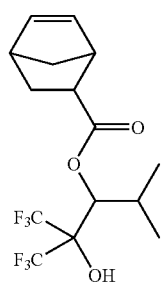

Monomer 9

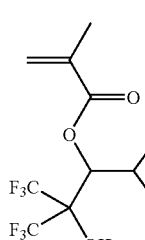

Monomer 10

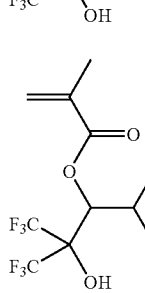

-continued

Monomer 11

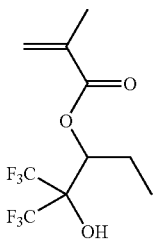

Monomer 12

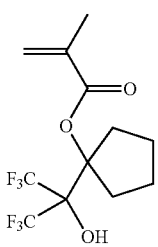

Monomer 13

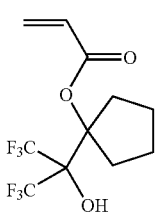

Monomer 14

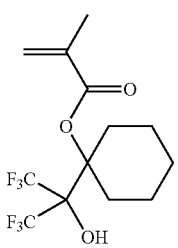

Monomer 15

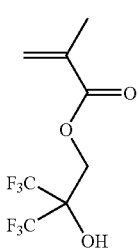

Monomer 16

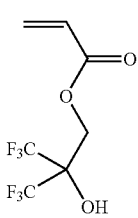

-continued

Monomer 17

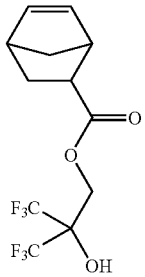

Synthesis Example 2

Polymers within the scope of the invention were synthesized according to the following formulation.

Synthesis Example 2-1

Synthesis of Polymer 1

In 87.5 g of PGMEA were dissolved 25.9 g of Monomer 1, 24.1 g of 3-ethyl-3-exo-tetracyclo[$4.4.0.1^{2,5}.1^{7,10}$]dodecanyl methacrylate, 1,155 mg of 2,2'-azobisisobutyronitrile, and 137 mg of 2-mercaptoethanol. In a nitrogen atmosphere, with stirring, this solution was added dropwise over 4 hours to 29.2 g of PGMEA which was heated at 80° C. The solution was stirred at 80° C. for a further 2 hours. The reaction solution was cooled to room temperature, and with vigorous stirring, added dropwise to 1,000 ml of n-hexane. The resulting solids were collected by filtration and dried in vacuum at 50° C. for 15 hours, obtaining 43.5 g (yield 87%) of a white powder solid designated Polymer 1. Polymer 1 had the compositional proportion and Mw shown in Table 1.

Polymer 1

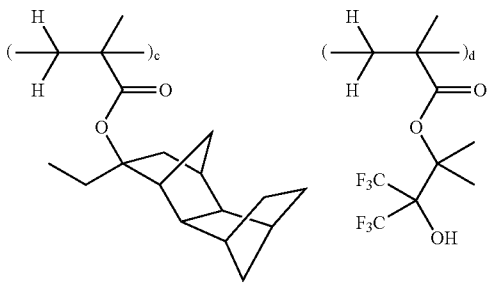

(c = 0.50, d = 0.50, Mw = 7,100)

Synthesis Examples 2-2 to 2-58 and Comparative Synthesis Examples 1-1 to 1-3

Synthesis of Polymers 2 to 61

Polymers 2 to 61 were synthesized by the same procedure as Synthesis Example 2-1 except that the type and proportion of monomers were changed, with their compositional proportion and Mw being shown in Table 1. The structure of the units is shown in Tables 2 to 5.

TABLE 1

|  |  | Resin | Unit 1 (ratio) | Unit 2 (ratio) | Unit 3 (ratio) | Unit 4 (ratio) | Unit 5 (ratio) | Mw |
|---|---|---|---|---|---|---|---|---|
| Synthesis Example | 2-1 | Polymer 1 | F-1M(0.50) | A-1M(0.50) | — | — | — | 7,100 |
|  | 2-2 | Polymer 2 | F-2M(0.50) | A-1M(0.50) | — | — | — | 7,300 |
|  | 2-3 | Polymer 3 | F-3M(0.50) | A-1M(0.50) | — | — | — | 6,700 |
|  | 2-4 | Polymer 4 | F-4M(0.50) | A-1M(0.50) | — | — | — | 6,800 |
|  | 2-5 | Polymer 5 | F-5M(0.50) | A-1M(0.50) | — | — | — | 7,000 |
|  | 2-6 | Polymer 6 | F-6M(0.50) | A-1M(0.50) | — | — | — | 6,900 |
|  | 2-7 | Polymer 7 | F-1M(0.40) | A-1M(0.35) | B-1M(0.25) | — | — | 7,100 |
|  | 2-8 | Polymer 8 | F-1M(0.35) | A-2M(0.40) | B-1M(0.25) | — | — | 7,400 |
|  | 2-9 | Polymer 9 | F-1M(0.40) | A-3M(0.35) | B-1M(0.25) | — | — | 6,900 |
|  | 2-10 | Polymer 10 | F-1M(0.40) | A-4M(0.35) | B-1M(0.25) | — | — | 7,300 |
|  | 2-11 | Polymer 11 | F-1M(0.35) | A-5M(0.40) | B-1M(0.25) | — | — | 6,500 |
|  | 2-12 | Polymer 12 | F-1M(0.35) | A-6M(0.40) | B-1M(0.25) | — | — | 7,000 |
|  | 2-13 | Polymer 13 | F-2M(0.40) | A-1M(0.35) | B-1M(0.25) | — | — | 7,300 |
|  | 2-14 | Polymer 14 | F-2M(0.35) | A-2M(0.40) | B-1M(0.25) | — | — | 7,500 |
|  | 2-15 | Polymer 15 | F-2M(0.40) | A-3M(0.35) | B-1M(0.25) | — | — | 7,000 |
|  | 2-16 | Polymer 16 | F-2M(0.40) | A-4M(0.35) | B-1M(0.25) | — | — | 7,400 |
|  | 2-17 | Polymer 17 | F-2M(0.35) | A-5M(0.40) | B-1M(0.25) | — | — | 6,600 |
|  | 2-18 | Polymer 18 | F-2M(0.35) | A-6M(0.40) | B-1M(0.25) | — | — | 7,100 |
|  | 2-19 | Polymer 19 | F-1M(0.25) | A-1M(0.35) | B-3M(0.40) | — | — | 6,700 |
|  | 2-20 | Polymer 20 | F-1M(0.25) | A-2M(0.40) | B-3M(0.35) | — | — | 6,800 |
|  | 2-21 | Polymer 21 | F-1M(0.25) | A-3M(0.35) | B-3M(0.40) | — | — | 6,800 |
|  | 2-22 | Polymer 22 | F-1M(0.25) | A-4M(0.35) | B-3M(0.40) | — | — | 6,700 |
|  | 2-23 | Polymer 23 | F-1M(0.25) | A-5M(0.40) | B-3M(0.35) | — | — | 6,600 |
|  | 2-24 | Polymer 24 | F-1M(0.25) | A-6M(0.40) | B-3M(0.35) | — | — | 6,700 |
|  | 2-25 | Polymer 25 | F-1M(0.10) | A-1M(0.25) | B-1M(0.25) | B-3M(0.40) | — | 6,500 |
|  | 2-26 | Polymer 26 | F-1M(0.10) | A-1M(0.25) | B-2M(0.25) | B-3M(0.40) | — | 6,900 |
|  | 2-27 | Polymer 27 | F-1M(0.10) | A-1M(0.25) | B-1A(0.25) | B-3M(0.40) | — | 7,000 |
|  | 2-28 | Polymer 28 | F-1M(0.10) | A-1M(0.25) | B-1A(0.25) | B-3A(0.40) | — | 7,300 |
|  | 2-29 | Polymer 29 | F-1M(0.10) | A-1M(0.25) | B-1M(0.25) | B-4M(0.40) | — | 7,200 |
|  | 2-30 | Polymer 30 | F-1M(0.10) | A-1M(0.25) | B-1M(0.25) | B-5M(0.40) | — | 7,000 |
|  | 2-31 | Polymer 31 | F-1M(0.10) | A-1M(0.25) | B-1M(0.25) | B-6M(0.40) | — | 6,800 |
|  | 2-32 | Polymer 32 | F-1M(0.10) | A-2M(0.25) | B-1M(0.25) | B-3M(0.40) | — | 6,900 |
|  | 2-33 | Polymer 33 | F-1M(0.10) | A-3M(0.25) | B-1M(0.25) | B-3M(0.40) | — | 6,800 |
|  | 2-34 | Polymer 34 | F-1M(0.10) | A-4M(0.25) | B-1M(0.25) | B-3M(0.40) | — | 6,700 |
|  | 2-35 | Polymer 35 | F-1M(0.10) | A-5M(0.25) | B-1M(0.25) | B-3M(0.40) | — | 6,800 |
|  | 2-36 | Polymer 36 | F-1M(0.10) | A-6M(0.25) | B-1M(0.25) | B-3M(0.40) | — | 7,300 |
|  | 2-37 | Polymer 37 | F-2M(0.20) | A-1M(0.25) | B-1M(0.25) | B-3M(0.30) | — | 7,500 |
|  | 2-38 | Polymer 38 | F-2M(0.20) | A-2M(0.25) | B-1M(0.25) | B-3M(0.30) | — | 7,100 |
|  | 2-39 | Polymer 39 | F-2M(0.20) | A-3M(0.25) | B-1M(0.25) | B-3M(0.30) | — | 7,400 |
|  | 2-40 | Polymer 40 | F-2M(0.20) | A-4M(0.25) | B-1M(0.25) | B-3M(0.30) | — | 6,700 |
|  | 2-41 | Polymer 41 | F-2M(0.20) | A-5M(0.25) | B-1M(0.25) | B-3M(0.30) | — | 7,300 |
|  | 2-42 | Polymer 42 | F-2M(0.20) | A-6M(0.25) | B-1M(0.25) | B-3M(0.30) | — | 7,000 |
|  | 2-43 | Polymer 43 | F-6M(0.10) | A-1M(0.25) | B-1M(0.25) | B-3M(0.40) | — | 6,800 |
|  | 2-44 | Polymer 44 | F-1M(0.10) | A-1M(0.20) | B-1M(0.25) | B-3M(0.35) | C-1M(0.10) | 6,900 |
|  | 2-45 | Polymer 45 | F-1M(0.10) | A-1M(0.25) | B-1M(0.25) | B-3M(0.30) | C-2M(0.10) | 6,800 |
|  | 2-46 | Polymer 46 | F-1M(0.10) | A-1M(0.20) | B-1M(0.25) | B-3M(0.35) | C-3M(0.10) | 6,900 |
|  | 2-47 | Polymer 47 | F-1M(0.10) | A-1M(0.20) | B-1M(0.25) | B-3M(0.35) | C-4M(0.10) | 7,200 |
|  | 2-48 | Polymer 48 | F-1M(0.10) | A-1M(0.20) | B-1M(0.25) | B-3M(0.35) | C-5M(0.10) | 7,400 |
|  | 2-49 | Polymer 49 | F-1M(0.10) | A-1M(0.15) | A-2M(0.15) | B-1M(0.25) | B-3M(0.35) | 6,900 |
|  | 2-50 | Polymer 50 | F-1M(0.10) | A-1M(0.15) | A-3M(0.10) | B-1M(0.25) | B-3M(0.40) | 6,800 |
|  | 2-51 | Polymer 51 | F-1M(0.10) | A-1M(0.15) | A-4M(0.10) | B-1M(0.25) | B-3M(0.40) | 6,800 |
|  | 2-52 | Polymer 52 | F-1M(0.10) | A-1M(0.15) | A-5M(0.15) | B-1M(0.25) | B-3M(0.35) | 7,000 |
|  | 2-53 | Polymer 53 | F-1M(0.10) | A-1M(0.15) | A-6M(0.10) | B-1M(0.25) | B-3M(0.40) | 6,800 |
|  | 2-54 | Polymer 54 | F-2M(0.15) | A-1M(0.15) | A-2M(0.15) | B-1M(0.25) | B-3M(0.30) | 7,000 |
|  | 2-55 | Polymer 55 | F-2M(0.15) | A-1M(0.15) | A-3M(0.10) | B-1M(0.25) | B-3M(0.35) | 6,900 |
|  | 2-56 | Polymer 56 | F-2M(0.15) | A-1M(0.15) | A-4M(0.10) | B-1M(0.25) | B-3M(0.35) | 6,900 |
|  | 2-57 | Polymer 57 | F-2M(0.15) | A-1M(0.15) | A-5M(0.15) | B-1M(0.25) | B-3M(0.30) | 7,200 |
|  | 2-58 | Polymer 58 | F-2M(0.15) | A-1M(0.15) | A-6M(0.10) | B-1M(0.25) | B-3M(0.35) | 7,000 |
| Comparative Synthesis Example | 1-1 | Polymer 59 | — | A-1M(0.30) | B-1M(0.25) | B-3M(0.45) | — | 7,100 |
|  | 1-2 | Polymer 60 | — | A-1M(0.25) | B-1M(0.25) | B-3M(0.40) | C-1M(0.10) | 6,800 |
|  | 1-3 | Polymer 61 | — | A-1M(0.25) | B-1M(0.25) | B-3M(0.40) | C-5M(0.10) | 7,400 |

TABLE 2

| F-1M (R = CH₃) | F-2M (R = CH₃) | F-3M (R = CH₃) | F-4M (R = CH₃) | F-5M (R = CH₃) | F-6M (R = CH₃) |
| F-1A (R = H) | F-2A (R = H) | F-3A (R = H) | F-4A (R = H) | F-5A (R = H) | F-6A (R = H) |

TABLE 3

| A-1M (R = CH₃) | A-2M (R = CH₃) | A-3M (R = CH₃) | A-4M (R = CH₃) | A-5M (R = CH₃) | A-6M (R = CH₃) |
| A-1A (R = H) | A-2A (R = H) | A-3A (R = H) | A-4A (R = H) | A-5A (R = H) | A-6A (R = H) |

TABLE 4

| B-1M (R = CH₃) | B-2M (R = CH₃) | B-3M (R = CH₃) | B-4M (R = CH₃) | B-5M (R = CH₃) | B-6M (R = CH₃) |
| B-1A (R = H) | B-2A (R = H) | B-3A (R = H) | B-4A (R = H) | B-5A (R = H) | B-6A (R = H) |

TABLE 5

| C-1M (R = CH₃) | C-2M (R = CH₃) | C-3M (R = CH₃) | C-4M (R = CH₃) | C-5M (R = CH₃) |
|---|---|---|---|---|
| C-1A (R = H) | C-2A (R = H) | C-3A (R = H) | C-4A (R = H) | C-5A (R = H) |

[Structural formulas of monomer units C-1 through C-5]

Preparation of Resist Compositions

Examples 1-1 to 1-27 & Comparative Examples 1-1 to 1-3

Resist compositions were prepared by using inventive Polymers or comparative Polymers 59 to 61 as the base resin, and dissolving the polymer, a photoacid generator (PAG), and a basic compound (Base) in a solvent mixture (PGMEA and CyHO) containing 0.01 wt % of surfactant KH-20 (Asahi Glass Co., Ltd.) in accordance with the recipe shown in Table 6. These compositions were each filtered through a Teflon® filter having a pore diameter 0.2 μm, thereby giving inventive resist solutions R-01 to 27 and comparative resist solutions R-28 to 30.

The photoacid generator, base and solvent shown in Table 6 have the following meanings.

PAG-1: triphenylsulfonium nonafluorobutanesulfonate

PAG-2: 4-t-butoxyphenyldiphenylsulfonium nonafluorobutanesulfonate

PAG-3: triphenylsulfonium 1,1,3,3,3-pentafluoro-2-cyclohexylcarboxypropanesulfonate Base-1: tri(2-methoxymethoxyethyl)amine Base-2: 2-(2-methoxyethoxymethoxy)ethylmorpholine Base-3: N-(2-acetoxyethyl)benzimidazole PGMEA: 1-methoxyisopropyl acetate CyHO: cyclohexanone

TABLE 6

| | | Resist | Resin (pbw) | PAG (pbw) | Base (pbw) | Solvent 1 (pbw) | Solvent 2 (pbw) |
|---|---|---|---|---|---|---|---|
| Example | 1-1 | R-01 | Polymer 7(80) | PAG-1(4.4) | Base-1(0.94) | PGMEA(560) | CyHO(240) |
| | 1-2 | R-02 | Polymer 13(80) | PAG-1(4.4) | Base-1(0.94) | PGMEA(560) | CyHO(240) |
| | 1-3 | R-03 | Polymer 19(80) | PAG-1(4.4) | Base-1(0.94) | PGMEA(560) | CyHO(240) |
| | 1-4 | R-04 | Polymer 25(80) | PAG-1(4.4) | Base-1(0.94) | PGMEA(560) | CyHO(240) |
| | 1-5 | R-05 | Polymer 25(80) | PAG-2(4.9) | Base-1(0.94) | PGMEA(560) | CyHO(240) |
| | 1-6 | R-06 | Polymer 25(80) | PAG-3(4.6) | Base-1(0.94) | PGMEA(560) | CyHO(240) |
| | 1-7 | R-07 | Polymer 25(80) | PAG-1(4.4) | Base-2(0.74) | PGMEA(560) | CyHO(240) |
| | 1-8 | R-08 | Polymer 25(80) | PAG-1(4.4) | Base-3(0.64) | PGMEA(560) | CyHO(240) |
| | 1-9 | R-09 | Polymer 26(80) | PAG-1(4.4) | Base-1(0.94) | PGMEA(560) | CyHO(240) |
| | 1-10 | R-10 | Polymer 29(80) | PAG-1(4.4) | Base-1(0.94) | PGMEA(560) | CyHO(240) |
| | 1-11 | R-11 | Polymer 30(80) | PAG-1(4.4) | Base-1(0.94) | PGMEA(560) | CyHO(240) |
| | 1-12 | R-12 | Polymer 31(80) | PAG-1(4.4) | Base-1(0.94) | PGMEA(560) | CyHO(240) |
| | 1-13 | R-13 | polymer 32(80) | PAG-1(4.4) | Base-1(0.94) | PGMEA(560) | CyHO(240) |
| | 1-14 | R-14 | Polymer 33(80) | PAG-1(4.4) | Base-1(0.94) | PGMEA(560) | CyHO(240) |
| | 1-15 | R-15 | Polymer 34(80) | PAG-1(4.4) | Base-1(0.94) | PGMEA(560) | CyHO(240) |
| | 1-16 | R-16 | Polymer 35(80) | PAG-1(4.4) | Base-1(0.94) | PGMEA(560) | CyHO(240) |
| | 1-17 | R-17 | Polymer 36(80) | PAG-1(4.4) | Base-1(0.94) | PGMEA(560) | CyHO(240) |
| | 1-18 | R-18 | Polymer 37(80) | PAG-1(4.4) | Base-1(0.94) | PGMEA(560) | CyHO(240) |
| | 1-19 | R-19 | Polymer 38(80) | PAG-1(4.4) | Base-1(0.94) | PGMEA(560) | CyHO(240) |
| | 1-20 | R-20 | Polymer 39(80) | PAG-1(4.4) | Base-1(0.94) | PGMEA(560) | CyHO(240) |
| | 1-21 | R-21 | Polymer 40(80) | PAG-1(4.4) | Base-1(0.94) | PGMEA(560) | CyHO(240) |
| | 1-22 | R-22 | Polymer 41(80) | PAG-1(4.4) | Base-1(0.94) | PGMEA(560) | CyHO(240) |
| | 1-23 | R-23 | Polymer 42(80) | PAG-1(4.4) | Base-1(0.94) | PGMEA(560) | CyHO(240) |
| | 1-24 | R-24 | Polymer 44(80) | PAG-1(4.4) | Base-1(0.94) | PGMEA(560) | CyHO(240) |
| | 1-25 | R-25 | Polymer 45(80) | PAG-1(4.4) | Base-1(0.94) | PGMEA(560) | CyHO(240) |
| | 1-26 | R-26 | Polymer 52(80) | PAG-1(4.4) | Base-1(0.94) | PGMEA(560) | CyHO(240) |
| | 1-27 | R-27 | Polymer 57(80) | PAG-1(4.4) | Base-1(0.94) | PGMEA(560) | CyHO(240) |
| Comparative Example | 1-1 | R-28 | Polymer 59(80) | PAG-1(4.4) | Base-1(0.94) | PGMEA(560) | CyHO(240) |
| | 1-2 | R-29 | Polymer 60(80) | PAG-1(4.4) | Base-1(0.94) | PGMEA(560) | CyHO(240) |
| | 1-3 | R-30 | Polymer 61(80) | PAG-1(4.4) | Base-1(0.94) | PGMEA(560) | CyHO(240) |

Evaluation of Immersion Liquid Penetration Preventing Effect

Examples 2-1 to 2-27 & Comparative Examples 2-1 to 2-3

A resist composition comprising the inventive polymer as a base resin was evaluated for the effect of preventing immersion liquid (water) from penetrating into a resist film. Specifically, the resist composition (R-01 to 27) of Example 1 or comparative resist composition (R-28 to 30) was coated onto a silicon wafer pretreated with hexamethyl disilazane (HMDS) and baked at 100° C. for 60 seconds to form a resist film of 50 nm thick.

An inclination contact angle meter Drip Master 500 by Kyowa Interface Science Co., Ltd. was used. While the resist-coated wafer was kept horizontal, 50 microliters (μl) of deionized water was dripped thereon to form a droplet. While the wafer was gradually inclined, the angle (sliding angle) at which the droplet started sliding down was determined as well as receding contact angle. The results are shown in Table 7.

TABLE 7

| | Resist | Sliding angle (°) | Receding contact angle (°) |
|---|---|---|---|
| Example 2-1 | R-01 | 22 | 63 |
| Example 2-2 | R-02 | 20 | 65 |
| Example 2-3 | R-03 | 28 | 55 |
| Example 2-4 | R-04 | 25 | 57 |
| Example 2-5 | R-05 | 23 | 59 |
| Example 2-6 | R-06 | 23 | 58 |
| Example 2-7 | R-07 | 25 | 57 |
| Example 2-8 | R-08 | 24 | 58 |
| Example 2-9 | R-09 | 26 | 56 |
| Example 2-10 | R-10 | 24 | 59 |
| Example 2-11 | R-11 | 24 | 58 |
| Example 2-12 | R-12 | 26 | 56 |
| Example 2-13 | R-13 | 26 | 55 |
| Example 2-14 | R-14 | 26 | 56 |
| Example 2-15 | R-15 | 25 | 57 |
| Example 2-16 | R-16 | 27 | 54 |
| Example 2-17 | R-17 | 27 | 55 |
| Example 2-18 | R-18 | 21 | 60 |
| Example 2-19 | R-19 | 23 | 58 |
| Example 2-20 | R-20 | 23 | 58 |
| Example 2-21 | R-21 | 25 | 56 |
| Example 2-22 | R-22 | 25 | 57 |
| Example 2-23 | R-23 | 22 | 56 |
| Example 2-24 | R-24 | 27 | 54 |
| Example 2-25 | R-25 | 20 | 60 |
| Example 2-26 | R-26 | 24 | 57 |
| Example 2-27 | R-27 | 23 | 59 |
| Comparative Example 2-1 | R-28 | 32 | 47 |
| Comparative Example 2-2 | R-29 | 29 | 52 |
| Comparative Example 2-3 | R-30 | 35 | 46 |

As seen from Table 7, the resist compositions comprising the inventive polymers as the base resin have a smaller sliding angle and a larger receding contact angle, indicating that the resist films are effective for preventing penetration of immersion liquid (water). A smaller sliding angle also indicates an easier flow of water on the film, advantageously allowing for a higher scanning speed during scan exposure. A larger receding contact angle indicates that fewer liquid droplets are left during high-speed scan exposure.

Evaluation of Resist Composition

Examples 3-1 to 3-27 & Comparative Examples 3-1 to 3-3

Each of inventive resist compositions (R-01 to 27) and comparative resist compositions (R-28 to 30) was spin coated on a silicon wafer having an antireflective coating (ARC-29A, Nissan Chemical Co., Ltd.) of 78 nm thick and baked at 110° C. for 60 seconds, forming a resist film of 170 nm thick. The wafer was exposed by means of an ArF excimer laser stepper (Nikon Corp., NA 0.68), post-exposure baked (PEB) for 60 seconds, and puddle developed with a 2.38 wt % tetramethylammonium hydroxide aqueous solution for 30 seconds, forming a 1:1 line-and-space pattern. During the PEB, an optimum temperature for each resist composition was employed. The wafer as developed was observed under a top-down scanning electron microscope (SEM). The optimum exposure (Eop, $mJ/cm^2$) was defined as the exposure dose which provided a 1:1 resolution at the top and bottom of a 0.11-μm 1:1 line-and-space pattern. The maximum resolution of the resist was defined as the minimum line width (in increments of 0.01 μm) of the lines and spaces that separated at the optimum exposure, with smaller values indicating better resolution.

The evaluation results (Eop and maximum resolution) of the resist compositions are shown in Table 8.

TABLE 8

| | Resist | PEB temp. (° C.) | Eop ($mJ/cm^2$) | Maximum resolution (mm) |
|---|---|---|---|---|
| Example 3-1 | R-01 | 105 | 34.0 | 0.10 |
| Example 3-2 | R-02 | 105 | 36.0 | 0.10 |
| Example 3-3 | R-03 | 110 | 41.0 | 0.09 |
| Example 3-4 | R-04 | 110 | 40.0 | 0.09 |
| Example 3-5 | R-05 | 110 | 44.0 | 0.10 |
| Example 3-6 | R-06 | 110 | 40.0 | 0.09 |
| Example 3-7 | R-07 | 110 | 42.0 | 0.09 |
| Example 3-8 | R-08 | 110 | 43.0 | 0.09 |
| Example 3-9 | R-09 | 110 | 42.0 | 0.10 |
| Example 3-10 | R-10 | 110 | 40.0 | 0.10 |
| Example 3-11 | R-11 | 110 | 41.0 | 0.10 |
| Example 3-12 | R-12 | 110 | 38.0 | 0.10 |
| Example 3-13 | R-13 | 125 | 42.0 | 0.09 |
| Example 3-14 | R-14 | 115 | 42.0 | 0.09 |
| Example 3-15 | R-15 | 120 | 44.0 | 0.09 |
| Example 3-16 | R-16 | 120 | 42.0 | 0.09 |
| Example 3-17 | R-17 | 115 | 41.0 | 0.09 |
| Example 3-18 | R-18 | 110 | 42.0 | 0.09 |
| Example 3-19 | R-19 | 125 | 41.0 | 0.10 |
| Example 3-20 | R-20 | 115 | 41.0 | 0.10 |
| Example 3-21 | R-21 | 120 | 40.0 | 0.09 |
| Example 3-22 | R-22 | 120 | 41.0 | 0.09 |
| Example 3-23 | R-23 | 115 | 41.0 | 0.09 |
| Example 3-24 | R-24 | 110 | 40.0 | 0.09 |
| Example 3-25 | R-25 | 120 | 41.0 | 0.10 |
| Example 3-26 | R-26 | 115 | 40.0 | 0.09 |
| Example 3-27 | R-27 | 110 | 40.0 | 0.10 |
| Comparative Example 3-1 | R-28 | 110 | 44.0 | 0.13 |
| Comparative Example 3-2 | R-29 | 110 | 42.0 | 0.11 |
| Comparative Example 3-3 | R-30 | 110 | 43.0 | 0.11 |

It is evident from Table 8 that the resist compositions within the scope of the invention are improved in resolution and dissolution when processed by ArF excimer laser lithography.

All the aforementioned patent publications are incorporated herein by reference.

Japanese Patent Application No. 2006-022319 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A fluorinated monomer having one of the general formula (5), (6), (9), (10), (13), (14), (17) or (18)

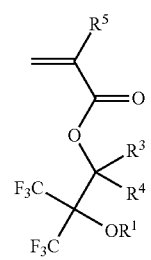
(5)

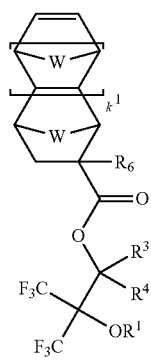
(6)

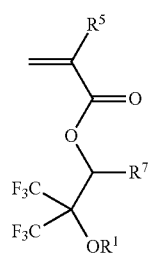
(9)

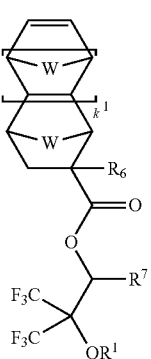
(10)

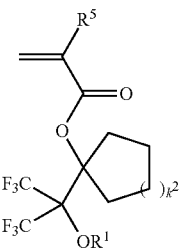
(13)

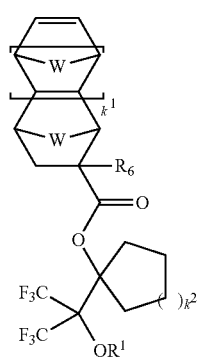
(14)

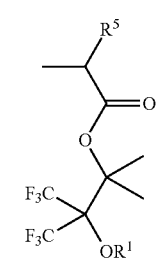
(17)

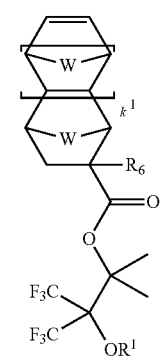
(18)

wherein $R^1$ is hydrogen or a straight, branched or cyclic monovalent hydrocarbon group of 1 to 20 carbon atoms in which any constituent —$CH_2$— moiety may be replaced by —O— or —C(=O)—, $R^3$ and $R^4$ are each independently hydrogen or a straight, branched or cyclic monovalent hydrocarbon group of 1 to 8 carbon atoms, $R^5$ and $R^6$ are each independently hydrogen, fluorine, methyl or trifluoromethyl, $R^7$ is a straight, branched or cyclic monovalent hydrocarbon group of 2 to 8 carbon atoms, W is —$CH_2$— or —O—, and $k^1$ is 0 or 1 and $k^2$ is 1 or 2.

2. The fluorinated monomer according to claim 1 having the general formula (6),

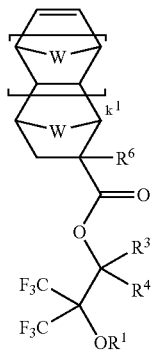
(6)

wherein $R^1$, $R^3$, $R^4$, $R^6$, W and $k^1$ are as defined in claim 1.

3. The fluorinated monomer according to claim 1 having the general formula (9),

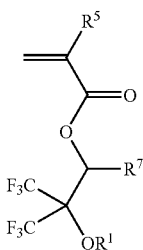
(9)

wherein $R^1$, $R^5$, and $R^7$ are as defined in claim 1.

4. The fluorinated monomer according to claim 1 having the general formula (10),

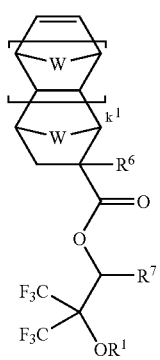
(10)

wherein $R^1$, $R^6$, $R^7$, W, and $k^1$ are as defined in claim 1.

5. The fluorinated monomer according to claim 1 having the general formula (13),

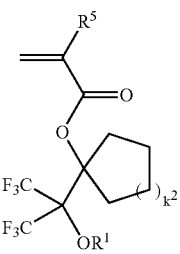
(13)

wherein $R^1$, $R^5$, and $k^2$ are as defined in claim 1.

6. The fluorinated monomer according to claim 1 having the general formula (14),

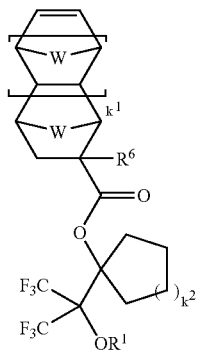
(14)

wherein $R^1$, $R^6$, W, $k^1$, and $k^2$ are as defined in claim 1.

7. The fluorinated monomer according to claim 1 having the general formula (17),

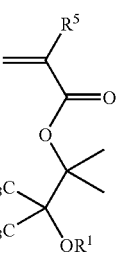
(17)

wherein $R^1$ and $R^5$ are as defined in claim 1.

8. The fluorinated monomer according to claim 1 having the general formula (18),
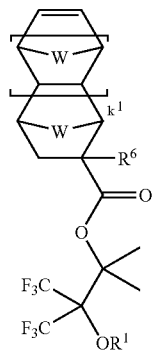
(18)
wherein $R^1$, $R^6$, W, and $k^1$ are as defined in claim 1.
9. The fluorinated monomer according to claim 1 having the general formula (5),
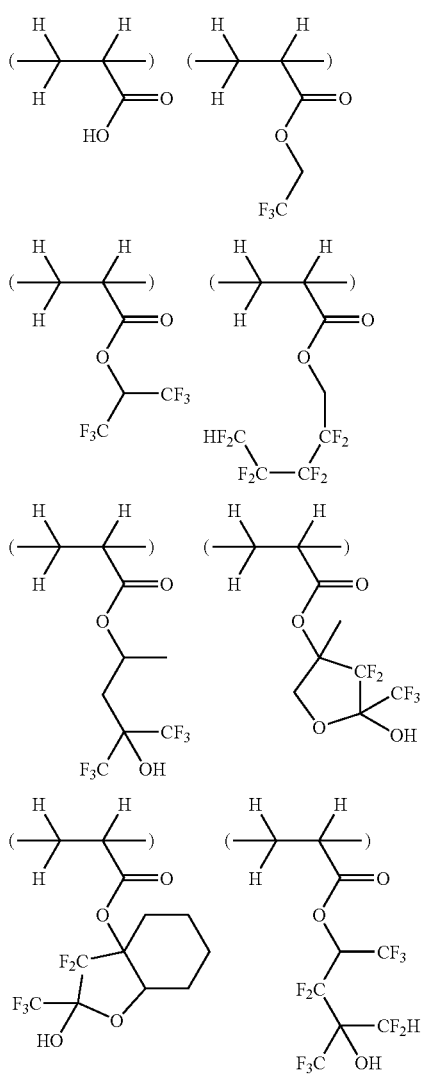
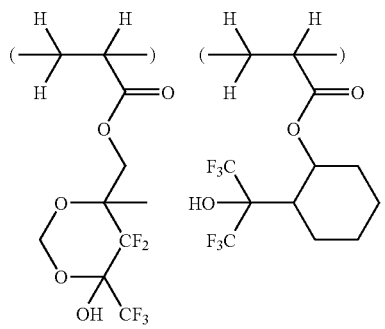
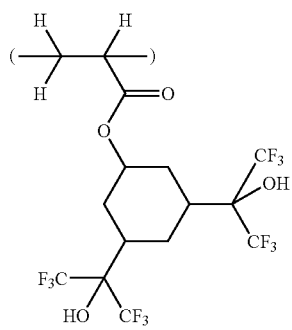
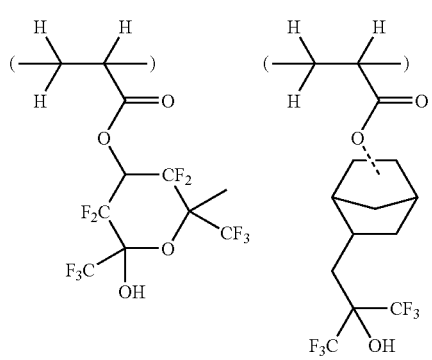
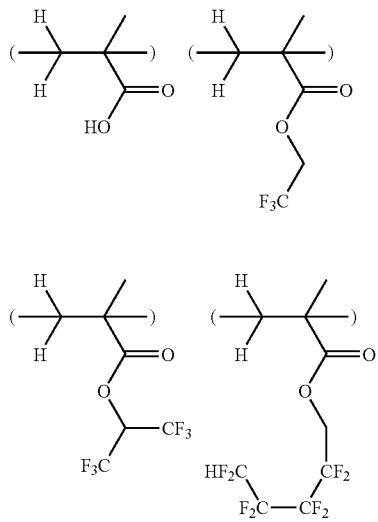

-continued
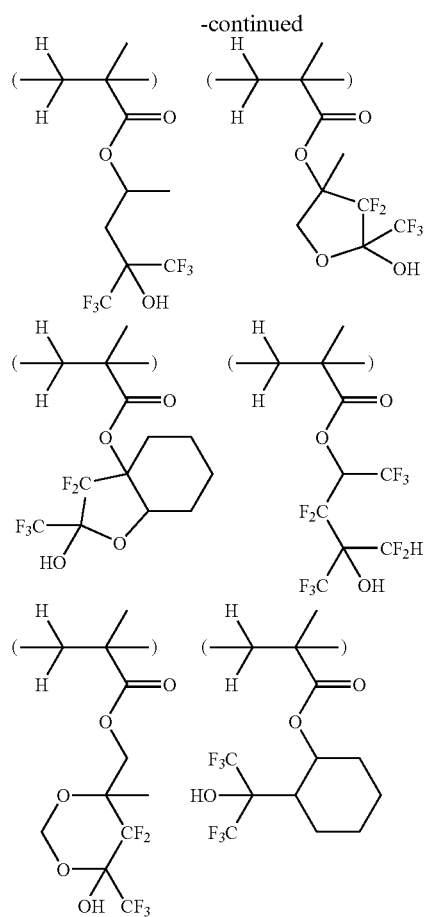
-continued
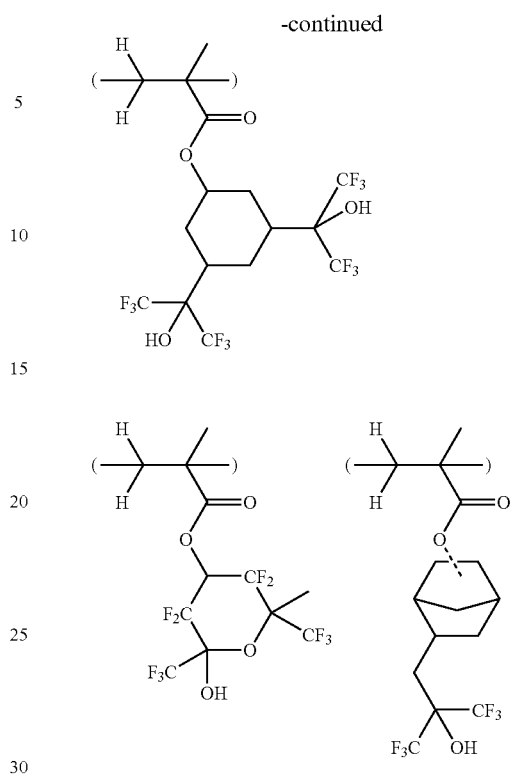
wherein $R^1$ $R^3$, $R^4$ and $R^5$.
* * * * *